United States Patent [19]

Beck et al.

[11] Patent Number: 4,620,865
[45] Date of Patent: Nov. 4, 1986

[54] HERBICIDAL AND ALGICIDAL 1,5-DISUBSTITUTED-1H-PYRAZOLE-4-CARBOXAMIDES

[75] Inventors: James R. Beck, Indianapolis; Michael P. Lynch, Greenfield, both of Ind.

[73] Assignee: Eli Lilly and Company, Indianapolis, Ind.

[21] Appl. No.: 833,309

[22] Filed: Feb. 24, 1986

Related U.S. Application Data

[63] Continuation of Ser. No. 650,136, Sep. 13, 1984, abandoned, which is a continuation-in-part of Ser. No. 549,122, Nov. 7, 1983, abandoned.

[51] Int. Cl.$^4$ .................. A01N 43/56; C07D 231/18; C07D 401/04
[52] U.S. Cl. .................................. 71/67; 71/92; 546/162; 546/279; 548/377; 548/378
[58] Field of Search ............... 548/377, 378; 546/162, 546/279; 71/67, 92

[56] References Cited

U.S. PATENT DOCUMENTS

| | | | |
|---|---|---|---|
| 2,925,418 | 2/1960 | Druey et al. | 548/362 |
| 2,965,643 | 12/1960 | Druey et al. | 548/362 |
| 3,187,006 | 6/1965 | Druey et al. | 548/362 |
| 3,567,735 | 3/1971 | Druey et al. | 548/362 |
| 3,732,225 | 5/1973 | Breuer et al. | 548/362 |
| 3,760,084 | 9/1973 | Marsico et al. | 548/362 |
| 3,953,467 | 4/1976 | Fujimura et al. | 548/374 |
| 4,134,987 | 1/1979 | Huppatz | 548/377 |
| 4,245,106 | 1/1981 | Brannigan et al. | 548/378 |
| 4,298,749 | 1/1981 | Plath et al. | 548/377 |
| 4,316,039 | 2/1982 | Plath et al. | 548/362 |
| 4,316,040 | 2/1982 | Plath et al. | 548/377 |
| 4,346,094 | 8/1982 | Beck et al. | 548/206 |

FOREIGN PATENT DOCUMENTS

| | | | |
|---|---|---|---|
| 1058519 | 6/1959 | Fed. Rep. of Germany | 548/362 |
| 49070966 | 11/1972 | Japan | 548/362 |
| 884851 | 12/1961 | United Kingdom | 548/362 |
| 1488285 | 10/1977 | United Kingdom | 548/377 |
| 1573942 | 8/1980 | United Kingdom | 548/377 |
| 2070604 | 9/1981 | United Kingdom | 548/362 |

OTHER PUBLICATIONS

Chem. Ber. 34, 1303 (1901) A. Michaelis, U. Voss and M. Greiss: Ueber einige Phenylalkyl-5-halogenpyrazole., Apr. 22, 1901.
Cheng et al., "Potential . . . Pyrazolo(3,4-d)-pyrimidines.", J. Org. Chem., 23, 852-61 (1958).
Cheng et al., "Potential . . . Pyrazolo (3,4-d)-pyrimidines.", J. Org. Chem., 21, 1240-56 (1956).
Kinugawa et al., "Studies . . . Derivatives.", Chem. Pharm. Bull., 12(2), 182-91 (1964).
Chemical Abstract, 55, 13459f (1961).
Par P. Duquenois. N-Phenylpyrazolonlarin ve N-Phenylpyrazollerin Fotolizi., Rev. Faculte Sci. Univ. Istanbul, 6A:116-119, 1941.
J. Chem. Soc., 1969, vol. 11, pp. 1495-1499.
Agric. Biol. Chem., 1984, vol. 48(1), 45-90.

Primary Examiner—Richard A. Schwartz
Assistant Examiner—Kurt G. Briscoe
Attorney, Agent, or Firm—Joseph A. Jones; Leroy Whitaker

[57] ABSTRACT

1,5-Disubstituted-1H-pyrazole-4-carboxamide derivatives, useful as herbicides and aquatic algicides.

48 Claims, No Drawings

HERBICIDAL AND ALGICIDAL 1,5-DISUBSTITUTED-1H-PYRAZOLE-4-CARBOXAMIDES

CROSS REFERENCE TO RELATED APPLICATION

This application is a continuation of application Ser. No. 650,136, filed 9-13-84, now abandoned, which is a continuation-in-part of our copending application Ser. No. 549,122, filed Nov. 7, 1983, now abandoned.

SUMMARY OF THE INVENTION

The present invention relates to a compound of the formula

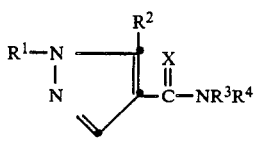

wherein
$R^1$ is $C_1-C_6$ alkyl, $C_5-C_6$ cycloalkyl,

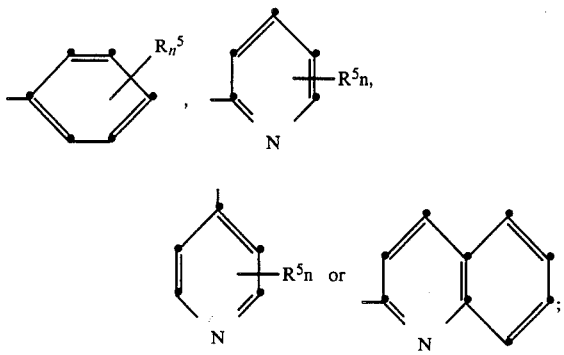

$R^2$ is halogen, $C_1-C_4$ alkyl, trifluoromethyl, $C_1-C_4$ alkoxy, $C_1-C_4$ alkylthio or $C_1-C_4$ alkylsulfonyl;
$R^3$ is hydrogen, $C_1-C_4$ alkyl or $C_1-C_4$ alkoxy;
$R^4$ is cyclopropyl, $C_1-C_4$ alkyl or $C_1-C_4$ alkoxy;
$R^5$ is halogen, $C_1-C_4$ alkyl, $C_1-C_4$ alkoxy, $C_1-C_4$ haloalkyl, $C_1-C_4$ haloalkoxy or nitro;
X is O or S; and
n is 0-3;
with the following provisos: the combined total of carbon atoms for $R^3$ and $R^4$ does not exceed 5; when $R^1$ is phenyl, $R^5$ is $C_1-C_4$ alkyl, and $R^2$ is halogen, alkoxy, alkylthio, or alkylsulfonyl, the $R^5$ substituent exists at other than the 2 or 6 position of the phenyl ring; when $R^3$ is $C_1-C_4$ alkoxy, $R^4$ is other than $C_1-C_4$ alkoxy; and when $R^1$ is phenyl, $R^5$ is $C_1-C_4$ alkoxy and $R^2$ is other than bromine, the $R^5$ substituent exists at other than the 3 or 5 position of the phenyl ring.

The present compounds are useful both as herbicides and aquatic algicides. Compositions containing these compounds are also disclosed.

DETAILED DESCRIPTION OF THE INVENTION

In the above formula, $C_1-C_4$ alkyl represents a straight or branched alkyl chain having from one to four carbon atoms. Typical $C_1-C_4$ alkyl groups include methyl, ethyl, n-propyl, isopropyl, n-butyl, sec.-butyl, t-butyl, and the like. $C_1-C_6$ alkyl includes the foregoing groups as well as $C_5$ and $C_6$ groups including pentyl, hexyl, tert-pentyl, and 1-methyl-1-ethylpropyl.

$C_1-C_4$ Alkoxy represents a straight or branched alkoxy chain having from one to four carbon atoms. Typical $C_1-C_4$ alkoxy groups include methoxy, ethoxy, n-propoxy, isopropoxy, n-butoxy, sec.-butoxy, isobutoxy, t-butoxy, and the like.

The terms "halogen" or "halo" represent fluorine, chlorine, bromine and iodine.

$C_1-C_4$ Haloalkyl represents a $C_1-C_4$ alkyl group bearing one or more halogen substituents. Such haloalkyl groups include trifluoromethyl, 2,2,2-trifluoroethyl, pentabromoethyl, 3-chloropropyl, 2-iodopropyl, 4-fluorobutyl and the like.

$C_1-C_4$ Haloalkoxy is a $C_1-C_4$ alkoxy group bearing one or more halogen atoms. Typical members of this classification include trifluoromethoxy, 1,1,2,2-tetrafluoroethoxy, pentafluoroethoxy, 3-bromopropoxy, 4-chlorobutoxy, 4-iodobutoxy and the like.

$C_1-C_4$ Alkylthio represents a straight chain or branched alkylthio group having from one to four carbon atoms. Typical $C_1-C_4$ alkylthio groups include methylthio, ethylthio, n-propylthio, isopropylthio, n-butylthio, sec-butylthio, t-butylthio and the like.

Preferred compounds have the above formula wherein $R^1$ is phenyl or tert-butyl, $R^2$ is chlorine, bromine, or trifluoromethyl, $R^5$ is halogen, n is 0 or 1, and $R^3$ is hydrogen, methyl or ethyl and $R^4$ is methyl, ethyl, or cyclopropyl. Particularly preferred compounds have the above formula wherein $R^3$ is hydrogen and $R^4$ is methyl or cyclopropyl.

GENERAL PREPARATION METHODS

The compounds of the present invention are prepared by procedures well known to those skilled in the art. The preferred process comprises the direct coupling of a 5-substituted-4-pyrazolecarboxylic acid with an appropriately substituted amine in the presence of a coupling reagent to provide the corresponding carboxamide according to the following reaction scheme:

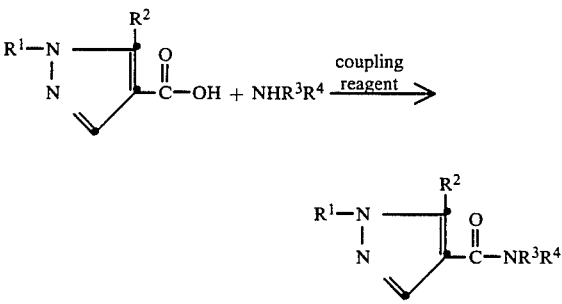

This reaction process necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as N-ethoxycarbonyl-2-ethoxy-1,2-dihydroquinoline (EEDQ). The direct coupling of a 4-pyrazolecarboxylic acid and an amine is carried out by adding about an equimolar quantity of the amine starting material to a solution of the carboxylic acid in the presence of an equimolar quantity or slight excess of coupling reagent. The reaction generally is carried out in an unreactive organic solvent such as dichloromethane or dimethylformamide, and usually is complete within about twenty-four hours when conducted at a temperature of about 0° to about 30° C. The product is then typically isolated by filtration. The carboxamide product thus formed can be further purified if needed by any of several routine methods, including crystallization from common solvents, chromatography over solid supports such as silica or alumina, and related purification techniques.

The carboxamides of the invention may also be prepared by reacting a 5-substituted-4-pyrazolecarboxylic acid derivative with an appropriately substituted amine according to the following reaction scheme:

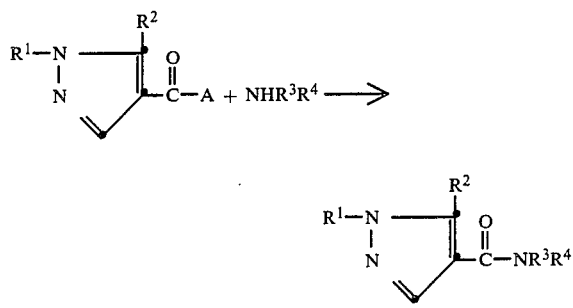

wherein $R^1$, $R^2$, $R^3$ and $R^4$ are as defined above and A is a good leaving group such as $C_1$-$C_6$ alkoxy, halogen

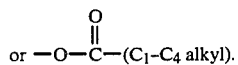

or $-O-\overset{O}{\underset{\parallel}{C}}-(C_1-C_4 \text{ alkyl})$.

The preferred leaving group in this reaction is where A is halogen or $C_1$-$C_6$ alkoxy. This reaction can be carried out by combining the carboxylic acid derivative with about an equimolar quantity of the amine in a mutual solvent such as tetrahydrofuran, diethyl ether, dichloromethane, dioxane, dimethylsulfoxide, dimethylformamide, benzene, toluene, and the like. If desired, a base can be utilized in the acylation reaction when A is halogen to act as an acid scavenger. Commonly used bases include sodium carbonate, potassium carbonate, pyridine, triethylamine and related bases. Bases such as pyridine act as their own solvent and need no additional solvent. The reaction generally is substantially complete after about two to about 200 hours when carried out at a temperature of about 20° to about 200° C., preferably from about 30° to about 100° C. The product of the reaction may be isolated by simply removing the reaction solvent, for instance by evaporation under reduced pressure. Also, the reaction mixture may be added to water and the product collected by filtration or extracted into a water immiscible solvent. The product thus isolated can be further purified if desired by any of several well known techniques.

Thiocarboxamides defined by the above general formula wherein X is sulfur form another important group of compounds that are herbicidally active and are a further embodiment of this invention. The thiocarboxamides of the invention are preferably prepared by thiating the corresponding carboxamide according to the following scheme:

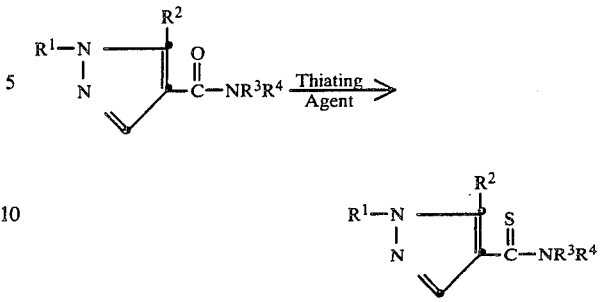

Any of several thiating agents can be employed in this reaction, including phosphorus pentasulfide. An especially preferred thiating agent is Lawesson's Reagent, which is 2,4-bis(4-methoxyphenyl)-1,3-dithia-2,4-diphosphetane-2,4-disulfide. This thiating reagent and its general use are described in detail in *Tetrahedron Letters*, 21, 4061 (1980). The thiation reaction is preferably carried out by reacting approximately equimolar quantities of a carboxamide and Lawesson's Reagent in a mutual organic solvent such as toluene or dioxane. The reaction is generally complete within about one hour to about ten hours when carried out at a temperature of about 50° to about 150° C. The thiocarboxamide thus formed can be isolated and purified by normal methods, such as crystallization and the like.

Preparation of Pyrazolecarboxylic Acids and Esters

The 5-(substituted)-4-pyrazolecarboxylic acids, and analogs thereof, used as starting materials to prepare the carboxamides of the invention are readily prepared by known procedures. The preferred process for the 4-pyrazolecarboxylic acids wherein $R^2$=halogen, alkoxy, alkylthio, or alkylsulfonyl involves reacting a hydrazine derivative with an alkyl (alkoxymethylene)cyanoacetate analog to prepare the corresponding 5-amino-4-pyrazolecarboxylic acid ester. The 5-amino group can then be converted to the 5-halogen, alkoxy, alkylthio, or alkylsulfonyl, and the ester subsequently hydrolyzed to the desired 4-pyrazolecarboxylic acid. The scheme for this reaction is represented by the following:

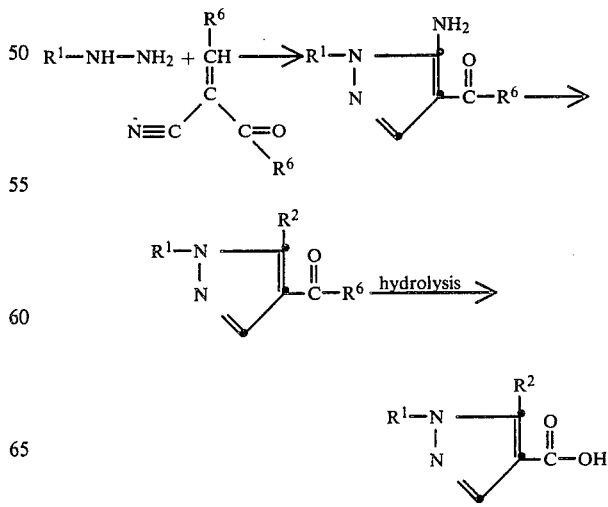

wherein $R^1$ and n are as defined above, $R^2$ is halogen, alkoxy, alkylthio, or alkylsulfonyl, and $R^6$ is $C_1$-$C_6$ alkoxy.

The reaction of a hydrazine with an alkyl (alkoxymethylene)cyanoacetate to prepare a 5-amino-4-pyrazolecarboxylic acid ester is readily practiced by well known procedures. Typically, equimolar quantities of the two starting materials are combined in a suitable organic solvent such as methanol or ethanol. The mixture is stirred at a temperature in the range of from about 20° to 200° C., more preferably at the reflux temperature of the reaction mixture. The product thus formed after about 2 to 24 hours may then be isolated and purified according to standard procedures.

Conversion of the 5-amino group to the other 5-$R^2$ groups is also carried out in known procedures. Those 4-pyrazolecarboxylic acid esters wherein $R^2$ is chlorine, bromine or iodine are prepared by reacting a 5-amino-4-pyrazolecarboxylic acid ester derivative with a diazotizing agent in the presence of an appropriate halogenating agent depending on the desired halogen atom. The resulting ester may then be hydrolyzed to the acid or simply taken as is and converted to the amide as previously described. The scheme for the halogenation reaction is as follows:

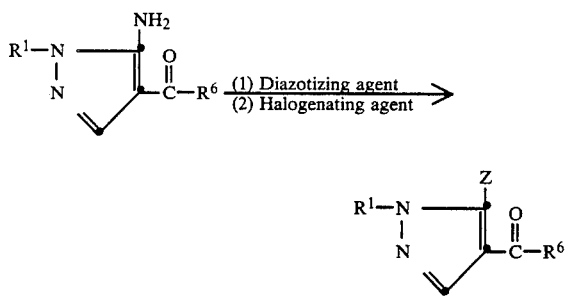

wherein $R^1$ is as defined above, $R^6$ is $C_1$-$C_4$ alkoxy and Z is chlorine, bromine or iodine.

Compounds wherein Z is chlorine in the immediately preceding reaction scheme are prepared by employing nitrosyl chloride as both the diazotizing and halogenating agent. This reaction is typically performed in a non-reactive organic solvent and preferably in the presence of an acid catalyst. Typical solvents include most halogenated solvents with chloroform and carbon tetrachloride being preferred. An excess of the nitrosyl chloride is typically bubbled into the reaction mixture for about 5 to 30 minutes. The mixture may then be heated on a steam bath for a short period of time. The product may then be isolated by simply removing the volatiles under reduced pressure and purifying the product by common techniques if desired.

Compounds of the present invention wherein Z is bromine or iodine in the above reaction scheme are prepared by employing an alkyl nitrite diazotizing agent and the corresponding halogen source as desired. Typical halogen sources include bromine, iodine, bromoform, iodoform and the like. Suitable alkyl nitrite reagents include but are not limited to t-butyl nitrite, isoamyl nitrite and the like. Typically the reaction is performed in a suitable organic solvent such as chloroform or carbon tetrachloride by addition of the alkyl nitrite dropwise into the reaction mixture. The reaction is usually complete after about 1 to 48 hours when conducted at a temperature of 0° C. to 100° C., more preferably at about 10° C. to 50° C. Typically the reaction is worked up by simply evaporating the reaction mixture to dryness under reduced pressure and purifying the residue if desired by standard techniques such as crystallization or column chromatography.

Compounds of the invention wherein $R^2$ is fluorine are preferably prepared by displacing chlorine from the corresponding pyrazolecarboxylic acid ester. This reaction is conducted by adding the appropriate starting material dissolved in a suitable solvent to an excess of the fluorinating agent. Suitable solvents include DMF and DMSO, with the latter being preferred. Typical fluorinating agents include the alkali metal fluorides such as sodium fluoride, potassium fluoride and cesium fluoride. Before being used in the reaction, the fluorinating agent should be dried so as to remove any residual water. Generally this can be performed by refluxing the fluorinating agent in a water immiscible solvent such as toluene. The solvent is then removed before combining the reaction ingredients. The reaction is substantially complete after about 1 to 48 hours when conducted at a temperature in the range from about 75° C. to about 200° C., more preferably from about 100° C. to about 150° C. The product is then generally isolated by pouring the cooled reaction mixture into ice water and collecting the precipitated solid by filtration. The product thus isolated may then be purified if desired by routine procedures.

The 4-pyrazolecarboxylic acid esters wherein $R^2$=alkoxy, alkylthio, or alkylsulfonyl can be prepared by subsequent reactions. For example, compounds of the present invention wherein $R^2$ is $C_1$-$C_4$ alkoxy or $C_1$-$C_4$ alkylthio may be prepared by reacting an appropriately substituted 5-halogen-4-pyrazolecarboxylic acid ester with an alkali metal alkoxy or alkylthio derivative according to well known procedures. Compounds wherein $R^2$ is $C_1$-$C_4$ alkylsulfonyl are prepared by oxidizing the corresponding alkylthio derivative with a suitable oxidizing agent such as hydrogen peroxide or the peracids.

The 5-alkyl and 5-(trifluoromethyl)-4-pyrazolecarboxylic acids are prepared by the following reaction scheme:

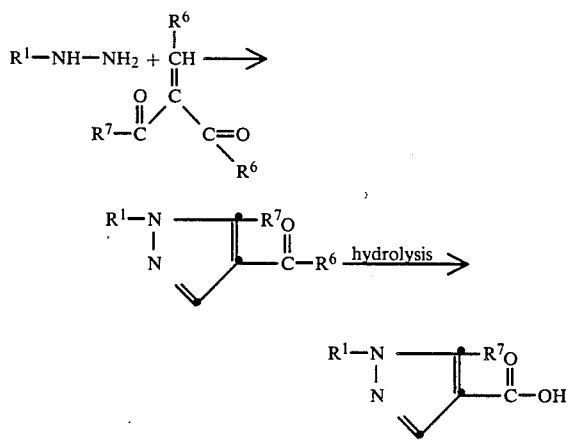

wherein $R^7$=$C_1$-$C_4$ alkyl or trifluoromethyl. The reaction of a hydrazine with an alkyl (alkoxymethylene)trifluoroacetoacetate is readily practiced by known procedures. Typically the reaction is carried out in a suitable solvent such as methanol or ethanol, and at temperatures of from −25° to 0° C. Preferably equimolar quantities of the reactants are employed. Triethylamine or another acid scavenger can be employed. The product can be worked up in conventional procedures.

Compounds wherein $R^2$ is $C_1-C_4$ alkyl may also be prepared by reacting 3-phenyl-4-alkylsydnone with a vinyl acetate derivative to give the corresponding 5-alkyl pyrazole ester which can then be converted to the amide as described herein.

The conversion of the pyrazole carboxylic acid esters to the corresponding carboxylic acids is accomplished by well known hydrolysis conditions. This reaction is typically performed with a suitable base in a mutual organic solvent such as aqueous methanol or ethanol. Suitable bases include the alkali metal hydroxides, preferably sodium hydroxide and potassium hydroxide. Typically the reaction mixture is refluxed for about 1 to 24 hours and then acidified. The resulting precipitate may then be either extracted into a water immiscible solvent or collected by filtration. Purification may be performed if desired by any one of many standard techniques.

The hydrazine and alkyl (alkoxymethylene)cyanoacetate starting materials are either commercially available or readily prepared by known procedures. For example, phenylhydrazine compounds are readily prepared by reacting an appropriately substituted aniline with nitrous acid and then stannous chloride according to known procedures. The alkyl (alkoxymethylene)trifluoroacetoacetates are prepared by the method of R. Jones at *J. Am. Chem. Soc.*, 73, 3684 (1951).

The following Examples are illustrative of compounds of the present invention, as well as methods of their preparation. These Examples are not intended to be limiting to the scope in any respect and should not be so construed.

EXAMPLE 1

5-Bromo-1-phenyl-N-methyl-1H-pyrazole-4-carboxamide

A. 5-Amino-1-phenyl-1H-pyrazole-4-carboxylic acid, ethyl ester

A solution of 31.9 g of phenylhydrazine and 50.0 g of ethyl (ethoxymethylene)cyanoacetate (both reactants were obtained from Aldrich Chemical Company, Milwaukee, Wis.) disssolved in 500 ml of ethanol was refluxed for 6 hours. The mixture was allowed to stand for approximately 48 hours and was refluxed for an additional 8 hours. The reaction mixture was poured into ice water and the precipitated solid was collected by filtration. The solid was recrystallized from ethanol to afford 38.0 g of 5-amino-1-phenyl-1H-pyrazole-4-carboxylic acid, ethyl ester. Yield 44%. mp=101°-103° C.

Analysis calculated for $C_{12}H_{13}N_3O_2$ Theory: C, 62.33; H, 5,67; N, 18.17; Found: C, 62.11; H, 5.59; N, 18.00.

B. 5-Bromo-1-phenyl-1H-pyrazole-4-carboxylic acid, ethyl ester

To a solution of 20.0 g of 5-amino-1-phenyl-1H-pyrazole-4-carboxylic acid, ethyl ester and 10 ml of bromine in 200 ml of chloroform was added 15.8 g of isoamyl nitrite dropwise. The reaction mixture was allowed to stir at room temperature for about 24 hours and the volatiles were removed under reduced pressure. The residue was recrystallized from ethanol/water to provide 10.0 g of 5-bromo-1-phenyl-1H-pyrazole-4-carboxylic acid, ethyl ester. Yield 38%. mp=86°-89° C.

C. 5-Bromo-1-phenyl-1H-pyrazole-4-carboxylic acid

A mixture of 15.5 g of 5-bromo-1-phenyl-1H-pyrazole-4-carboxylic acid, ethyl ester and 14 g of potassium hydroxide in 300 ml of 3A ethanol was refluxed for 3 hours. The solution was poured into ice water and acidified with concentrated hydrochloric acid. The precipitated solid was collected by filtration and recrystallized from ethanol/water to afford 9.0 g of 5-bromo-1-phenyl-1H-pyrazole-4-carboxylic acid. Yield 64%. mp=218°-222° C.

D. Three grams of 5-bromo-1-phenyl-1H-pyrazole-4-carboxylic acid and 2.6 g of carbonyldiimidazole were dissolved in 50 ml of dimethylformamide. The mixture was allowed to stir for 20 minutes and 7 ml of 40% aqueous methylamine was added to the reaction mixture. The mixture was stirred for 2 hours at room temperature and poured into ice water. The precipitated solid was collected by filtration and recrystallized from ethanol/water to afford 1.3 g of 5-bromo-1-phenyl-N-methyl-1H-pyrazole-4-carboxamide. Yield 42%. mp=157°-159° C.

Analysis calculated for $C_{11}H_{10}BrN_3O$ Theory: C, 47.17; H, 3.60; N, 15.00; Found: C, 46.96; H, 3.57; N, 14.97.

EXAMPLE 2

5-Chloro-1-(4-methoxyphenyl)-N-methyl-1H-pyrazole-4-carboxamide

A. 5-Amino-1-(4-methoxyphenyl)-1H-pyrazole-4-carboxylic acid, ethyl ester

Twenty grams of (4-methoxyphenyl)hydrazine hydrochloride, 18.6 g of ethyl (ethoxymethylene)cyanoacetate and 15.2 g of potassium carbonate were combined with 200 ml of ethanol and refluxed for 20 hours. The mixture was cooled and poured into ice water. The precipitated solid was collected by filtration, dried and recrystallized from ethanol to afford 8.1 g of 5-amino-1-(4-methoxyphenyl)-1H-pyrazole-4-carboxylic acid, ethyl ester. Yield 28%. mp=209°-211° C.

Analysis calculated for $C_{13}H_{15}N_3O_3$ Theory: C, 59.76; H, 5.79; N, 16.08; Found: C, 59.93; H, 5.79; N, 15.80.

B. 5-Chloro-1-(4-methoxyphenyl)-1H-pyrazole-4-carboxylic acid, ethyl ester

Nitrosyl chloride was bubbled into a stirring solution of 8.0 g of 5-amino-1-(4-methoxyphenyl)-1H-pyrazole-4-carboxylic acid, ethyl ester in 150 ml of chloroform for 15 minutes. The reaction mixture was then placed on a steam bath for 5 minutes and cooled. The solvent was removed under reduced pressure and the residue recrystallized from ethanol to provide 7.5 g of 5-chloro-1-(4-methoxyphenyl)-1H-pyrazole-4-carboxylic acid, ethyl ester. Yield 90%. mp=100°-101° C.

Analysis calculated for $C_{13}H_{13} ClN_2O_3$ Theory: C, 55.62; H, 4.67; N, 9.98; Cl, 12.63; Found: C, 55.50; H, 4.45; N, 10.01; Cl, 12.92.

C. 5-Chloro-1-(4-methoxyphenyl)-1H-pyrazole-4-carboxylic acid

A solution of 7.5 g of 5-chloro-1-(4-methoxyphenyl)-1H-pyrazole-4-carboxylic acid, ethyl ester and 2.8 g of potassium hydroxide in 200 ml of 3A ethanol was refluxed for 4 hours. The mixture was poured into ice water and acidified with concentrated hydrochloric acid. The precipitated solid was collected by filtration, dried and recrystallized from ethanol to afford 4.2 g of 5-chloro-1-(4-methoxyphenyl)-1H-pyrazole-4-carboxylic acid. Yield 65%. mp=241°-242° C.

Analysis calculated for $C_{11}H_9ClN_2O_3$ Theory: C, 52.29; H, 3.59; N, 11.09; Cl, 14.03; Found: C, 52.38; H, 3.78; N, 10.80; Cl, 13.73.

D. To a solution of 1.2 g of 5-chloro-1-(4-methoxyphenyl)-1H-pyrazole-4-carboxylic acid in 150 ml DMF was added 1.1 g of carbonyldiimidazole and the mixture was allowed to stir at room temperature for 20 minutes. One gram of triethylamine and 0.6 g of methylamine hydrochloride were next added to the reaction mixture and the solution was stirred at room temperature for 20 hours. The mixture was poured into ice water and extracted with ethyl acetate. The organic phase was separated and washed with water, dried, and concentrated under vacuum to dryness. The residue was recrystallized from toluene/hexane to afford 650 mg of 5-chloro-1-(4-methoxyphenyl)-N-methyl-1H-pyrazole-4-carboxamide. Yield 71%. mp=144°–146° C.

Analysis calculated for $C_{12}H_{12}ClN_3O_2$ Theory: C, 54.25; H, 4.55; N, 15.82; Found: C, 54.35; H, 4.74; N, 15.87.

EXAMPLE 3

5-Chloro-1-(3-chlorophenyl)-N-metyl-1H-pyrazole-4-carboxamide

A. 5-Amino-1-(3-chlorophenyl)-1H-pyrazole-4-carboxylic acid, ethyl ester

A solution of 53.7 g of (3-chlorophenyl)hydrazine hydrochloride, 50.8 g of ethyl(ethoxymethylene)cyanoacetate and 41.4 g of potassium carbonate in 500 ml of ethanol was refluxed for 20 hours. The solution was poured into ice water. The precipitated solid was collected by filtration, dried and recrystallized from ethanol/water to provide 53.0 g of 5-amino-1-(3-chlorophenyl)-1H-pyrazole-4-carboxylic acid, ethyl ester. Yield 67%. mp=115°–117° C.

Analysis calculated for $C_{12}H_{12}ClN_3O_2$ Theory: C, 54.25; H, 4.55; N, 15.82; Found: C, 54.08; H, 4.39; N, 15.75.

B. 5-Chloro-1-(3-chlorophenyl)-1H-pyrazole-4-carboxylic acid, ethyl ester

Nitrosyl chloride was bubbled into a cold solution of 10.0 g of 5-amino-1-(3-chlorophenyl)-1H-pyrazole-4-carboxylic acid, ethyl ester in 150 ml of chloroform for 20 minutes. The reaction mixture was then placed on a steam bath for five minutes and the volatiles were removed under reduced pressure. The residue was recrystallized from ethanol to afford 7.8 g of 5-chloro-1-(3-chlorophenyl)-1H-pyrazole-4-carboxylic acid, ethyl ester. Yield 80%. mp=61°–63° C.

Analysis calculated for $C_{12}H_{10}Cl_2N_2O_2$ Theory: C, 50.55; H, 3.54; N, 9.82; Found: C, 50.78; H, 3.29; N, 10.04.

C. 5-Chloro-1-(3-chlorophenyl)-1H-pyrazole-4-carboxylic acid

A mixture of 7.8 g of 5-chloro-1-(3-chlorophenyl)-1H-pyrazole-4-carboxylic acid, ethyl ester and 3.0 g of potassium hydroxide in 200 ml of 3A ethanol was refluxed for four hours. The solution was poured into ice water and acidified with hydrochloric acid. The aqueous acid solution was extracted with ethyl acetate. The organic phase was washed with water, dried, and concentrated under vacuum. The residue was recrystallized from ethanol to afford 5.7 g of 5-chloro-1-(3-chlorophenyl)-1H-pyrazole-4-carboxylic acid. Yield 80%. mp=209°–211° C.

D. A solution of 5.7 g of 5-chloro-1-(3-chlorophenyl)-1H-pyrazole-4-carboxylic acid and 5.4 g of carbonyldiimidazole in 150 ml DMF was stirred at room temperature for 20 minutes. Next, 3.0 g of methylamine hydrochloride and 4.4 g of triethylamine were added and the mixture was stirred at room temperature for 20 hours. The mixture was poured into ice water and the precipitated solid was collected by filtration and dried. The solid was recrystallized from toluene to provide 3.1 g of 5-chloro-1-(3-chlorophenyl)-N-methyl-1H-pyrazole-4-carboxamide. Yield 50%. mp=163°–165° C.

Analysis calculated for $C_{11}H_9Cl_2N_3O$ Theory: C, 48.91; H, 3.36; N, 15.56; Cl, 26.25; Found: C, 48.68; H, 3.52; N, 15.64; Cl, 26.35.

EXAMPLE 4

5-Chloro-1-(3-chlorophenyl)-N-methyl-1H-pyrazole-4-thiocarboxamide

A solution of 3.0 g of 5-chloro-1-(3-chlorophenyl)-N-methyl-1H-pyrazole-4-carboxamide and 6.5 g of Lawesson's Reagent in 150 ml toluene was refluxed for one hour. The solution was cooled and the volatiles were removed under reduced pressure. The residue was chromatographed over silica gel eluting with methylene chloride. The fractions containing the major component were combined and the solvent was evaporated therefrom to afford 1.6 g, following recrystallization from toluene, of 5-chloro-1-(3-chlorophenyl)-N-methyl-1H-pyrazole-4-thiocarboxamide. Yield 56%. mp=128°–130° C.

Analysis calculated for $C_{11}H_9Cl_2N_3S$ Theory: C, 46.17; H, 3.17; N, 14.68; S, 11.20; Found: C, 46.27; H, 3.33; N, 14.79; S, 10.95.

EXAMPLE 5

5-Bromo-1-phenyl-N,N-dimethyl-1H-pyrazole-4-carboxamide

Three grams of 5-bromo-1-phenyl-1H-pyrazole-4-carboxylic acid and 2.6 g of carbonyldiimidazole was dissolved in 50 ml of DMF. The solution was stirred for 20 minutes and 2.3 g of triethylamine and 1.8 g of dimethylamine hydrochloride were added to the reaction mixture. The mixture was stirred at room temperature for 3 hours and was poured into ice water. The precipitated solid was collected by filtration and recrystallized from ethanol/water to afford 1.2 g of 5-bromo-1-phenyl-N,N-dimethyl-1H-pyrazole-4-carboxamide. Yield 37%. mp=79°–81° C.

Analysis calculated for $C_{12}H_{12}BrN_3O$ Theory: C, 49.00; H, 4.11; N, 14.29; Found: C, 48.90; H, 4.08; N, 14.03.

EXAMPLE 6

5-Bromo-1-phenyl-N-ethyl-1H-pyrazole-4-carboxamide

A solution of 2.6 g of 5-bromo-1-phenyl-1H-pyrazole-4-carboxylic acid and 2.4 g of carbonyldiimidazole in 50 ml DMF was stirred at room temperature for 30 minutes. Five milliliters of 70% aqueous ethylamine was next added to the solution and the mixture was stirred for an additional two hours at room temperature. The reaction mixture was poured into ice water and the precipitated solid was collected by filtration. The solid was recrystallized from ethanol to afford 1.0 g of 5-bromo-1-phenyl-N-ethyl-1H-pyrazole-4-carboxamide. Yield 34%. mp=158°–160° C.

Analysis calculated for $C_{12}H_{12}BrN_3O$ Theory: C, 49.00; H, 4.11; N, 14.29; Found: C, 48.74; H, 3.84; N, 14.42.

EXAMPLE 7

5-Bromo-1-phenyl-N-methoxy-1H-pyrazole-4-carboxamide

A solution of 2.6 g of 5-bromo-1-phenyl-1H-pyrazole-4-carboxylic acid and 2.4 g of carbonyldiimidazole in 60 ml DMF was stirred at room temperature for 30 minutes. Two grams of triethylamine and 1.7 g of methoxyamine hydrochloride were added to the solution. The mixture was stirred at room temperature for 24 hours and another equivalent of triethylamine and methoxyamine hydrochloride were added. The mixture was heated on the steam bath for two hours and poured into ice water. The precipitated solid was collected by filtration and recrystallized from ethanol to afford 1.0 g of 5-bromo-1-phenyl-N-methoxy-1H-pyrazole-4-carboxamide. Yield 34%. mp=194°-197° C.

Analysis calculated for $C_{11}H_{10}BrN_3O_2$ Theory: C, 44.59; H, 3.38; N, 14.19; Found: C, 44.33; H, 3.08; N, 13.71.

The following Example represents an illustration of a reaction of a carboxylic acid, ethyl ester with an amine to provide a compound of the invention.

EXAMPLE 8

5-Chloro-1-phenyl-N-methyl-1H-pyrazole-4-carboxamide

A solution of 3.5 g of 5-chloro-1-phenyl-1H-pyrazole-4-carboxylic acid, ethyl ester and 20 ml of 40% aqueous methylamine in 20 ml DMF was stirred at room temperature for about 45 hours. Thin layer chromatography showed mostly starting material so an additional 10 ml of 40% aqueous methylamine was added to the reaction mixture which was stirred for an additional 5 days. The reaction mixture was poured into ice water and the precipitated solid was collected by filtration. After drying, the solid was recrystallized from toluene to afford 2.3 g of 5-chloro-1-phenyl-N-methyl-1H-pyrazole-4-carboxamide. Yield 70%. mp=182°-183° C.

Analysis calculated for $C_{11}H_{10}ClN_3O$ Theory: C, 56.06; H, 4.28; N, 17.83; Found: C, 56.33; H, 4.21; N, 17.77.

The following Examples of carboxamides of the invention were prepared either by the reaction of an appropriate carboxylic acid with an amine according to the general procedures outlined above, or by the modification of a present carboxamide.

EXAMPLE 9

5-Iodo-1-phenyl-N,N-dimethyl-1H-pyrazole-4-carboxamide, mp=93°-94° C.

Analysis calculated for $C_{12}H_{12}IN_3O$ Theory: C, 42.25; H, 3.55; N, 12.32; Found: C, 41.98; H, 3.40; N, 12.06.

EXAMPLE 10

5-Chloro-1-(3,5-dichlorophenyl)-N-methyl-1H-pyrazole-4-carboxamide, mp=171°-173° C.

Analysis calculated for $C_{11}H_8Cl_3N_3O$ Theory: C, 43.38; H, 2.65; N, 13.80; Found: C, 43.64; H, 2.86; N, 14.05.

EXAMPLE 11

5-(Methylsulfonyl)-1-phenyl-N-methyl-1H-pyrazole-4-carboxamide, mp=162°-164° C.

Analysis calculated for $C_{12}H_{13}N_3O_3S$ Theory: C, 51.60; H, 4.69; N, 15.04; Found: C, 51.53; H, 4.56; N, 14.93.

EXAMPLE 12

5-Methyl-1-phenyl-N-methyl-1H-pyrazole-4-carboxamide, mp=174°-177° C.

Analysis calculated for $C_{12}H_{13}N_3O$ Theory: C, 66.96; H, 6.09; N, 19.52; Found: C, 66.75; H, 6.07; N, 19.28.

EXAMPLE 13

5-Chloro-1-(2,3,4-trichlorophenyl)-N-methyl-1H-pyrazole-4-carboxamide, mp=207°-209° C.

Analysis calculated for $C_{11}H_7Cl_4N_3O$ Theory: C, 38.97; H, 2.08; N, 12.39; Found: C, 39.25; H, 2.09; N, 12.24.

EXAMPLE 14

5-Bromo-1-(2,4,6-trichlorophenyl)-N-methyl-1H-pyrazole-4-carboxamide, mp=187°-194° C.

Analysis calculated for $C_{11}H_7BrCl_3N_3O$ Theory: C, 34.46; H, 1.84; N, 10.96; Found: C, 34.66; H, 1.77; N, 11.14.

EXAMPLE 15

5-Chloro-1-phenyl-N-propyl-1H-pyrazole-4-carboxamide, mp=116°-118° C.

Analysis calculated for $C_{13}H_{14}ClN_3O$ Theory: C, 59.21; H, 5.35; N, 15.93; Cl, 13.44; Found: C, 59.49; H, 5.31; N, 16.05; Cl, 13.52.

EXAMPLE 16

5-Chloro-1-phenyl-N-ethyl-1H-pyrazole-4-carboxamide, mp=139°-141° C.

Analysis calculated for $C_{12}H_{12}ClN_3O$ Theory: C, 57.72; H, 4.84; N, 16.83; Cl, 14.20; Found: C, 57.73; H, 5.00; N, 16.73; Cl, 14.13.

EXAMPLE 17

5-Bromo-1-phenyl-N-propyl-1H-pyrazole-4-carboxamide, mp=141°-143° C.

Analysis calculated for $C_{13}H_{14}BrN_3O$ Theory: C, 50.67; H, 4.58; N, 13.64; Found: C, 50.65; H, 4.40; N, 13.41.

EXAMPLE 18

5-Iodo-1-phenyl-N-methyl-1H-pyrazole-4-carboxamide, mp=182°-184° C.

Analysis calculated for $C_{11}H_{10}IN_3O$ Theory: C, 40.39; H, 3.08; N, 12.85; Found: C, 40.26; H, 3.07; N, 12.80.

EXAMPLE 19

5-Chloro-1-(2-chlorophenyl)-N-methyl-1H-pyrazole-4-carboxamide, mp=141°-143° C.

Analysis calculated for $C_{11}H_9Cl_2N_3O$ Theory: C, 48.91; H, 3.36; N, 15.56; Found: C, 48.70; H, 3.28; N, 15.49.

EXAMPLE 20

5-Chloro-1-(2-methoxyphenyl)-N-methyl-1H-pyrazole-4-carboxamide, mp=148°-150° C.

Analysis calculated for $C_{12}H_{12}ClN_3O_2$ Theory: C, 54.25; H, 4.55; N, 15.82; Found: C, 54.16; H, 4.51; N, 15.97.

EXAMPLE 21

5-Chloro-1-[2-(trifluoromethyl)phenyl]-N-methyl-1H-pyrazole-4-carboxamide, mp=145°–147° C.

Analysis calculated for $C_{12}H_9ClF_3N_3O$ Theory: C, 47.46; H, 2.99; N, 13.84; Found: C, 47.62; H, 2.91; N, 13.90.

EXAMPLE 22

5-Bromo-1-[2-(trifluoromethyl)phenyl]-N-methyl-1H-pyrazole-4-carboxamide, mp=154°–156° C.

Analysis calculated for $C_{12}H_9BrF_3N_3O$ Theory: C, 41.40; H, 2.61; N, 12.07; Found: C, 41.61; H, 2,49; N, 11.90.

EXAMPLE 23

5-Chloro-1-[3-(trifluoromethyl)phenyl]-N-methyl-1H-pyrazole-4-carboxamide, mp=148°–150° C.

Analysis calculated for $C_{12}H_9ClF_3N_3O$ Theory: C, 47.46; H, 2.99; N, 13.84; Found: C, 47.53; H, 3.02; N, 14.02.

EXAMPLE 24

5-Bromo-1-[3-(trifluoromethyl)phenyl]-N-methyl-1H-pyrazole-4-carboxamide, mp=129°–131° C.

Analysis calculated for $C_{12}H_9BrF_3N_3O$ Theory: C, 41.40; H, 2.61; N, 12.07; Br, 22.95; Found: C, 41.22; H, 2.50; N, 11.86; Br, 23.11.

EXAMPLE 25

5-Bromo-1-(2,3,4-trichlorophenyl)-N-methyl-1H-pyrazole-4-carboxamide, mp=193°–195° C.

Analysis calculated for $C_{11}H_7BrCl_3N_3O$ Theory: C, 34.46; H, 1.84; N, 10.96; Found: C, 34.67; H, 1.74; N, 10.86.

EXAMPLE 26

5-Chloro-1-[3-(trifluoromethyl)phenyl]-N-ethyl-1H-pyrazole-4-carboxamide, mp=111°–113° C.

Analysis calculated for $C_{13}H_{11}ClF_3N_3O$ Theory: C, 49.15; H, 3.49; N, 13.23; Cl, 11.16; Found: C, 49.06; H, 3.31; N, 13.25; Cl, 10.95.

EXAMPLE 27

5-Bromo-1-[3-(trifluoromethyl)phenyl]-N,N-dimethyl-1H-pyrazole-4-carboxamide, mp=85° C.

Analysis calculated for $C_{13}H_{11}BrF_3N_3O$ Theory: C, 43.12; H, 3.06; N, 11.60; Br, 22.06; Found: C, 42.87; H, 2.92; N, 11.38; Br, 22.16.

EXAMPLE 28

5-Chloro-1-(3,4-dimethylphenyl)-N-methyl-1H-pyrazole-4-carboxamide, mp=156°–158° C.

Analysis calculated for $C_{13}H_{14}ClN_3O$ Theory: C, 59.21; H, 5.35; N, 15.93; Found: C, 59.27; H, 5.07; N, 1.73.

EXAMPLE 29

5-Chloro-1-(3-nitrophenyl)-N,N-dimethyl-1H-pyrazole-4-carboxamide, mp=118°–120° C.

Analysis calculated for $C_{12}H_{11}ClN_4O_3$ Theory: C, 49.02; H, 3.76; N, 19.01; Found: C, 49.08; H, 3.64; N, 19.24.

EXAMPLE 30

5-Chloro-1-(3-nitrophenyl)-N-methyl-1H-pyrazole-4-carboxamide, mp=163°–165° C.

Analysis calculated for $C_{11}H_9ClN_4O_3$ Theory: C, 47.07; H, 3.23; N, 19.96; Found: C, 46.80; H, 3.08; N, 19.85.

EXAMPLE 31

5-Bromo-1-(3-fluorophenyl)-N-methyl-1H-pyrazole-4-carboxamide, mp=144°–145° C.

Analysis calculated for $C_{11}H_9BrFN_3O$ Theory: C, 44.32; H, 3.04; N, 14.10; Found: C, 44.54; H, 2.94; N, 13.93.

EXAMPLE 32

5-Chloro-1-(2,4,5-trichlorophenyl)-N-methyl-1H-pyrazole-4-carboxamide, mp=193°–195° C.

Analysis calculated for $C_{11}H_7Cl_4N_3O$ Theory: C, 38.97; H, 2.08; N, 12.39; Found: C, 39.18; H, 1.82; N, 12.14.

EXAMPLE 33

5-Chloro-1-(2,4,6-tribromophenyl)-N-methyl-1H-pyrazole-4-carboxamide, mp=183°–185° C.

Analysis calculated for $C_{11}H_7Br_3ClN_3O$ Theory: C, 27.97; H, 1.49; N, 8.90; Found: C, 28.57; H, 1.67; N, 9.06.

EXAMPLE 34

5-Chloro-1-(3-fluorophenyl)-N-ethyl-1H-pyrazole-4-carboxamide, mp=122°–123° C.

Analysis calculated for $C_{12}H_{11}ClFN_3O$ Theory: C, 53.84; H, 4.14; N, 15.70; Found: C, 53.63; H, 4.09; N, 15.80.

EXAMPLE 35

5-Chloro-1-(3-fluorophenyl)-N,N-dimethyl-1H-pyrazole-4-carboxamide, mp=122°–123° C.

Analysis calculated for $C_{12}H_{11}ClFN_3O$ Theory: C, 53.84; H, 4.14; N, 15.70; Found: C, 53.66; H, 4.16; N, 15.81.

EXAMPLE 36

5-Chloro-1-(3-fluorophenyl)-N-methyl-1H-pyrazole-4-carboxamide, mp=163°–165° C.

Analysis calculated for $C_{11}H_9ClFN_3O$ Theory: C, 52.08; H, 3.58; N, 16.57; Found: C, 51.81; H, 3.40; N, 16.47.

EXAMPLE 37

5-Chloro-1-(4-nitrophenyl)-N-methyl-1H-pyrazole-4-carboxamide, mp=165°–167° C.

Analysis calculated for $C_{11}H_9ClN_4O_3$ Theory: C, 47.07; H, 3.23; N, 19.96; Found: C, 47.33; H, 3.31; N, 19.95.

EXAMPLE 38

5-Chloro-1-(4-nitrophenyl)-N,N-dimethyl-1H-pyrazole-4-carboxamide, mp=149°–152° C.

Analysis calculated for $C_{12}H_{11}ClN_4O_3$ Theory: C, 48.91; H, 3.76; N, 19.01; Found: C, 49.18; H, 4.01; N, 18.85.

EXAMPLE 39

5-Bromo-1-(4-nitrophenyl)-N-methyl-1H-pyrazole-4-carboxamide, mp=172°–175° C.

Analysis calculated for $C_{11}H_9BrN_4O_3$ Theory: C, 40.64; H, 2.79; N, 17.23; Found: C, 40.88; H, 2.72; N, 17.19.

EXAMPLE 40

5-Bromo-1-(3-chlorophenyl)-N-methyl-1H-pyrazole-4-carboxamide, mp=124°–125° C.

Analysis calculated for $C_{11}H_9BrClN_3O$ Theory: C, 42.00; H, 2.88; N, 13.36; Cl, 11.27; Br, 25.40; Found: C, 41.72; H, 3.00; N, 13.11; Cl, 11.06; Br, 25.26.

EXAMPLE 41

5-Chloro-1-(3-chlorophenyl)-N-methoxy-1H-pyrazole-4-carboxamide, mp=74°–76° C.

Analysis calculated for $C_{11}H_9Cl_2N_3O_2$ Theory: C, 46.18; H, 3.17; N, 14.69; Found: C, 46.08; H, 3.26; N, 14.47.

EXAMPLE 42

5-Chloro-1-(2,5-dichlorophenyl)-N-methyl-1H-pyrazole-4-carboxamide, mp=166°–168° C. P Analysis calculated for $C_{11}H_8Cl_3N_3O$ Theory: C, 43.38, H, 2.65; N, 13.80; Found: C, 43.61; H, 2.62; N, 14.01.

EXAMPLE 43

5-Bromo-1-(3-chlorophenyl)-N,N-dimethyl-1H-pyrazole-4-carboxamide, mp=82°–84° C.

Analysis calculated for $C_{12}H_{11}BrClN_3O$ Theory: C, 43.86; H, 3.37; N, 12.79; Cl, 10.79; Br, 24.32; Found: C, 43.56; H, 3.35; N, 12.52; Cl, 10.82; Br, 24.35.

EXAMPLE 44

5-Chloro-1-(3-chlorophenyl)-N,N-dimethyl-1H-pyrazole-4-carboxamide, mp=101°–103° C.

Analysis calculated for $C_{12}H_{11}Cl_2N_3O$ Theory: C, 57.72; H, 3.90; N, 14.71; Found: C, 57.70; H, 3.68; N, 14.81.

EXAMPLE 45

5-Bromo-1-(3-methoxyphenyl)-N-methyl-1H-pyrazole-4-carboxamide, mp=159°–160° C.

Analysis calculated for $C_{12}H_{12}BrN_3O_2$ Theory: C, 46.47; H, 3.90; N, 13.55; Found: C, 46.63; H, 3.88; N, 13.56.

EXAMPLE 46

5-Bromo-1-(2,4-difluorophenyl)-N-methyl-1H-pyrazole-4-carboxamide, mp=129°–130° C.

Analysis calculated for $C_{11}H_8BrF_2N_3O$ Theory: C, 41.80; H, 2.55; N, 13.29; Found: C, 41.91; H, 2.68; N, 13.22.

EXAMPLE 47

5-Chloro-1-(4-fluorophenyl)-N-methyl-1H-pyrazole-4-carboxamide, mp=157°–159° C.

Analysis calculated for $C_{11}H_9ClFN_3O$ Theory: C, 52.08; H, 3.58; N, 16.57; Cl, 13.98; Found: C, 51.79; H, 3.50; N, 16.75; Cl, 14.01.

EXAMPLE 48

5-Chloro-1-(4-fluorophenyl)-N-methyl-1H-pyrazole-4-thiocarboxamide, mp=157°–159° C.

Analysis calculated for $C_{11}H_9ClFN_3S$ Theory: C, 48.98; H, 3.36; N, 15.58; S, 11.89; Found: C, 49.21; H, 3.31; N, 15.45; S, 11.67.

EXAMPLE 49

5-Chloro-1-(4-fluorophenyl)-N,N-dimethyl-1H-pyrazole-4-carboxamide, mp=139°–141° C.

Analysis calculated for $C_{12}H_{11}ClFN_3O$ Theory: C, 53.84; H, 4.14; N, 15.70; Cl, 13.24; Found: C, 53.79; H, 4.10; N, 15.88; Cl, 13.49.

EXAMPLE 50

5-Chloro-1-(4-fluorophenyl)-N-ethyl-1H-pyrazole-4-carboxamide, mp=172°–174° C.

Analysis calculated for $C_{12}H_{11}ClFN_3O$ Theory: C, 53.84; H, 4.14; N, 15.70; Found: C, 54.12; H, 4.09; N, 15.75.

EXAMPLE 51

5-Chloro-1-(4-fluorophenyl)-N-methoxy-1H-pyrazole-4-carboxamide, mp=178°–180° C.

Analysis calculated for $C_{11}H_9ClFN_3O_2$ Theory: C, 48.99; H, 3.36; N, 15.58; Found: C, 48.78; H, 3.57; N, 15.77.

EXAMPLE 52

5-Bromo-1-(4-fluorophenyl)-N-methyl-1H-pyrazole-4-carboxamide, mp=177°–178° C.

Analysis calculated for $C_{11}H_9BrFN_3O$ Theory: C, 44.32; H, 3.04; N, 14.10; Found: C, 44.60; H, 3.22; N, 14.17.

EXAMPLE 53

5-Chloro-1-(3,4-dichlorophenyl)-N-methyl-1H-pyrazole-4-carboxamide, mp=118°–120° C.

Analysis calculated for $C_{11}H_8Cl_3N_3O$ Theory: C, 43.38; H, 2.65; N, 13.80; Cl, 34.92; Found: C, 43.38; H, 2.81; N, 13.55; Cl, 34.71.

EXAMPLE 54

5-Chloro-1-(3,4-dichlorophenyl)-N,N-dimethyl-1H-pyrazole-4-carboxamide, mp=128°–130° C.

Analysis calculated for $C_{12}H_{10}Cl_3N_3O$ Theory: C, 45.24; H, 3.16; N, 13.19; Cl, 33.38; Found: C, 45.49; H, 3.43; N, 13.19; Cl, 33.15.

EXAMPLE 55

5-Chloro-1-(4-bromophenyl)-N-methyl-1H-pyrazole-4-carboxamide, mp=175°–177° C.

Analysis calculated for $C_{11}H_9BrClN_3O$ Theory: C, 42.00; H, 2.88; N, 13.36; Cl, 11.27; Br, 25.40; Found: C, 42.06; H, 2.79; N, 13.11; Cl, 11.30; Br, 25.54.

EXAMPLE 56

5-Chloro-1-(4-bromophenyl)-N,N-dimethyl-1H-pyrazole-4-carboxamide, mp=111°–113° C.

Analysis calculated for $C_{12}H_{11}BrClN_3O$ Theory: C, 43.86; H, 3.37; N, 12.79; Cl, 10.79; Br, 24.32; Found: C, 43.98; H, 3.20; N, 12.83; Cl, 11.03; Br, 24.60.

EXAMPLE 57

5-Chloro-1-(4-bromophenyl)-N-ethyl-1H-pyrazole-4-carboxamide, mp=170°–172° C.

Analysis calculated for $C_{12}H_{11}BrClN_3O$ Theory: C, 43.86; H, 3.37; N, 12.79; Cl, 10.79; Br, 24.32; Found: C, 44.04; H, 3.25; N, 13.03; Cl, 10.66; Br, 24.12.

EXAMPLE 58

5-Bromo-1-(4-methylphenyl)-N-methyl-1H-pyrazole-4-carboxamide, mp=160°–162° C.

Analysis calculated for $C_{12}H_{12}BrN_3O$ Theory: C, 49.00; H, 4.11; N, 14.29; Found: C, 48.73; H, 4.17; N, 14.03.

EXAMPLE 59

5-Chloro-1-(4-methylphenyl)-N-methyl-1H-pyrazole-4-carboxamide, mp=154°–156° C.

Analysis calculated for $C_{12}H_{12}ClN_3O$ Theory: C, 57.72; H, 4.84; N, 16.83; Found: C, 57.94; H, 4.83; N, 16.59.

EXAMPLE 60

5Chloro-1-(4-methylphenyl)-N,N-dimethyl-1H-pyrazole-4-carboxamide, mp=84°–87° C.

Analysis calculated for $C_{13}H_{14}ClN_3O$ Theory: C, 59.21; H, 5.35; N, 15.93; Found: C, 59.44; H, 5.31; N, 16.13.

EXAMPLE 61

5-Methylthio-1-phenyl-N-methyl-1H-pyrazole-4-carboxamide, mp=108°–110° C.

Analysis calculated for $C_{12}H_{13}N_3OS$ Theory: C, 58.28; H, 5.30; N, 16.99; Found: C, 58.11; H, 5.44; N, 16.78.

EXAMPLE 62

5-Bromo-1-(4-chlorophenyl)-N-methyl-1H-pyrazole-4-carboxamide, mp=171°–173° C.

Analysis calculated for $C_{11}H_9BrClN_3O$ Theory: C, 42.00; H, 2.88; N, 13.36; Cl, 11.27; Br, 25.40; Found: C, 41.85; H, 2.72; N, 13.49; Cl, 11.38; Br, 25.60.

EXAMPLE 63

5-Bromo-1-(4-chlorophenyl)-N,N-dimethyl-1H-pyrazole-4-carboxamide, mp=132°–134° C.

Analysis calculated for $C_{12}H_{11}BrClN_3O$ Theory: C, 43.86; H, 3.37; N, 12.79; Cl, 10.79; Br, 24.32; Found: C, 43.64; H, 3.16; N, 12.50; Cl, 10.94; Br, 24.56.

EXAMPLE 64

5-Bromo-1-(4-methoxyphenyl)-N-methyl-1H-pyrazole-4-carboxamide, mp=166°–167° C.

Analysis calculated for $C_{12}H_{12}BrN_3O_2$ Theory: C, 46.47; H, 3.90; N, 13.55; Found: C, 46.62; H, 3.88; N, 13.41.

EXAMPLE 65

5-Methoxy-1-(3-chlorophenyl)-N-methyl-1H-pyrazole-4-carboxamide, mp=104°–105° C.

Analysis calculated for $C_{12}H_{12}ClN_3O_2$ Theory: C, 54.25; H, 4.55; N, 15.82; Found: C, 54.09; H, 4.39; N, 15.58.

EXAMPLE 66

5-Chloro-1-(4-chlorophenyl)-N-methyl-1H-pyrazole-4-carboxamide, mp=161°–163° C.

Analysis calculated for $C_{11}H_9Cl_2N_3O$ Theory: C, 48.91; H, 3.36; N, 15.56; Cl, 26.25; Found: C, 48.99; H, 3.55; N, 15.68; Cl, 26.46.

EXAMPLE 67

5-Chloro-1-(4-chlorophenyl)-N,N-dimethyl-1H-pyrazole-4-carboxamide, mp=119°–121° C.

Analysis calculated for $C_{12}H_{11}Cl_2N_3O$ Theory: C, 50.72; H, 3.90; N, 14.79; Cl, 24.95; Found: C, 50.42; H, 3.92; N, 14.68; Cl, 25.22.

EXAMPLE 68

5-Chloro-1-(4-ethylphenyl)-N-methyl-1H-pyrazole-4-carboxamide, mp=151°–153° C.

Analysis calculated for $C_{13}H_{14}ClN_3O$ Theory: C, 59.21; H, 5.35; N, 15.93; Found: C, 59.31; H, 5.19; N, 16.09.

EXAMPLE 69

5-Bromo-1-(4-ethylphenyl)-N-methyl-1H-pyrazole-4-carboxamide, mp=167°–168° C.

Analysis calculated for $C_{13}H_{14}BrN_3O$ Theory: C, 50.67; H, 4.58; N, 13.64; Found: C, 50.86; H, 4.36; N, 13.39.

EXAMPLE 70

5-Chloro-1-(2,4-dichlorophenyl)-N-methyl-1H-pyrazole-4-carboxamide, mp=153°–155° C.

Analysis calculated for $C_{11}H_8Cl_3N_3O$ Theory: C, 43.38; H, 2.65; N, 13.80; Cl, 34.92; Found: C, 43.63; H, 2.55; N, 13.67; Cl, 35.11.

EXAMPLE 71

5-Bromo-1-(2,4-dichlorophenyl)-N-methyl-1H-pyrazole-4-carboxamide, mp=153°–154° C.

Analsyis calculated for $C_{11}H_8BrCl_2N_3O$ Theory: C, 37.86; H, 2.31; N, 12.04; Found: C, 38.01; H, 2.18; N, 11.80.

EXAMPLE 72

5-Bromo-1-(2,4-dichlorophenyl)-N,N-dimethyl-1H-pyrazole-4-carboxamide, mp=88°–90° C.

Analysis calculated for $C_{12}H_{10}BrCl_2N_3O$ Theory: C, 39.70; H, 2.78; N, 11.57; Found: C, 39.49; H, 2.63; N, 11.33.

EXAMPLE 73

5-Bromo-1-(2,4-dichlorophenyl)-N-ethyl-1H-pyrazole-4-carboxamide, mp=135°–136° C.

Analysis calculated for $C_{12}H_{10}BrCl_2N_3O$ Theory: C, 39.70; H, 2.78; N, 11.57; Found: C, 39.92; H, 2.70; N, 11.51.

EXAMPLE 74

5-Chloro-1-(2,3-dichlorophenyl)-N-methyl-1H-pyrazole-4-carboxamide, mp=210°–213° C.

Analysis calculated for $C_{11}H_8Cl_3N_3O$ Theory: C, 43.38; H, 2.65; N, 13.80; Found: C, 43.31; H, 2.61; N, 13.90.

EXAMPLE 75

5-Chloro-1-(2,4,6-trichlorophenyl)-N-methyl-1H-pyrazole-4-carboxamide, mp=188°–190° C.

Analysis calculated for $C_{11}H_7Cl_4N_3O$ Theory: C, 38.97; H, 2.08; N, 12.40; Found: C, 39.24; H, 2.07; N, 12.68.

EXAMPLE 76

5-Chloro-1-(2,4-dibromophenyl)-N-methyl-1H-pyrazole-4-carboxamide, mp=159°–161° C.

Analysis calculated for $C_{11}H_8Br_2ClN_3O$ Theory: C, 33.58; H, 2.05; N, 10.68; Found: C, 33.74; H, 2.27; N, 10.70.

EXAMPLE 77

5-Chloro-1-(2,4-difluorophenyl)-N-methyl-1H-pyrazole-4-carboxamide, mp=133°–135° C.

Analsyis calculated for $C_{11}H_8ClF_2N_3O$ Theory: C, 48.64; H, 2.97; N, 15.47; Found: C, 48.55; H, 3.04; N, 15.29.

EXAMPLE 78

5-Chloro-1-(3-chloro-4-methylphenyl)-N-methyl-1H-pyrazole-4-carboxamide, mp=103°–105° C.

Analysis calculated for $C_{12}H_{11}Cl_2N_3O$ Theory: C, 50.72; H, 3.90; N, 14.79; Found: C, 50.87; H, 3.78; N, 14.64.

EXAMPLE 79

5-Bromo-1-(3-chloro-4-methylphenyl)-N-methyl-1H-pyrazole-4-carboxamide, mp=159°–160° C.

Analysis calculated for $C_{12}H_{11}BrClN_3O$ Theory: C, 43.86; H, 3.37; N, 12.79; Found: C, 44.07; H, 3.51; N, 12.51.

EXAMPLE 80

5-Bromo-1-(3,4-dichlorophenyl)-N-methyl-1H-pyrazole-4-carboxamide, mp=149°–151° C.

Analysis calculated for $C_{11}H_8BrCl_2N_3O$ Theory: C, 37.86; H, 2.31; N, 12.04; Found: C, 37.84; H, 2.17; N, 11.83.

EXAMPLE 81

5-Methoxy-1-[3-(trifluoromethyl)phenyl]-N-methyl-1H-pyrazole-4-carboxamide, mp=128°–130° C.

Analysis calculated for $C_{13}H_{12}F_3N_3O_2$ Theory: C, 52.18; H, 4.04; N, 14.04; Found: C, 52.41; H, 3.76; N, 13.83.

EXAMPLE 82

5-Bromo-1-(3-fluorophenyl)-N-cyclopropyl-1H-pyrazole-4-carboxamide, mp=144°–146° C.

Analysis calculated for $C_{13}H_{11}BrFN_3O$ Theory: C, 48.17; H, 3.42; N, 12.96; Found: C, 47.96; H, 3.19; N, 12.68.

EXAMPLE 83

5-Bromo-1-(3,5-dichlorophenyl)-N-cyclopropyl-1H-pyrazole-4-carboxamide, mp=184°–185° C.

Analysis calculated for $C_{13}H_{10}BrCl_2N_3O$ Theory: C, 41.63; H, 2.69; N, 11.20; Found: C, 41.82; H, 2.79; N, 11.27.

EXAMPLE 84

5-Chloro-1-[3-(trifluoromethyl)phenyl]-N-cyclopropyl-1H-pyrazole-4-carboxamide, mp=121°–122° C.

Analysis calculated for $C_{14}H_{11}ClF_3N_3O$ Theory: C, 51.00; H, 3.36; N, 12.74; Found: C, 51.29; H, 3.33; N, 12.79.

EXAMPLE 85

5-Chloro-1-phenyl-N-cyclopropyl-1H-pyrazole-4-carboxamide, mp=154°–155° C.

Analysis calculated for $C_{13}H_{12}ClN_3O$ Theory: C, 59.66; H, 4.62; N, 16.06; Found: C, 59.91; H, 4.40; N, 16.29.

EXAMPLE 86

5-Bromo-1-(2,4-dichlorophenyl)-N-cyclopropyl-1H-pyrazole-4-carboxamide, mp=158°–159° C.

Analysis calculated for $C_{13}H_{10}BrCl_2N_3O$ Theory: C, 41.63; H, 2.69; N, 11.20; Found: C, 41.67; H, 2.42; N, 11.42.

EXAMPLE 87

5-Chloro-1-(4-chlorophenyl)-N-cyclopropyl-1H-pyrazole-4-carboxamide, mp=186°–188° C.

Analysis calculated for $C_{13}H_{11}Cl_2N_3O$ Theory: C, 52.72; H, 3.74; N, 14.19; Found: C, 52.88; H, 3.89; N, 14.22.

EXAMPLE 88

5-Chloro-1-(2,4-difluorophenyl)-N-cyclopropyl-1H-pyrazole-4-carboxamide, mp=141°–143° C.

Analysis calculated for $C_{13}H_{10}ClF_2N_3O$ Theory: C, 52.45; H, 3.39; N, 14.12; Found: C, 52.66; H, 3.19; N, 13.94.

EXAMPLE 89

5-Chloro-1-(3-chlorophenyl)-N-cyclopropyl-1H-pyrazole-4-carboxamide, mp=104°–106° C.

Analysis calculated for $C_{13}H_{11}Cl_2N_3O$ Theory: C, 52.72; H, 3.74; N, 14.19; Found: C, 52.91; H, 3.59; N, 14.23.

EXAMPLE 90

5-Chloro-1-(3-bromophenyl)-N-cyclopropyl-1H-pyrazole-4-carboxamide, mp=108° C.

Analysis calculated for $C_{13}H_{11}BrClN_3O$ Theory: C, 45.84; H, 3.26; N, 12.34; Found: C, 46.09; H, 3.22; N, 12.18.

EXAMPLE 91

5-Chloro-1-(2,4-dichlorophenyl)-N-cyclopropyl-1H-pyrazole-4-carboxamide, mp=158°–160° C.

Analysis calculated for $C_{13}H_{10}Cl_3N_3O$ Theory: C, 47.23; H, 3.05; N, 12.71; Found: C, 47.13; H, 2.86; N, 12.63.

EXAMPLE 92

5-Chloro-1-(2-pyridinyl)-N-methyl-1H-pyrazole-4-carboxamide, mp=133°–135° C.

Analysis calculated for $C_{10}H_9ClN_4O$ Theory: C, 50.75; H, 3.83; N, 23.67; Found: C, 50.71; H, 3.57; N, 23.45.

EXAMPLE 93

5-Chloro-1-(3,4-dimethylphenyl)-N-cyclopropyl-1H-pyrazole-4-carboxamide, mp=142°–144° C.

Analysis calculated for $C_{15}H_{16}ClN_3O$ Theory: C, 62.18; H, 5.57; N, 14.50; Found: C, 61.88; H, 5.47; N, 14.46.

EXAMPLE 94

5-Chloro-1-methyl-N-cyclopropyl-1H-pyrazole-4-carboxamide

A. 5-Amino-1-methyl-1H-pyrazole-4-carboxylic acid, ethyl ester

Methylhydrazine (25 grams, 0.54 mole) and ethyl(ethoxymethylene)cyanoacetate (92 grams, 0.54 mole) were combined in 150 ml. of ethanol and refluxed for about 16 hours. The reaction mixture was then cooled and poured over ice water, and the resulting precipitated product was collected by filtration and dried. The mother liquor was extracted with chloroform, washed with saturated brine, and dried using sodium sulfate and filter paper. Solvent was removed in vacuo. Both groups of crystallized product were recrystallized from ethanol, yielding 32.3 grams (35%) of 5-amino-1-methyl-1H-pyrazole-4-carboxylic acid, ethyl ester, mp=99°–100° C.

B. 5-Chloro-1-methyl-1H-pyrazole-4-carboxylic acid, ethyl ester

For a period of 60 minutes, hydrogen chloride gas was bubbled into a solution of 5-amino-1-methyl-1H-pyrazole-4-carboxylic acid, ethyl ester (12 grams, 0.07 mole) in 75 ml. of chloroform. The reaction mixture set up and nitrosyl chloride was bubbled into the reaction mixture for a period of five minutes. TLC indicated that starting material was still present, therefore, nitrosyl chloride was bubbled into the reaction mixture for an additional five minutes. The solution was heated on a steam bath for five minutes, then cooled and the solvent removed in vacuo, yielding 5-chloro-1-methyl-1H-pyrazole-4-carboxylic acid, ethyl ester. The identity of the product was confirmed by NMR.

C. 5-Chloro-1-methyl-1H-pyrazole-4-carboxylic acid

5-Chloro-1-methyl-1H-pyrazole-4-carboxylic acid, ethyl ester (13 grams, 0.07 mole) and potassium hydroxide (7.8 grams, 0.14 mole) were combined in 75 ml. of ethanol and refluxed for six hours. The solution was cooled, poured over water, acidified with concentrated hydrochloric acid, and the precipitated solid collected, dried, and recrystallized from water. The resulting 5-chloro-1-methyl-1H-pyrazole-4-carboxylic acid was obtained in the amount of 5.4 grams and melted at 195°–197° C.

Analysis calculated for $C_5H_5ClN_2O_2$ Theory: C, 37.53; H, 3.15; N, 17.15; Found: C, 37.68; H, 3.06; N, 17.69.

D. 5-Chloro-1-methyl-N-cyclopropyl-1H-pyrazole-4-carboxamide

Carbonyldiimidazole (3.6 grams, 0.022 mole) was added to a solution of 5-chloro-1-methyl-1H-pyrazole-4-carboxylic acid (2.4 grams, 0.015 mole) in 40 ml. of tetrahydrofuran, and the solution was stirred at room temperature for twenty minutes. Cyclopropylamine (1.3 grams, 0.022 mole) was then added and the reaction mixture was stirred at room temperature for sixteen hours. Solvent was removed in vacuo and the residue was taken up in 250 ml. of chloroform, washed with water, washed with saturated brine, and dried using sodium sulfate and filter paper. The product was recrystallized from toluene, yielding 3.5 grams of 5-chloro-1-methyl-N-cyclopropyl-1H-pyrazole-4-carboxamide, mp=105°–107° C.

Analysis calculated for $C_8H_{10}ClN_3O$ Theory: C, 48.13; H, 5.05; N, 21.05; Found: C, 48.38; H, 5.01; N, 20.90.

The following other 1-alkyl compounds of the present invention were prepared in the same procedures as reported in Example 94.

EXAMPLE 95

5-Bromo-1-tert-butyl-N-methyl-1H-pyrazole-4-carboxamide, mp=128°–130° C.

Analysis calculated for $C_9H_{14}BrN_3O$ Theory: C, 41.57; H, 5.43; N, 16.16; Found: C, 41.67; H, 5.49; N, 16.14.

EXAMPLE 96

5-Bromo-1-tert-butyl-N,N-dimethyl-1H-pyrazole-4-carboxamide, mp=87°–90° C.

Analysis calculated for $C_{10}H_{16}BrN_3O$ Theory: C, 43.81; H, 5.88; N, 15.33; Found: C, 43.76; H, 5.71; N, 15.56.

EXAMPLE 97

5-Bromo-1-tert-butyl-N-cyclopropyl-1H-pyrazole-4-carboxamide, mp=148°–150° C.

Analysis calculated for $C_{11}H_{16}BrN_3O$ Theory: C, 46.17; H, 5.64; N, 14.68; Found: C, 45.96; H, 5.63; N, 14.45.

EXAMPLE 98

5-Bromo-1-tert-butyl-N-ethyl-1H-pyrazole-4-carboxamide, mp=93°–95° C.

Analysis calculated for $C_{10}H_{16}BrN_3O$ Theory: C, 43.81; H, 5.88; N, 15.33; Found: C, 43.94; H, 5.87; N, 15.17.

EXAMPLE 99

5-Bromo-1-tert-butyl-N-isopropyl-1H-pyrazole-4-carboxamide, mp 108°–110° C.

Analysis calculated for $C_{11}H_{18}BrN_3O$ Theory: C, 45.85; H, 6.30; N, 14.58; Found: C, 46.13; H, 6.65; N, 14.63.

EXAMPLE 100

5-Bromo-1-tert-butyl-N-methyl-N-ethyl-1H-pyrazole-4-carboxamide, mp=98°–100° C.

Analysis calculated for $C_{11}H_{18}BrN_3O$ Theory: C, 45.85; H, 6.30; N, 14.58; Found: C, 45.85; H, 6.43; N, 14.56.

EXAMPLE 101

5-Bromo-1-tert-butyl-N-methyl-N-methoxy-1H-pyrazole-4-carboxamide, mp=71°–74° C.

Analysis calculated for $C_{10}H_{16}BrN_3O_2$ Theory: C, 41.39; H, 5.56; N, 14.48; Found: C, 41.62; H, 5.66; N, 14.71.

EXAMPLE 102

5-Chloro-1-tert-butyl-N-methyl-1H-pyrazole-4-carboxamide, mp=154°–156° C.

Analysis calculated for $C_9H_{14}ClN_3O$ Theory: C, 50.12; H, 6.54; N, 19.48; Found: C, 50.10; H, 6.36; N, 19.45.

EXAMPLE 103

5-Chloro-1-tert-butyl-N-cyclopropyl-1H-pyrazole-4-carboxamide, mp=168°–171° C.

Analysis calculated for $C_{11}H_{16}ClN_3O$ Theory: C, 54.64; H, 6.67; N, 17.38; Found: C, 54.84; H, 6.92; N, 17.35.

EXAMPLE 104

5-Chloro-1-tert-butyl-N,N-dimethyl-1H-pyrazole-4-carboxamide, oil

Analysis calculated for $C_{10}H_{16}ClN_3O$ Theory: C, 52.29; H, 7.02; N, 18.29; Found: C, 52.53; H, 7.12; N, 18.40.

EXAMPLE 105

5-Chloro-1-tert-butyl-N-methyl-N-methoxy-1H-pyrazole-4-carboxamide, oil

Analysis calculated for $C_{10}H_{16}ClN_3O_2$ Theory: C, 48.88; H, 6.56; N, 17.10; Found: C, 48.66; H, 6.61; N, 17.26.

EXAMPLE 106

5-Chloro-tert-butyl-N-ethyl-1H-pyrazole-4-carboxamide, mp=109°–110° C.

Analysis calculated for $C_{10}H_{16}ClN_3O$ Theory: C, 52.29; H, 7.02; N, 18.29; Found: C, 52.44; H, 7.22; N, 18.38.

EXAMPLE 107

5-Chloro-1-tert-butyl-N-methyl-N-ethyl-1H-pyrazole-4-carboxamide, mp=71°-73° C.

Analysis calculated for $C_{11}H_{18}ClN_3O$ Theory: C, 54.37; H, 7.47; N, 17.29; Found: C, 54.02; H, 7.65; N, 17.01.

EXAMPLE 108

5-Chloro-1-tert-butyl-N,N-diethyl-1H-pyrazole-4-carboxamide, oil

Analysis calculated for $C_{12}H_{20}ClN_3O$ Theory: C, 55.92; H, 7.82; N, 16.30; Found: C, 55.79; H, 7.66; N, 16.53.

EXAMPLE 109

5-(Trifluoromethyl)-1-(2,4-dichlorophenyl)-N-methyl-1H-pyrazole-4-carboxamide

A. 5-(Trifluoromethyl)-1-(2,4-dichlorophenyl)-1H-pyrazole-4-carboxylic acid, ethyl ester 2,4-Dichlorophenylhydrazine hydrochloride salt (15.68 grams, 0.068 mole) was dissolved in a minimum amount of ethanol and the solution was cooled to −10° C. Triethylamine (9.44 ml., 0.068 mole) was added followed by ethyl (ethoxymethylene)trifluoroacetoacetate (16.27 grams, 0.068 mole). The addition of this last reactant was made over thirty minutes, keeping the reaction temperature below −10° C. The reaction mixture was allowed to rise to room temperature overnight (about 16 hours). The solvent was removed in vacuo and the residue was dissolved in equal parts of ethyl acetate and water. The organic phase was separated, washed with 1N HCl, water, saturated sodium bicarbonate solution, water, and brine. It was then dried and evaporated to 7.85 grams of an oil which slowly crystallized. The 5-(trifluoromethyl)-1-(2,4-dichlorophenyl)-1H-pyrazole-4-carboxylic acid, ethyl ester, was recrystallized from petroleum ether, mp=81°-83° C.

B. 5-(Trifluoromethyl)-1-(2,4-dichlorophenyl)-1H-pyrazole-4-carboxylic acid 5-(Trifluoromethyl)-1-(2,4-dichlorophenyl)-1H-pyrazole-4-carboxylic acid ethyl ester (3.31 grams, 0.0094 mole) and potassium hydroxide (0.8 gram, 0.014 mole) were combined in 25 ml. of ethanol. The reaction mixture was refluxed for 2 hours, then poured into 150 ml. of ice/water and filtered to remove solids. The remaining solution was acidified with concentrated HCl, filtered to separate the precipitate which was then dried and recrystallized from cyclohexane/toluene with charcoal, yielding 1.90 grams of 5-(trifluoromethyl)-1-(2,4-dichlorophenyl)-1H-pyrazole-4-carboxylic acid, mp=154°-155° C.

Analysis calculated for $C_{11}H_5Cl_2F_3N_2O_2$ Theory: C, 40.64; H, 1.55; N, 8.62; Found: C, 40.85; H, 1.79; N, 8.41.

C. 5-(Trifluoromethyl)-1-(2,4-dichlorophenyl)-N-methyl-1H-pyrazole-4-carboxamide 5-(Trifluoromethyl)-1-(2,4-dichlorophenyl)-1H-pyrazole-4-carboxylic acid (1.50 grams, 0.0046 mole) and carbonyldiimidazole (0.94 gram, 0.0058 mole) were dissolved in DMF. The reaction mixture was stirred for 10 minutes, then 7 ml. of 40% aqueous methylamine were added. The reaction mixture was stirred for three hours at room temperature, then poured into 150 ml. of water and filtered. The precipitate was dried to 1.51 grams, then recrystallized from 10:1 cyclohexane/toluene, yielding 1.23 grams of 5-(trifluoromethyl)-1-(2,4-dichlorophenyl)-N-methyl-1H-pyrazole-4-carboxamide, mp=143°-144° C.

Analysis calculated for $C_{12}H_8Cl_2F_3N_3O$ Theory: C, 42.63; H, 2.38; N, 12.43; Found: C, 42.63; H, 2.44; N, 12.21.

The following other 5-(trifluoromethyl) compounds of the present invention were prepared in the same procedures as in Example 109.

EXAMPLE 110

5-(Trifluoromethyl)-1-(2,4-dichlorophenyl)-N-cyclopropyl-1H-pyrazole-4-carboxamide, mp=132°-133° C.

Analysis calculated for $C_{14}H_{10}Cl_2F_3N_3O$
Therory: C, 46.18; H, 2.77; N, 11.54;
Found: C, 46.13; H, 2.99; N, 11.29.

EXAMPLE 111

5-(Trifluoromethyl)-1-(2,4-dichlorophenyl)-N,N-dimethyl-1H-pyrazole-4-carboxamide, mp=120°-122° C.

Analysis calculated for $C_{13}H_{10}Cl_2F_3N_3O$ Theory: C, 44.34; H, 2.86; N, 11.93; Found: C, 44.17; H, 2.66; N, 11.96.

EXAMPLE 112

5-(Trifluoromethyl)-1-(4-chlorophenyl)-N-methyl-1H-pyrazole-4-carboxamide, mp=156°-157° C.

Analysis calculated for $C_{12}H_9ClF_3N_3O$ Theory: C, 47.46; H, 2.99; N, 13.84; Found: C, 47.42; H, 3.09; N, 13.76.

EXAMPLE 113

5-(Trifluoromethyl)-1-(4-chlorophenyl)-N-cyclopropyl-1H-pyrazole-4-carboxamide, mp=164°-165° C.

Analysis calculated for $C_{14}H_{11}ClF_3N_3O$ Theory: C, 51.00; H, 3.36; N, 12.74; Found: C, 51.20; H, 3.11; N, 12.69.

EXAMPLE 114

5-(Trifluoromethyl)-1-(4-chlorophenyl)-N,N-dimethyl-1H-pyrazole-4-carboxamide, mp=117°-119° C.

Analysis calculated for $C_{13}H_{11}ClF_3N_3O$ Theory: C, 49.15; H, 3.49; N, 13.23; Found: C, 48.98; H, 3.70; N, 13.10.

EXAMPLE 115

5-(Trifluoromethyl)-1-(4-chlorophenyl)-N-ethyl-1H-pyrazole-4-carboxamide, mp=131°-133° C.

Analysis calculated for $C_{13}H_{11}ClF_3N_3O$ Theory: C, 49.15; H, 3.49; N, 13.23; Found: C, 48.96; H, 3.23; N, 13.16.

EXAMPLE 116

5-(Trifluoromethyl)-1-(4-chlorophenyl)-N,N-diethyl-1H-pyrazole-4-carboxamide, mp=66°-67° C.

Analysis calculated for $C_{15}H_{15}ClF_3N_3O$ Theory: C, 52.11; H, 4.37; N, 12.15; Found: C, 52.37; H, 4.36; N, 12.18.

EXAMPLE 117

5-(Trifluoromethyl)-1-(4-chlorophenyl)-N-methyl-N-methoxy-1H-pyrazole-4-carboxamide, mp=76°-78° C.

Analysis calculated for $C_{13}H_{11}ClF_3N_3O_2$ Theory: C, 46.79; H, 3.32; N, 12.59; Found: C, 46.82; H, 3.09; N, 12.60.

EXAMPLE 118

5-(Trifluoromethyl)-1-phenyl-N-methyl-1H-pyrazole-4-carboxamide, mp=152°-154° C.

Analysis calculated for $C_{12}H_{10}F_3N_3O$ Theory: C, 53.54; H, 3.74; N, 15.61; Found: C, 53.71; H, 3.65; N, 15.84.

EXAMPLE 119

5-(Trifluoromethyl)-1-phenyl-N-cyclopropyl-1H-pyrazole-4-carboxamide, mp32 135°-138° C.

Analysis calculated for $C_{14}H_{12}F_3N_3O$ Theory: C, 56.95; H, 4.10; N, 14.23; Found: C, 56.66; H, 4.14; N, 14.25.

EXAMPLE 120

5-(Trifluoromethyl)-1-phenyl-N-isopropyl-1H-pyrazole-4-carboxamide, mp=136°-137° C.

Analysis calculated for $C_{14}H_{14}F_3N_3O$ Theory: C, 56.56; H, 4.75; N, 14.13; Found: C, 56.79; H, 4.53; N, 14.32.

EXAMPLE 121

5-(Trifluoromethyl)-1-phenyl-N-methyl-N-ethyl-1H-pyrazole-4-carboxamide

Analysis calculated for $C_{14}H_{14}F_3N_3O$ Theory: C, 56.56; H, 4.75; N, 14.13; Found: C, 56.33; H, 4.63; N, 14.06.

EXAMPLE 122

5-(Trifluoromethyl)-1-phenyl-N,N-dimethyl-1H-pyrazole-4-carboxamide, mp=102°-104° C.

Analysis calculated for $C_{13}H_{12}F_3N_3O$ O Theory: C, 55.13; H, 4.27; N, 14.83; Found: C, 55.07; H, 4.49; N, 14.91.

EXAMPLE 123

5-(Trifluoromethyl)-1-phenyl-N-ethyl-1H-pyrazole-4-carboxamide, mp=117°-118° C.

Analysis calculated for $C_{13}H_{12}F_3N_3O$ Theory: C, 55.13; H, 4.27; N, 14.83; Found: C, 55.00; H, 4.10; N, 14.68.

EXAMPLE 124

5-(Trifluoromethyl)-1-phenyl-N-propyl-1H-pyrazole-4-carboxamide, mp=80°-81° C.

Analysis calculated for $C_{14}H_{14}F_3N_3O$ Theory: C, 56.56; H, 4.75; N, 14.13; Found: C, 56.33; H, 4.90; N, 13.86.

EXAMPLE 125

5-(Trifluoromethyl)-1-phenyl-N-butyl-1H-pyrazole-4-carboxamide, mp=73°-75° C.

Analysis calculated for $C_{15}H_{16}F_3N_3O$ Theory: C, 57.87; H, 5.18; N, 13.50; Found: C, 58.06; H, 5.17; N, 13.60.

EXAMPLE 126

5-(Trifluoromethyl)-1-phenyl-N-methyl-N-methoxy-1H-pyrazole-4-carboxamide, mp=49°-51° C.

Analysis calculated for $C_{13}H_{12}F_3N_3O_2$ Theory: C, 52.18; H, 4.04; N, 14.04; Found: C, 52.40; H, 3.79; H, 14.13.

EXAMPLE 127

5-(Trifluoromethyl)-1-phenyl-1H-pyrazole-4-carboxamide, mp=179°-180° C.

Analysis calculated for $C_{11}H_8F_3N_3O$ Theory: C, 51.77; H, 3.16; N, 16.47; Found: C, 51.54; H, 3.31; N, 16.37.

EXAMPLE 128

5-(Trifluoromethyl)-1-phenyl-N,N-diethyl-1H-pyrazole-4-carboxamide, oil

Analysis calculated for $C_{15}H_{16}F_3N_3O$ Theory: C, 57.87; H, 5.18; N, 13.50; Found: C, 57.63; H, 5.20; N, 13.49.

EXAMPLE 129

5-(Trifluoromethyl)-1-phenyl-N,N-dipropyl-1H-pyrazole-4-carboxamide, mp=96°-98° C.

Analysis calculated for $C_{17}H_{20}F_3N_3O$ Theory: C, 60.17; H, 5.94; N, 12.38; Found: C, 59.89; H, 5.69; N, 12.64.

EXAMPLE 130

5-(Trifluoromethyl)-1-(3-chlorophenyl)-N-methyl-1H-pyrazole-4-carboxamide, mp=114° C.

Analysis calculated for $C_{12}H_9ClF_3N_3O$ Theory: C, 47.46; H, 2.99; N, 13.84; Found: C, 47.35; H, 2.74; N, 13.81.

EXAMPLE 131

5-(Trifluoromethyl)-1-(3-chlorophenyl)-N-cyclopropyl-1H-pyrazole-4-carboxamide, mp=99°-100° C.

Analysis calculated for $C_{14}H_{11}ClF_3N_3O$ Theory: C, 51.00; H, 3.36; N, 12.74; Found: C, 50.90; H, 3.28; N, 12.58.

EXAMPLE 132

5-(Trifluoromethyl)-1-(3-chlorophenyl)-N-ethyl-1H-pyrazole-4-carboxamide, mp=87°-89° C.

Analysis calculated for $C_{13}H_{11}ClF_3N_3O$ Theory: C, 49.15; H, 3.49; N, 13.23 Found: C, 49.26; H, 3.25; N, 13.16.

EXAMPLE 133

5-(Trifluoromethyl)-1-(3-chlorophenyl)-N,N-diethyl-1H-pyrazole-4-carboxamide, oil Analysis calculated for $C_{15}H_{15}ClF_3N_3O$ Theory: C, 52.11; H, 4.37; N, 12.15; Found: C, 51.91; H, 4.53; N, 11.88.

EXAMPLE 134

5-(Trifluoromethyl)-1-(3-chlorophenyl)-N-methyl-N-methoxy-1H-pyrazole-4-carboxamide, oil Analysis calculated for $C_{13}H_{11}ClF_3N_3O$ Theory: C, 46.79; H, 3.32; N, 12.59; Found: C, 46.55; H, 3.33; N, 12.37.

EXAMPLE 135

5-(Trifluoromethyl)-1-(4-methoxyphenyl)-N-methyl-1H-pyrazole-4-carboxamide

Analysis calculated for $C_{13}H_{12}F_3N_3O_2$ Theory: C, 52.18; H, 4.04; N, 14.04; Found: C, 52.05; H, 3.77; N, 13.95.

EXAMPLE 136

5-(Trifluoromethyl)-1-(4-methoxyphenyl)-N-cyclopropyl-1H-pyrazole-4-carboxamide, mp=156°-158° C.

Analysis calculated for $C_{15}H_{14}F_3N_3O_2$ Theory: C, 55.39; H, 4.34; N, 12.92; Found: C, 55.35; H, 4.24; N, 13.03.

EXAMPLE 137

5-(Trifluoromethyl)-1-(4-methoxyphenyl)-N-ethyl-1H-pyrazole-4-carboxamide, mp=151°-152° C.

Analysis calculated for $C_{14}H_{14}F_3N_3O_2$ Theory: C, 53.68; H, 4.50; N, 13.41; Found: C, 53.69; H, 4.76; N, 13.48.

EXAMPLE 138

5-(Trifluoromethyl)-1-(4-methoxyphenyl)-N,N-dimethyl-1H-pyrazole-4-carboxamide, mp=136° C.

Analysis calculated for $C_{14}H_{14}F_3N_3O_2$ Theory: C, 53.68; H, 4.50; N, 13.41; Found: C, 53.45; H, 4.74; N, 13.33.

EXAMPLE 139

5-(Trifluoromethyl)-1-(4-methoxyphenyl)-N-methyl-N-methoxy-1H-pyrazole-4-carboxamide, mp=54°–56° C.

Analysis calculated for $C_{14}H_{14}F_3N_3O_2$ Theory: C, 51.07; H, 4.27; N, 12.76; Found: C, 51.21; H, 4.46; N, 13.92.

EXAMPLE 140

5-(Trifluoromethyl)-1-(4-methylphenyl)-N-methyl-1H-pyrazole-4-carboxamide, mp=180°–182° C.

Analysis calculated for $C_{13}H_{12}F_3N_3O$ Theory: C, 55.13; H, 4.27; N, 14.83; Found: C, 55.28; H, 4.11; N, 14.66.

EXAMPLE 141

5-(Trifluoromethyl)-1-(4-methylphenyl)-N-cyclopropyl-1H-pyrazole-4-carboxamide, mp=165°–167° C.

Analysis calculated for $C_{15}H_{14}F_3N_3O$ Theory: C, 58.25; H, 4.56; N, 13.59; Found: C, 58.52; H, 4.47; N, 13.78.

EXAMPLE 142

5-(Trifluoromethyl)-1-(4-methylphenyl)-N-ethyl-1H-pyrazole-4-carboxamide, mp=144°–145° C.

Analysis calculated for $C_{14}H_{14}F_3N_3O$ Theory: C, 56.56; H, 4.75; N, 14.13; Found: C, 56.78; H, 4.87; N, 14.09.

EXAMPLE 143

5-(Trifluoromethyl)-1-(4-methylphenyl)-N,N-diethyl-1H-pyrazole-4-carboxamide, mp=75°–76° C.

Analysis calculated for $C_{16}H_{18}F_3N_3O$ Theory: C, 59.07; H, 5.58; N, 12.92; Found: C, 59.34; H, 5.74; N, 12.84.

EXAMPLE 144

5-(Trifluoromethyl)-1-(4-methylphenyl)-N-methyl-N-methoxy-1H-pyrazole-4-carboxamide, mp=66°–68° C.

Analysis calculated for $C_{14}H_{14}F_3N_3O_2$ Theory: C, 53.68; H, 4.50; N, 13.41; Found: C, 53.95; H, 4.34; N, 13.70.

EXAMPLE 145

5-(Trifluoromethyl)-1-(3-(trifluoromethyl)-phenyl)-N-methyl-1H-pyrazole-4-carboxamide, mp=123°–124° C.

Analysis calculated for $C_{13}H_9F_6N_3O$ Theory: C, 46.30; H, 2.69; N, 12.46; Found: C, 46.31; H, 2.76; N, 12.32.

EXAMPLE 146

5-(Trifluoromethyl)-1-(3-(trifluoromethyl)-phenyl)-N-cyclopropyl-1H-pyrazole-4-carboxamide, mp=101°–102° C.

Analysis calculated for $C_{15}H_{11}F_6N_3O$ Theory: C, 49.60; H, 3.05; N, 11.57; Found: C, 49.69; H, 3.23; N, 11.45.

EXAMPLE 147

5-(Trifluoromethyl)-1-(3-(trifluoromethyl)-phenyl)-N,N-diethyl-1H-pyrazole-4-carboxamide, mp=86° C.

Analysis calculated for $C_{16}H_{15}F_6N_3O$ Theory: C, 50.67; H, 3.99; N, 11.08; Found: C, 50.66; H, 4.18; N, 10.92.

EXAMPLE 148

5-(Trifluoromethyl)-1-(3-trifluoromethyl)-phenyl)-N-methyl-N-methoxy-1H-pyrazole-4-carboxamide, mp=56°–57° C.

Analysis calculated for $C_{14}H_{11}F_6N_3O_2$ Theory: C, 45.79; H, 3.02; N, 11.44; Found: C, 46.05; H, 3.27; N, 11.45.

EXAMPLE 149

5-(Trifluoromethyl)-1-(2-pyridinyl)-N-methyl-1H-pyrazole-4-carboxamide, mp=140.5°–142° C.

Analysis calculated for $C_{11}H_9F_3N_4O$ Theory: C, 48.90; H, 3.36; N, 20.73; Found: C, 48.98; H, 3.42; N, 20.56.

EXAMPLE 150

5-(Trifluoromethyl)-1-(2-pyridinyl)-N-cyclopropyl-1H-pyrazole-4-carboxamide, mp=118°–119° C.

Analysis calculated for $C_{13}H_{11}F_3N_4O$ Theory: C, 52.71; H, 3.74; N, 18.91; Found: C, 52.60; H, 3.45; N, 18.88.

EXAMPLE 151

5-(Trifluoromethyl)-1-(2-pyridinyl)-N,N-dimethyl-1H-pyrazole-4-carboxamide, mp=77°–79° C.

Analysis calculated for $C_{12}H_{11}F_3N_4O$ Theory: C, 50.71; H, 3.90; N, 19.71; Found: C, 50.74; H, 3.96; N, 19.44.

EXAMPLE 152

5-(Trifluoromethyl)-1-(2,4,6-trichlorophenyl)-N-methyl-1H-pyrazole-4-carboxamide, mp=197°–198° C.

Analysis calculated for $C_{12}H_7Cl_3F_3N_3O$ Theory: C, 38.69; H, 1.89; N, 11.28; Found: C, 38.89; H, 2.00; N, 11.26.

EXAMPLE 153

5-(Trifluoromethyl)-1-(2,4,6-trichlorophenyl)-N-cyclopropyl-1H-pyrazole-4-carboxamide, mp=199°–201° C.

Analysis calculated for $C_{14}H_9Cl_3F_3N_3O$ Theory: C, 42.19; H, 2.28; N, 10.54; Found: C, 42.07; H, 2.36; N, 10.78.

EXAMPLE 154

5-(Trifluoromethyl)-1-(2,4,6-trichlorophenyl)-N,N-dimethyl-1H-pyrazole-4-carboxamide, mp=119°–120° C.

Analysis calculated for $C_{13}H_9Cl_3F_3N_3O$ Theory: C, 40.39; H, 2.35; N, 10.87; Found: C, 40.55; H, 2.14; N, 10.77.

EXAMPLE 155

5-(Trifluoromethyl)-1-(2,4,6-trichlorophenyl)-N-ethyl-1H-pyrazole-4-carboxamide, mp=179°–181° C.

Analysis calculated for $C_{13}H_9Cl_3F_3N_3O$ Theory: C, 40.39; H, 2.35; N, 10.87; Found: C, 40.47; H, 2.55; N, 10.79.

EXAMPLE 156

5-(Trifluoromethyl)-1-tert-butyl-N-methyl-1H-pyrazole-4-carboxamide, mp=78°-79° C.

Analysis calculated for $C_{10}H_{14}F_3N_3O$ Theory: C, 48.19; H, 5.66; N, 16.86; Found: C, 48.12; H, 5.38; N, 16.84.

EXAMPLE 157

5-(Trifluoromethyl)-1-tert-butyl-N-cyclopropyl-1H-pyrazole-4-carboxamide, mp=88°-90° C.

Analysis calculated for $C_{12}H_{16}F_3N_3O$ Theory: C, 52.36; H, 5.86; N, 15.26; Found: C, 52.24; H, 6.08; N, 15.27.

The compounds of the present invention are useful both as preemergent and postemergent herbicides. Therefore, yet another embodiment of the invention is a method for controlling undesired plants which comprises applying to the plants, or to the locus of the plants, a growth inhibiting amount of a present pyrazole derivative.

The compounds of the present invention display activity against a wide variety of weeds. Examples of typical weeds include, but are not limited to, the following:

Wild Oat (*Avena fatua*)
Catchweed Bedstraw (*Galium aparine*)
Scentless Mayweed (*Matricaria incdora*)
Ladysthumb (*Polygonum persicaria*)
Common Chickweed (*Stellaria media*)
Ivyleaf Speedwell (*Veronica hederaefolia*)
Blackgrass (*Alopecurus myosuroides*)
Chrysanthemum (*Chrysanthemum spp.*)
Common Purslane (*Portulaca oleracea*)
Sida (*Sida spp.*)
Bristly Starbur (*Acanthospermum hispidum*)
Goosegrass (*Eleusine indica*)
Smooth Pigweed (*Amaranthus hybridus*)
Alexandergrass (*Brachiaria plantaginea*)
Tall Morningglory (*Ipomoea purpurea*)
Common Lambsquarters (*Chenopodium album*)
Green Smartweed (*Polygonum scabrum*)
Green Foxtail (*Sertaria viridis*)
Redroot Pigweed (*Amaranthus retroflexus*)
Wild Buckwheat (*Polygonum convolvulus*)
Brazil Calalilly (*Richardia brasiliensis*)
Natal Grass (*Rhynchelytrum roseum*)
Ryegrass (*Lolium ridium*)
Kapeweed (*Cryptostemma calendula*)
Purple Loosestrife (*Lythrum salicaria*)
Wild radish (*Raphanus raphanistrum*)
Wireweed (*Polygonum aviculare*)
Henbit (*Lamium amplexicaule*)
Wild Mustard (*Brassica kaber*)
Barnyardgrass (*Echinochloa crus-galli*)
Foxtail Millet (*Setaria italica*)
Velvetleaf (*Abutilon theophrasti*)
Indian Mustard (*Brassica juncea*)
Birdseye Speedwell (*Veronica persica*)
Canada Thistle (*Cirsium arvense*)
Wild Chamomile (*Matricaria chamomilla*)
Annular Bluegrass (*Poa annua*)
Buttercup (*Ranunculus spp.*)
Field Speedwell (*Veronica agrestis*)
Field Violet (*Viola arvensis*)
Field Pennycress (*Thlaspi arvense*)
Wild Violet (*Violet tricolor*)
Shirley Poppy (*Papaver rhoeas*)
Field Poppy (*Papaver dubium*)
Foolsparsley (*Aethusa cynapium*)
Field Chickweed (*Cerastium arvense*)
Southern Sanbur (*Cenchrus echinatus*)
Large Crabgrass (*Digitaria sanguinalis*)
Cheat (*Bromus secalinus*)
Morningglory (*Ipomea spp.*)
Common Ragweed (*Ambrosia artemisiifolia*)
Common Milkweek (*Asclepias syriaca*)
Giant Foxtail (*Setaria faberi*)
Common Cocklebur (*Xanthium pensylvanicum*)
Spurred Anoda (*Anoda cristata*)
Sicklepod (*Cassia obtusifolia*)
Yellow Nutsedge (*Cyperus esculentus*)
Jimsonweed (*Datura stramonium*)
Large Crabgrass (*Digitaria sanguinalis*)
Prickly Sida (*Sida spinosa*)
Corn Gromwell (*Lithospermum arvense*)
Yellow Foxtail (*Setaria glauca*)
Tansymustard (*Descurainia pinnata*)
Pepperweed (*Lepidium spp.*)
Bromegrass (*Bromus spp.*)
Garden Spurge (*Euphorbia hirta*)
Crowfootgrass (*Dactyloctenium aegyptium*)
Florida Beggarweed (*Desmodium tortuosum*)
Spotted Spurge (*Euphorbia maculata*)
Smallflower Morningglory (*Jacquemontia tamnifolia*)
Browntop Millet (*Panicum ramosum*)
Coast Fiddleneck (*Amsinckia intermedia*)
Wild Turnip (*Brassica campestris*)
Black Mustard (*Brassica nigra*)
Shepherdspurse (*Capsella brusa-pastoris*)
Italian Ryegrass (*Lolium multiflorum*)
London Rocket (*Sisymbrium irio*)
Redmaids Rockpurslane (Calandrinia caulescens)
Common Groundsel (*Senecio vulgaris*)
Ivyleaf Morningglory (*Ipomoea hederacea*)
Fall Panicum (*Panicum dichotomiflorum*)
Powell Amaranth (*Amaranthus powellii*)
Texas Panicum (*Pancum texanum*)
Hemp Sesbania (*Sesbania exaltata*) Annual Sowthistle (*Sonchus oleraceus*)
Field Bindweed (*Convolvulus arvensis*)
Erect Knotweed (*Polygonum, erectum*)
Venice Mallow (*Hibiscus trionum*)
Zinnia (*Zinnia elegens*)
Nightshade (*Solanum spp.*)

The present compounds have also been found safe on a wide variety of desirable plant species, thereby exhibiting their unique selective capacity. Representative examples of relatively tolerant plant species, depending on the concentration of active agent employed, include the following:

Corn (*Zea mays*)
Wheat (*Triticum aestivum*)
Soybean (*Glycine max*)
Rice (*Oryza sativa*)
Barley (*Hordeum vulgare*)
Cotton (*Gossypium hirsutum*)
Sorghum (*Sorghum vulgare v. saccharatum*)
Sugarcane (*Saccharum officinarum*)
Peanut (*Arachis hypogaea*)
Pea (*Pisum sativum*)
Alfalfa (*Medicago staiva*)
Cucumber (*Cucumis sativus*)
Tomato (*Lycopersicon esculentum*)
Sugar beet (*Beta vulgaris*)
Cabbage (*Brassica oleracea capitata*)

The term "growth inhibiting amount", as defined herein, refers to an amount of a compound of the invention which either kills or stunts the growth of the weed species for which control is desired. This amount will generally be from about 0.05 to about 20.0 pounds or greater of a compound of the invention per acre (about 0.056 to about 22.4 kg/ha). The compounds are more preferably applied at rates of about 0.10 to about 8.0 pounds per acre (about 0.112 to about 8.96 kg/ha). The exact concentration of active ingredient required varies with the weed species to be controlled, type of formulation, soil type, climate conditions and the like.

The term "undesired plants", as defined herein, refers to both weeds and weed seeds which are present at the location to be treated with a compound of the invention. These compounds can be applied to the soil to selectively control undesired plants by soil contact when the weed seeds are germinating and emerging. They can also be used directly to kill emerged weeds by direct contact with the exposed portion of the weed.

The compounds of the present invention are preferably formulated with a suitable agriculturally-acceptable carrier for ease of application. Such compositions will contain from about 0.1 to about 95.0 percent by weight of the active ingredient, depending on the composition desired. Examples of typical herbicidal compositions contemplated as another aspect of the present invention include sprayable formulations, such as wettable powders, aqueous suspensions and emulsifiable concentrates; and solid compositions, such as dusts and granules.

The most convenient formulations are in the form of concentrated compositions to be applied by spraying as water dispersions or emulsions containing in the range from about 0.1 percent to about 10 percent of the active agent by weight. Water-dispersible or emulsifiable compositions may be either solids, usually known as wettable powders, or liquids, usually known as emulsifiable concentrates and aqueous suspensions.

A typical wettable powder comprises an intimate mixture of an active ingredient of the invention, an inert carrier, and surfactants. The concentration of the active agent is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed napthalenesulfonates, and the alkyl sulfates.

A typical emulsifiable concentrate comprises from about 0.1 to about 6 pounds of a compound of the invention per gallon of liquid (about 0.112 to about 6.72 kg), dissolved in a mixture of organic solvents and emulsifiers. The organic solvent is chosen with regard to its solvency and its cost. Useful solvents include the aromatics, especially the xylenes and the heavy aromatic napthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, napthalenesulfonates, and nonionic surfactants such as alkylphenol adducts of polyoxyethylene, and are used at similar percentages as for wettable powders.

An aqueous suspension, or flowable, is comprised of a finely ground suspension of the active ingredient dispersed in a water based system. This type of formulation is particularly useful for compounds with low water solubility. The concentration of active agent is usually from about 15 to 60 percent by weight. A typical aqueous suspension may comprise wetting and dispersing agents, antifreeze components, thickening or bulking agents, as well as water and the active ingredient.

Dust compositions containing a compound of the present invention usually contain from about 0.1 to about 10 percent by weight of the compound. Dusts are prepared by intimately mixing the finely grinding the active agent with an inert solid such as ground montmorillonite clay, attapulgite clay, talc, ground volcanic rock, kaolin clay, or other inert, relatively dense, inexpensive substances.

Solid, granular compositions are convenient for the application of compounds of this invention to the soil and will contain the active agent in an amount from about 0.1 to about 20 percent by weight. Granules comprise a compound of the invention dispersed on a granular inert carrier such as coarsely ground clay of from about 0.1 to about 3 mm particular size. The active ingredient is most conveniently applied to the clay by dissolving it in an inexpensive solvent, such as acetone, and applying the solution to the sized clay in an appropriate solids mixer. The solvent is then typically removed by evaporation prior to applying the granules to the application site.

When operating in accordance with the present invention, the present compounds or compositions thereof, may be applied to the site where herbicidal or algicidal control is desired by any convenient manner, e.g., by means of hand dusters or sprayers. Metering applicators can apply accurately measured quantitites of granular compositions to the locus to be treated. Other applications can be carried out with power dusters, broom sprayers, high-pressure sprayers and spray carriers. In large scale operations, dusts or low-volume sprays can be applied aerially, for example from airplanes or helicopters, to the application site. When applying the formulations described above, it is important to apply the desired concentration of active ingredient uniformly to the plants or locus to be treated.

The performance of the compounds of the present invention suggests that their preferred utilization will be as herbicides on grass crops, especially wheat, corn, and possibly sorghum. The compounds exhibit activity against both grass and broadleaf weed species, but exhibit greater activity against broadleaf species. The preferred application time is preemergent, that is, following planting of the crop but prior to its emergence.

The following examples provide an illustration of typical agriculturally-acceptable compositions comprehended by this invention.

| Wettable Powder | |
|---|---|
| Ingredient | Concentration by Weight (Percent) |
| 5-Chloro-1-(2,4-dichlorophenyl)-N—methyl-1H-pyrazole-4-carboxamide | 50.0 |
| Igepal, a nonionic wetting agent, GAF Corporation | 5.0 |
| Polyfon O, lignosulfonate dispersant, Westvaco Corporation | 5.0 |
| Zeolex 7, a precipitated hydrated silica bulking agent, J.M. Huber Corporation | 5.0 |
| Barden Clay, a kaolinite clay, J.M. Huber Corporation | 35.0 |

-continued

| Wettable Powder | |
|---|---|
| Ingredient | Concentration by Weight (Percent) |
| | 100.0 |

The ingredients are combined and finely ground to provide a free-flowing powder that can be suspended in water for convenient spray application.

| Aqueous Suspension | |
|---|---|
| Ingredient | Concentration by Weight (Percent) |
| 5-Chloro-1-(4-fluorophenyl)-N—methyl-1H-pyrazole-4-thiocarboxamide | 45.0 |
| Polyfon H, an anionic lignosulfonate wetting agent and dispersant, Westvaco Corporation | 3.0 |
| Sponto 2174, an emulsifier, Witco Chemical Corporation | 4.0 |
| Ethylene Glycol | 8.0 |
| Xanthum Gum thickening agent | 0.2 |
| Antifoam C foam suppressant, Dow Corning Corporation | 0.5 |
| Water | 39.3 |
| | 100.0 |

The above ingredients are intimately admixed and finely ground to provide a suitable suspension, which is then further diluted with water at the application site.

| Dust | |
|---|---|
| Ingredient | Concentration by Weight (Percent) |
| 5-Bromo-1-(4-chlorophenyl)-N—methyl-1H-pyrazole-4-carboxamide | 10.0 |
| Diatomite, a diatomaceous earth, Witco Chemical Corporation, Inorganic Specialties Division | 90.0 |
| | 100.0 |

The active ingredient and diatomaceous earth are intimately mixed and ground to a fine powder of uniform particle size of about 16 to about 40 microns. The dust thus formed may be applied by any number of conventional methods, for example by an aerial application.

| Granules | |
|---|---|
| Ingredient | Concentration by Weight (Percent) |
| 5-Chloro-1-(2,4-difluorophenyl)-N—methyl-1H-pyrazole-4-carboxamide | 5.0 |
| Heavy aromatic naphtha | 5.0 |
| Bentonite 20/40 mesh granular clay, The Floridin Company | 90.0 |
| | 100.0 |

The compound is dissolved in the naptha and sprayed onto the clay granules, typically under agitation, and the formulated granules are sieved to provide a uniform mesh size.

The herbicidal activity of representative compounds of the present invention is illustrated by the following experiments.

EXPERIMENT 1

The initial screen used to evaluate herbicidal efficacy was conducted at a test compound concentration of 15 lbs/acre (16.8 kg/ha). In this test a standard sand:soil mixture (1:1) was added to separate containers and tomato, large crabgrass and pigweed seeds were planted by row. Each container was then fertilized before treatment.

The test compounds were formulated for application by dissolving the compound into a solvent prepared by combining Toximul R and Toximul S (proprietary blends of anionic and nonionic surfactants manufactured by Stepan Chemical Company, Northfield, Ill.) with a 1:1 (v/v) mixture of acetone:ethanol. The solvent/compound solution was diluted with deionized water and applied postemergence to some planted containers and preemergence to others using a DeVilbiss atomizer. Postemergence treatment was made 11 to 13 days after planting while preemergence treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows:

A=abscission of leaves
B=burned
C=chlorosis
D=death
E=epinasty
F=formation effects
G=dark green
I=increased plant growth
L=local necrosis
N=no germination
P=purple pigmentation
R=reduced germination
S=stunting
U=unclassified injury Table I presents the herbicidal activity of type 4-pyrazole carboxamide derivatives of the invention when evaluated in the screen described above.

TABLE I

| | Herbicide Pretest at 15 lbs/acre (16.8 kg/ha) | | | | | |
|---|---|---|---|---|---|---|
| Example No. | Preemergence | | | Postemergence | | |
| of Compound Tested | Tomato | Large Crabgrass | Pigweed | Tomato | Large Crabgrass | Pigweed |
| 1 | 2S | 4RS | 5D | 5D | 4BS | 5D |
| 2 | 1 | 2S | 2S | 5D | 4BS | 5D |
| 3 | 2S | 2S | 2S | 5D | 5D | 5D |
| 4 | 1 | 2RS | 1 | 5D | 4BS | 5D |

TABLE I-continued

| | Herbicide Pretest at 15 lbs/acre (16.8 kg/ha) | | | | | |
|---|---|---|---|---|---|---|
| Example No. | Preemergence | | | Postemergence | | |
| of Compound Tested | Tomato | Large Crabgrass | Pigweed | Tomato | Large Crabgrass | Pigweed |
| 5 | 1 | 1 | 1 | 4BS | 3BS | 4BS |
| 6 | 1 | 1 | 1 | 3BS | 1 | 1 |
| 7 | 1 | 1 | 1 | 1 | 1 | 1 |
| 8 | 4RS | 4BS | 5N | 5D | 4BCS | 5D |
| 9 | 1 | 1 | 1 | 4BCS | 3BS | 4BS |
| 10 | 1 | 1 | 1 | 1 | 1 | 1 |
| 11 | 1 | 1 | 1 | 1 | 1 | 1 |
| 12 | 1 | 1 | 1 | 2BS | 1 | 1 |
| 13 | 1 | 1 | 1 | 1 | 1 | 1 |
| 14 | 1 | 1 | 1 | 1 | 1 | 1 |
| 15 | 1 | 1 | 1 | 1 | 1 | 1 |
| 16 | 1 | 1 | 1 | 2BS | 1 | 1 |
| 17 | 1 | 1 | 1 | 1 | 1 | 1 |
| 18 | 3S | 4RS | 4RS | 4BS | 5D | 4BS |
| 19 | 2S | 4RS | 4RS | 5D | 4BS | 5D |
| 20 | 1 | 2S | 2S | 5D | 5D | 5D |
| 21 | 1 | 1 | 1 | 1 | 1 | 1 |
| 23 | 1 | 1 | 1 | 1 | 1 | 1 |
| 24 | 1 | 1 | 1 | 5D | 5D | 5D |
| 25 | 5N | 2S | 4BS | 2B | 2B | 2B |
| 26 | 1 | 1 | 1 | 1 | 1 | 1 |
| 27 | 1 | 1 | 1 | 2S | 2BS | 2BS |
| 28 | 1 | 1 | 1 | 1 | 1 | 1 |
| 29 | 1 | 1 | 1 | 4BS | 5D | 1 |
| 30 | 1 | 1 | 1 | 5D | 5D | 2BS |
| 31 | 2S | 2S | 2RS | 5D | 5D | 5D |
| 32 | 5N | 4S | 5N | 4BS | 4BS | 4BS |
| 33 | 1 | 1 | 1 | 1 | 1 | 1 |
| 34 | 5N | 4RS | 4RS | 5D | 2BS | 1 |
| 35 | 5N | 5N | 5N | 5D | 4BS | 5D |
| 36 | 5N | 4RS | 4RS | 5D | 5D | 5D |
| 37 | 1 | 1 | 1 | 1 | 1 | 1 |
| 38 | 1 | 1 | 1 | 1 | 1 | 1 |
| 39 | 1 | 1 | 1 | 1 | 1 | 1 |
| 40 | 2S | 2RS | 1 | 5D | 4BS | 4BS |
| 41 | 1 | 1 | 1 | 2BS | 2BS | 1 |
| 42 | 1 | 1 | 2RS | 5D | 5D | 4BS |
| 44 | 1 | 1 | 1 | 5D | 5D | 5D |
| 45 | 1 | 1 | 2S | 2S | 2BS | 2BS |
| 47 | 3BCS | 4RS | 5D | 5D | 4BS | 5D |
| 49 | 2BS | 2S | 5D | 5D | 3BS | 3BS |
| 50 | 1 | 1 | 1 | 1 | 1 | 1 |
| 51 | 1 | 1 | 1 | 1 | 1 | 1 |
| 52 | 5D | 4BS | 5D | 4BS | 4BS | 4BS |
| 53 | 1 | 1 | 1 | 3BS | 1 | 1 |
| 54 | 1 | 1 | 1 | 1 | 1 | 1 |
| 55 | 5D | 5D | 5D | 5D | 5D | 5D |
| 56 | 2S | 2RS | 3RS | 5D | 5D | 5D |
| 57 | 1 | 1 | 1 | 5D | 5D | 5D |
| 58 | 1 | 2S | 2S | 1 | 5D | 4BS |
| 59 | 1 | 1 | 2RS | 5D | 5D | 5D |
| 61 | 1 | 1 | 1 | 5D | 4BS | 4BS |
| 62 | 1 | 1 | 1 | 5D | 5D | 5D |
| 63 | 1 | 1 | 1 | 3BS | 2BS | 2BS |
| 64 | 1 | 1 | 1 | 4BS | 4BS | 5D |
| 65 | 1 | 2RS | 2BS | 5D | 4BS | 5D |
| 66 | 4RS | 4RS | 4RS | 5D | 5D | 5D |
| 67 | 1 | 2S | 2S | 5D | 5D | 5D |
| 68 | 1 | 1 | 1 | 4BS | 4BS | 5D |
| 70 | 2RS | 2RS | 3RS | 5D | 5D | 5D |
| 71 | 2S | 1 | 1 | 5D | 5D | 5D |
| 72 | 1 | 1 | 2RS | 5D | 4BS | 5D |
| 73 | 1 | 2S | 1 | 5D | 4BS | 5D |
| 74 | 1 | 1 | 1 | 1 | 1 | 1 |
| 75 | 1 | 1 | 1 | 1 | 1 | 1 |
| 76 | 1 | 3RS | 2S | 5D | 5D | 5D |
| 78 | 1 | 1 | 1 | 1 | 1 | 1 |
| 79 | 1 | 1 | 1 | 1 | 1 | 1 |
| 80 | 1 | 1 | 1 | 1 | 1 | 1 |
| 81 | 1 | 1 | 1 | 1 | 1 | 1 |
| 94 | 1 | 2B | 3RS | 4BS | 4BS | 5D |
| 95 | 4BS | 5D | 5D | 5D | 5D | 5D |
| 96 | 2S | 4BS | 4RS | 5D | 4BS | 5D |
| 97 | 3CS | 4SB | 4BS | 5D | 5D | 5D |
| 98 | 5N | 5D | 5D | 5D | 5D | 5D |
| 99 | 5N | 5D | 5N | 5D | 5D | 5D |
| 100 | 4SB | 4BS | 4BS | 5D | 5D | 5D |

TABLE I-continued

| | Herbicide Pretest at 15 lbs/acre (16.8 kg/ha) | | | | | |
|---|---|---|---|---|---|---|
| Example No. | Preemergence | | | Postemergence | | |
| of Compound Tested | Tomato | Large Crabgrass | Pigweed | Tomato | Large Crabgrass | Pigweed |
| 103 | 2SC | 4SB | 4RS | 5D | 5D | 5D |
| 104 | 4BS | 3BS | 4RS | 5D | 5D | 5D |
| 105 | 4BS | 4SB | 5D | 5D | 5D | 5D |
| 107 | 5D | 5D | 5D | 5D | 5D | 5D |
| 109 | 4BS | 4BS | 4RS | 5D | 5D | 5D |
| 110 | 4BS | 4RS | 5D | 5D | 5D | 5D |
| 112 | 4BS | 4BS | 4BS | 5D | 5D | 5D |
| 113 | 4BS | 4SB | 5D | 5D | 5D | 5D |
| 114 | 4BS | 5D | 5D | 5D | 5D | 5D |
| 118 | 3SC | 4BS | 5N | 5D | 5D | 5D |
| 119 | 5D | 4SB | 5D | 5D | 5D | 5D |
| 120 | 2S | 3RS | 4RS | 5D | 4BS | 5D |
| 121 | 3BS | 4SB | 5D | 5D | 5D | 5D |
| 122 | 2B | 5N | 5N | 5D | 4BS | 5D |
| 123 | 2SB | 4SB | 4RS | 5D | 5D | 5D |
| 124 | 3SB | 4SB | 4RS | 5D | 5D | 5D |
| 125 | 4BS | 4BS | 5D | 5D | 5D | 5D |
| 126 | 5D | 5D | 5N | 5D | 5D | 5D |
| 127 | 1 | 1 | 1 | 4BS | 4BS | 5D |
| 128 | 5D | 5D | 5D | 5D | 5D | 5D |
| 141 | 4RS | 4SB | 5D | 5D | 5D | 5D |
| 142 | 5D | 5D | 5D | 5D | 5D | 5D |
| 145 | 5D | 4BS | 5D | 5D | 5D | 5D |
| 146 | 4BS | 4BS | 4RS | 5D | 5D | 5D |
| 147 | 4BS | 4SB | 5D | 5D | 5D | 5D |
| 148 | 5N | 4BS | 5D | 5D | 5D | 5D |
| 156 | 1 | 3S | 5N | 5D | 5D | 5D |
| 157 | 4BS | 4RS | 4RS | 5D | 5D | 5D |
| 166 | 1 | 1 | 1 | 5D | 4BS | 3BS |

EXPERIMENT 2

The herbicidal activity of some of the compounds of the present invention was further evaluated at various application rates in a multiple species greenhouse test. Several additional weed and crop species were utilized to determine the herbicidal activity and selectivity of the test compounds. Lower concentrations of the test compounds were obtained by serial dilution of the above described formulation with a mixture of the surfactant containing solvent and deionized water. The compounds were evaluated according to the general procedure outlined above. Table II present the preemergence herbicidal test results, while Table III presents postemergence test data, both applications being administered at 8 lbs/acre (8.96 kg/ha) or less. In Table II the species employed in this test are coded as follows:

| | |
|---|---|
| A = Corn | K = Lambsquarter |
| B = Cotton | L = Large Crabgrass |
| C = Soybean | M = Mustard |
| D = Wheat | N = Pigweed |
| E = Alfalfa | O = Foxtail |
| F = Sugar Beet | P = Wild Oat |
| G = Rice | Q = Velvetleaf |
| H = Cucumber | R = Jimsonweed |
| I = Tomato | S = Morningglory |
| J = Barnyard Grass | T = Zinnia |

TABLE II

| Example No. of Compound Tested | Rate of Appln. lbs/acre (kg/ha) | Preemergence | | | | | | | | | | | | | | | | | | | |
|---|---|---|---|---|---|---|---|---|---|---|---|---|---|---|---|---|---|---|---|---|---|
| | | Crops | | | | | | | | Weeds | | | | | | | | | | | |
| | | A | B | C | D | E | F | G | H | I | J | K | L | M | N | O | P | Q | R | S | T |
| 1 | 8.0 (8.96) | 3 | | | | | | | | | | | 5 | | 5 | 4 | | 5 | | 4 | 4 |
| | 4.0 (4.48) | 1 | 1 | 3 | 3 | 4 | 4 | 2 | 4 | 4 | 3 | 5 | 5 | 4 | 5 | 5 | 4 | 5 | 5 | 5 | 4 |
| | 2.0 (2.24) | 1 | 1 | 2 | 1 | 4 | 3 | 1 | 4 | 3 | 2 | 5 | 5 | 5 | 5 | 5 | 3 | 5 | 5 | 2 | 5 |
| | 1.0 (1.12) | 1 | 1 | 1 | 1 | 3 | 1 | 1 | 3 | 1 | 1 | 3 | 4 | 2 | 5 | 3 | 1 | 3 | 1 | 1 | 2 |
| | 1.0 (1.12) | 1 | 1 | 1 | 1 | 3 | 4 | 2 | 3 | 1 | 1 | 2 | 4 | 3 | 4 | 3 | 1 | 3 | 1 | 1 | 2 |
| | 0.5 (0.56) | 1 | 1 | 1 | 1 | 1 | 2 | 1 | 2 | 1 | 1 | 2 | 2 | 1 | 3 | 2 | 1 | 1 | 1 | 1 | 1 |
| | 0.25 (0.28) | 1 | 1 | 1 | 1 | 1 | 2 | 1 | 2 | 1 | 1 | 2 | 1 | 1 | 2 | 1 | 1 | 1 | 2 | 1 | 1 |
| 2 | 8.0 (8.96) | 1 | | | | | | | | | | | 4 | | 5 | 4 | | 5 | | 2 | 3 |
| | 4.0 (4.48) | 1 | 1 | 1 | 1 | 2 | 3 | 1 | 4 | 1 | 2 | 2 | 3 | 2 | 4 | 4 | 1 | 3 | 2 | 1 | 1 |
| | 2.0 (2.24) | 1 | 1 | 1 | 1 | 1 | 1 | 1 | 3 | 1 | 1 | 1 | 2 | 3 | 3 | 3 | 1 | 2 | 1 | 1 | 1 |
| | 1.0 (1.12) | 1 | 1 | 1 | 1 | 1 | 1 | 1 | 1 | 1 | 1 | 1 | 1 | 2 | 1 | 3 | 1 | 2 | 1 | 1 | 1 |
| 3 | 8.0 (8.96) | 2 | | | | | | | | | | | 5 | | 5. | 5 | | 4 | | 2 | 3 |
| | 4.0 (4.48) | 2 | 1 | 2 | 2 | 3 | 4 | 2 | 5 | 4 | 4 | 5 | 5 | 4 | 5 | 4 | 4 | 4 | 4 | 4 | 4 |
| | 2.0 (2.24) | 1 | 1 | 2 | 2 | 3 | 4 | 1 | 1 | 2 | 4 | 4 | 4 | 2 | 5 | 4 | 3 | 4 | 4 | 2 | 2 |
| | 1.0 (1.12) | 1 | 1 | 2 | 1 | 2 | 1 | 1 | 1 | 1 | 3 | 4 | 4 | 1 | 4 | 3 | 2 | 4 | 3 | 1 | 2 |
| | 1.0 (1.12) | 1 | 2 | 2 | 1 | 1 | 2 | 1 | 1 | 1 | 2 | 4 | 4 | 3 | 4 | 4 | 1 | 2 | 1 | 1 | 2 |
| | 0.5 (0.56) | 1 | 5 | 2 | 4 | 3 | 3 | 1 | 2 | 2 | 2 | 3 | 4 | 3 | 4 | 4 | 1 | 2 | 1 | 2 | 3 |
| | 0.125 (0.14) | 1 | 1 | 4 | 1 | 2 | 1 | 1 | 1 | 1 | 1 | 2 | 3 | 1 | 3 | 2 | 1 | 2 | 1 | 1 | 1 |
| | 0.25 (0.28) | 1 | 2 | 2 | 3 | 1 | 1 | 2 | 1 | 1 | 1 | 4 | 4 | 4 | 5 | 2 | 1 | 1 | 2 | 1 | 3 |
| | 0.25 (0.28) | 1 | 1 | 2 | 1 | 2 | 1 | 1 | 1 | 1 | 1 | 2 | 2 | 2 | 3 | 3 | 1 | 3 | 2 | 1 | 1 |

TABLE II-continued

Preemergence

| Example No. of Compound Tested | Rate of Appln. lbs/acre | (kg/ha) | Crops | | | | | | | | | Weeds | | | | | | | | | |
|---|---|---|---|---|---|---|---|---|---|---|---|---|---|---|---|---|---|---|---|---|---|
| | | | A | B | C | D | E | F | G | H | I | J | K | L | M | N | O | P | Q | R | S | T |
| | 0.0625 | (0.07) | 1 | 1 | 3 | 1 | 2 | 1 | 1 | 1 | 1 | 1 | 1 | 2 | 1 | 1 | 1 | 1 | 2 | 1 | 1 | 1 |
| 4 | 8.0 | (8.96) | | | | | | | | | 1 | 4 | | 5 | 4 | 5 | 4 | 2 | 2 | | 1 | 3 |
| | 4.0 | (4.48) | 2 | 2 | 2 | 1 | 2 | 5 | 2 | 5 | 4 | 4 | 5 | 5 | 4 | 5 | 4 | 2 | 4 | 4 | 2 | 3 |
| | 2.0 | (2.24) | 2 | 1 | 1 | | 2 | 4 | 2 | 3 | 2 | 3 | 4 | 5 | 3 | 5 | 4 | 1 | 4 | 1 | 1 | 2 |
| | 1.0 | (1.12) | 1 | 1 | 1 | | 1 | 4 | 2 | 2 | 1 | 1 | 4 | 4 | 2 | 4 | 2 | 1 | 2 | 1 | 1 | 2 |
| | 1.0 | (1.12) | 1 | 1 | 1 | 1 | 1 | 1 | 1 | 1 | 2 | 2 | 4 | 2 | 2 | 3 | 1 | 1 | 1 | 1 | 1 | 1 |
| | 0.5 | (0.56) | 1 | 1 | 1 | 1 | 1 | 1 | 1 | 1 | 2 | 1 | 1 | 1 | 1 | 2 | 1 | 1 | 1 | 1 | 1 | 1 |
| | 0.25 | (0.28) | 3 | 1 | 2 | 3 | 1 | 1 | 2 | 2 | 1 | 3 | 4 | 3 | 3 | 2 | 2 | 2 | 2 | 1 | 2 | 2 |
| 5 | 8.0 | (8.96) | 1 | | | | | | | | | 4 | | 5 | 3 | | 4 | | | | 2 | 3 |
| | 4.0 | (4.48) | 2 | 2 | 2 | 1 | 2 | 2 | 1 | 3 | 2 | 2 | 4 | 2 | 2 | 4 | 2 | 1 | 3 | 1 | 2 | 2 |
| | 2.0 | (2.24) | 2 | 2 | 2 | 1 | 2 | 2 | 1 | 3 | 3 | 3 | 4 | 4 | 3 | 4 | 3 | 1 | 3 | 3 | 3 | 2 |
| | 1.0 | (1.12) | 1 | 1 | 2 | 1 | 1 | 1 | 1 | 1 | 1 | 1 | 4 | 3 | 3 | 3 | 1 | 1 | 1 | 1 | 1 | 2 |
| 6 | 8.0 | (8.96) | 1 | | | | | | | | | | | 3 | | 3 | 3 | | 3 | | | 1 | 3 |
| 7 | 8.0 | (8.96) | 2 | | | | | | | | | | | 3 | | 3 | 3 | | 3 | | | 1 | 4 |
| 8 | 8.0 | (8.96) | 3 | | | | | | | | | | | 4 | | 5 | 4 | | 5 | | | 3 | 3 |
| | 4.0 | (4.48) | 2 | 2 | 2 | 2 | 5 | 5 | 2 | 4 | 4 | 3 | 5 | 4 | 4 | 5 | 4 | 3 | 5 | 3 | 4 | 4 |
| | 2.0 | (2.24) | 2 | 1 | 2 | 2 | 3 | 3 | 2 | 5 | 3 | 3 | 5 | 5 | 4 | 5 | 3 | 2 | 4 | 2 | 2 | 2 |
| | 1.0 | (1.12) | 1 | 1 | 1 | 1 | 2 | 4 | 2 | 2 | 1 | 2 | 4 | 3. | 2 | 4 | 4 | 2 | 4 | 1 | 2 | 2 |
| | 1.0 | (1.12) | 2 | 2 | 2 | 1 | 2 | 4 | 2 | 3 | 1 | 2 | 4 | 4 | 4 | 4 | 4 | 1 | 2 | 2 | 1 | 2 |
| | 0.5 | (0.56) | 2 | 2 | 2 | 1 | 2 | 2 | 1 | 2 | 1 | 1 | 3 | 3 | 2 | 3 | 3 | 1 | 1 | 1 | 2 | 3 |
| | 0.25 | (0.28) | 1 | 1 | 1 | 1 | 1 | 1 | 1 | 1 | 1 | 1 | 2 | 2 | 2 | 2 | 2 | 1 | 1 | 1 | 1 | 1 |
| 9 | 8.0 | (8.96) | 1 | | | | | | | | | | | 1 | | 3 | 1 | | 1 | | | 1 | 1 |
| 10 | 8.0 | (8.96) | 1 | | | | | | | | | | | 3 | | 4 | 3 | | 1 | | | 1 | 1 |
| 11 | 8.0 | (8.96) | | | | | | | | | 1 | 1 | | 3 | 1 | 5 | 2 | 2 | 2 | | | 2 | 2 |
| | 4.0 | (4.48) | 1 | 1 | 1 | 1 | 1 | 1 | 1 | 1 | 1 | 1 | 2 | 1 | 1 | 3 | 1 | 1 | 1 | 1 | 1 | 1 |
| | 2.0 | (2.24) | 1 | 1 | 1 | 1 | 1 | 1 | 1 | 1 | 1 | 1 | 2 | 1 | 1 | 2 | 1 | 1 | 1 | 1 | 1 | 1 |
| | 1.0 | (1.12) | 1 | 1 | 1 | 1 | 1 | 1 | 1 | 1 | 1 | 1 | 1 | 1 | 1 | 1 | 1 | 1 | 1 | 1 | 1 | 1 |
| 12 | 8.0 | (8.96) | | | | | | | | | 2 | 2 | | 2 | 2 | 4 | 4 | 2 | 3 | | | 2 | 3 |
| | 4.0 | (4.48) | 1 | 1 | 2 | 2 | 2 | 3 | 2 | 3 | 2 | 2 | 4 | 4 | 2 | 4 | 3 | 1 | 3 | 2 | 2 | 3 |
| | 2.0 | (2.24) | 1 | 2 | 1 | 1 | 1 | 3 | 1 | 2 | 2 | 1 | 3 | 2 | 2 | 3 | 2 | 1 | 3 | 2 | 1 | 2 |
| | 1.0 | (1.12) | 1 | 1 | 1 | 1 | 1 | 1 | 1 | 2 | 1 | 1 | 3 | 1 | 2 | 1 | 1 | 1 | 1 | 1 | 1 | 1 |
| 13 | 8.0 | (8.96) | | | | | | | | | 3 | 1 | | 4 | 1 | 1 | 3 | 1 | 2 | | | 1 | 2 |
| 14 | 8.0 | (8.96) | | | | | | | | | 1 | 1 | | 2 | 3 | 2 | 3 | 1 | 4 | | | 1 | 2 |
| 15 | 8.0 | (8.96) | 1 | | | | | | | | | | | 1 | | 1 | 1 | | 1 | | | 1 | 1 |
| 16 | 8.0 | (8.96) | 1 | | | | | | | | | | | 3 | | 4 | 2 | | 1 | | | 1 | 2 |
| 17 | 8.0 | (8.96) | 1 | | | | | | | | | | | 3 | | 3 | 1 | | 1 | | | 2 | 2 |
| 18 | 8.0 | (8.96) | 2 | | | | | | | | | | | 4 | | 4 | 4 | | 4 | | | 3 | 4 |
| | 4.0 | (4.48) | 2 | 1 | 2 | 2 | 3 | 4 | 2 | 4 | 3 | 2 | 4 | 4 | 3 | 2 | 3 | 2 | 3 | 4 | 3 | 3 |
| | 2.0 | (2.24) | 1 | 1 | 2 | 2 | 2 | 2 | 2 | 3 | 2 | 1 | 4 | 4 | 3 | 1 | 1 | 1 | 2 | 1 | 2 | 1 |
| | 1.0 | (1.12) | 1 | 1 | 1 | 1 | 1 | 2 | 1 | 2 | 1 | 1 | 2 | 4 | 2 | 2 | 1 | 1 | 1 | 1 | 1 | 1 |
| 19 | 8.0 | (8.96) | 2 | | | | | | | | | | | 5 | | 5 | 4 | | 5 | | | 4 | 4 |
| | 4.0 | (4.48) | 1 | 1 | 2 | 1 | 4 | 4 | 1 | 4 | 2 | 1 | 5 | 4 | 3 | 5 | 3 | 2 | 5 | 3 | 2 | 3 |
| | 2.0 | (2.24) | 1 | 1 | 1 | 1 | 3 | 3 | 2 | 2 | 1 | 1 | 4 | 2 | 3 | 4 | 2 | 4 | 3 | 1 | 1 | 1 |
| | 1.0 | (1.12) | 1 | 1 | 1 | 1 | 3 | 2 | 1 | 2 | 1 | 1 | 3 | 3 | 2 | 3 | 1 | 1 | 3 | 3 | 1 | 1 |
| 20 | 8.0 | (8.96) | 3 | | | | | | | | | | | 5 | | 5 | 4 | | 5 | | | 4 | 4 |
| | 4.0 | (4.48) | 2 | 2 | 3 | 1 | 5 | 4 | 1 | 4 | 4 | 3 | 5 | 4 | 4 | | 4 | 4 | 5 | 5 | 4 | 4 |
| | 2.0 | (2.24) | 1 | 2 | 3 | 1 | 5 | 3 | 1 | 3 | 4 | 2 | | 4 | 3 | | 4 | 2 | 5 | 5 | 5 | 4 |
| | 1.0 | (1.12) | 1 | 1 | 2 | 1 | 5 | 4 | 1 | 2 | 3 | 2 | | 4 | 3 | | 3 | 2 | 3 | 1 | 1 | 3 |
| | 1.0 | (1.12) | 1 | 1 | 1 | 1 | 2 | 2 | 2 | 2 | 1 | 1 | 4 | 3 | 2 | 3 | 2 | 1 | 3 | 1 | 1 | 1 |
| | 0.50 | (0.56) | 1 | 1 | 1 | 2 | 1 | 2 | 1 | 1 | 1 | 3 | 3 | 1 | 2 | 1 | 1 | 2 | 2 | 2 | 2 | 2 |
| | 0.25 | (0.28) | 1 | 1 | 1 | 2 | 1 | 2 | 1 | 1 | 1 | 1 | 1 | 1 | 1 | 1 | 1 | 1 | 1 | 1 | 1 | 1 |
| 21 | 8.0 | (8.96) | | | | | | | | | 1 | 1 | | 1 | 1 | 1 | 1 | 1 | 1 | | | 1 | 1 |
| 22 | 8.0 | (8.96) | | | | | | | | | 2 | 2 | | 2 | 2 | 3 | 3 | 1 | 2 | | | 1 | 1 |
| 23 | 8.0 | (8.96) | 1 | | | | | | | | | | | 4 | | 5 | 4 | | 1 | | | 1 | 3 |
| | 4.0 | (4.48) | 1 | 1 | 2 | 2 | | 4 | 3 | 5 | 3 | 3 | | 4 | 4 | | 4 | 3 | 3 | 3 | 2 | 4 |
| | 2.0 | (2.24) | 1 | 1 | 1 | 1 | | 4 | 2 | 2 | 2 | 1 | | 4 | 4 | | 4 | 3 | 3 | 1 | 1 | 3 |
| | 1.0 | (1.12) | 1 | 1 | 1 | 1 | | 3 | 1 | 1 | 1 | 1 | | 4 | 3 | | 4 | 4 | 3 | 5 | 3 | 3 |
| | 1.0 | (1.12) | 1 | 1 | 1 | 1 | 2 | 2 | 1 | 2 | 1 | 1 | 3 | 3 | 2 | 2 | 3 | 1 | 1 | 1 | 1 | 1 |
| | 0.50 | (0.56) | 1 | 1 | 1 | 1 | 1 | 1 | 1 | 1 | 1 | 1 | 2 | 3 | 1 | 1 | 2 | 1 | 1 | 1 | 1 | 1 |
| | 0.25 | (0.28) | 1 | 1 | 1 | 1 | 1 | 1 | 1 | 1 | 1 | 1 | 2 | 2 | 1 | 1 | 1 | 1 | 1 | 1 | 1 | 1 |
| 24 | 8.0 | (8.96) | 2 | | | | | | | | | | | 5 | | 5 | 4 | | 3 | | | 3 | 4 |
| | 4.0 | (4.48) | 1 | 1 | 1 | 1 | | 3 | 2 | 3 | 3 | 1 | | 4 | 4 | | 4 | 4 | 4 | 3 | 3 | 3 |
| | 2.0 | (2.24) | 1 | 1 | 1 | 1 | 1 | 2 | 1 | 3 | 2 | 1 | | 4 | 4 | | 4 | 1 | 1 | 1 | 1 | 3 |
| | 1.0 | (1.12) | 1 | 1 | 1 | 1 | 1 | 1 | 1 | 1 | 1 | 1 | | 5 | 3 | | 4 | 1 | 1 | 1 | 1 | 2 |
| | 1.0 | (1.12) | 1 | 1 | 1 | 1 | 2 | 2 | 1 | 3 | 1 | 1 | 4 | 3 | 3 | 2 | 3 | 1 | 1 | 1 | 1 | 1 |
| | 0.50 | (0.56) | 1 | 1 | 1 | 1 | 1 | 1 | 1 | 1 | 1 | 1 | 3 | 2 | 2 | 2 | 2 | 1 | 1 | 1 | 1 | 1 |
| | 0.25 | (0.28) | 1 | 1 | 1 | 1 | 1 | 1 | 1 | 1 | 1 | 1 | 3 | 2 | 1 | 1 | 1 | 1 | 1 | 1 | 1 | 1 |
| 25 | 8.0 | (8.96) | | | | | | | | | 3 | 1 | | 3 | 1 | 1 | 1 | 1 | 1 | | | 1 | 1 |
| 26 | 8.0 | (8.96) | 1 | | | | | | | | | | | 3 | | 3 | 3 | | 1 | | | 2 | 1 |
| 27 | 8.0 | (8.96) | 1 | | | | | | | | | | | 3 | | 5 | 2 | | 1 | | | 1 | 1 |
| | 4.0 | (4.48) | 1 | 2 | 1 | 1 | 1 | 1 | 2 | 2 | 1 | 1 | 3 | 2 | 2 | 2 | 3 | 1 | 1 | 1 | 1 | 1 |
| | 2.0 | (2.24) | 1 | 1 | 1 | 1 | 1 | 1 | 1 | 1 | 1 | 1 | 3 | 3 | 1 | 2 | 2 | 1 | 1 | 1 | 1 | 1 |
| | 1.0 | (1.12) | 1 | 1 | 1 | 1 | 1 | 1 | 1 | 1 | 1 | 1 | 2 | 2 | 1 | 1 | 1 | 1 | 1 | 1 | 1 | 1 |
| 28 | 8.0 | (8.96) | | | | | | | | | 3 | 3 | | 4 | 4 | 5 | 3 | 1 | 4 | | | 1 | 2 |
| | 4.0 | (4.48) | 1 | 1 | 1 | 1 | 1 | 4 | 2 | 4 | 1 | 2 | 1 | 2 | 1 | 3 | 3 | 1 | 1 | 1 | 3 | 1 |
| | 2.0 | (2.24) | 1 | 1 | 1 | 1 | 1 | 3 | 1 | 2 | 1 | 1 | 1 | 1 | 1 | 2 | 1 | 1 | 1 | 1 | 1 | 1 |

TABLE II-continued

Preemergence

| Example No. of Compound Tested | Rate of Appln. lbs/acre (kg/ha) | Crops | | | | | | | | | Weeds | | | | | | | | | |
|---|---|---|---|---|---|---|---|---|---|---|---|---|---|---|---|---|---|---|---|---|
| | | A | B | C | D | E | F | G | H | I | J | K | L | M | N | O | P | Q | R | S | T |
| | 1.0 (1.12) | 1 | 1 | 1 | 1 | 1 | 1 | 1 | 1 | 1 | 1 | 2 | 1 | 2 | 2 | 1 | 1 | 1 | 1 | 1 | 1 |
| 29 | 8.0 (8.96) | 1 | | | | | | | | | | | 1 | | 1 | 1 | | 1 | | 1 | 1 |
| 30 | 8.0 (8.96) | 1 | | | | | | | | | | | 1 | | 1 | 1 | | 1 | | 1 | 1 |
| 31 | 8.0 (8.96) | 1 | | | | | | | | | | | 4 | | 5 | 5 | | 5 | | 4 | 5 |
| | 4.0 (4.48) | 1 | 3 | 2 | 1 | 4 | 4 | 3 | 5 | 3 | 3 | 5 | 5 | 4 | 4 | 4 | 3 | 3 | 3 | 1 | 4 |
| | 2.0 (2.24) | 1 | 2 | 1 | 1 | 2 | 4 | 3 | 4 | 2 | 3 | 5 | 4 | 4 | 4 | 3 | 2 | 2 | 3 | 1 | 2 |
| | 1.0 (1.12) | 1 | 2 | 1 | 1 | 1 | 3 | 1 | 3 | 2 | 3 | 4 | 3 | 3 | 3 | 3 | 1 | 1 | 1 | 1 | 2 |
| 32 | 8.0 (8.96) | | | | | | | | | 3 | 3 | | 4 | 4 | 4 | 3 | 2 | 4 | | 1 | 3 |
| | 4.0 (4.48) | 2 | 1 | 1 | 2 | 3 | 5 | 2 | 3 | 2 | 3 | 4 | 3 | 3 | 3 | 3 | 1 | 2 | 2 | 1 | 1 |
| | 2.0 (2.24) | 1 | 1 | 1 | 2 | 3 | 1 | 2 | 1 | 1 | 2 | 1 | 2 | 1 | 3 | 2 | 1 | 1 | 1 | 1 | 1 |
| | 1.0 (1.12) | 1 | 1 | 1 | 1 | 3 | 3 | 1 | 1 | 1 | 1 | 1 | 1 | 1 | 2 | 1 | 1 | 1 | 1 | 1 | 1 |
| 33 | 8.0 (8.96) | | | | | | | | | 4 | 1 | | 2 | | 2 | 2 | 3 | 2 | | 3 | 3 |
| 34 | 8.0 (8.96) | 1 | | | | | | | | | | | 4 | | 4 | 3 | | 4 | | 3 | 3 |
| | 4.0 (4.48) | 1 | 1 | 1 | 1 | 1 | 3 | 1 | 2 | 1 | 1 | 4 | 2 | 2 | 3 | 1 | 1 | 1 | 1 | 1 | 1 |
| | 2.0 (2.24) | 1 | 1 | 1 | 1 | 1 | 1 | 1 | 1 | 1 | 1 | 3 | 2 | 2 | 3 | 1 | 1 | 1 | 1 | 1 | 1 |
| | 1.0 (1.12) | 1 | 1 | 1 | 1 | 1 | 1 | 1 | 1 | 1 | 1 | 3 | 3 | 3 | 3 | 1 | 1 | 1 | 1 | 1 | 1 |
| 35 | 8.0 (8.96) | 2 | | | | | | | | | | | 4 | | 5 | 4 | | 4 | | 4 | 4 |
| | 4.0 (4.48) | 1 | 1 | 1 | 1 | 4 | 2 | 2 | 4 | 2 | 1 | 5 | 4 | 4 | 5 | 3 | 1 | 3 | 2 | 3 | 3 |
| | 2.0 (2.24) | 1 | | | | | | | | | | | 3 | | 4 | 2 | | 2 | | 1 | 1 |
| | 1.0 (1.12) | 1 | 1 | 1 | 1 | 2 | 1 | 1 | 3 | 2 | 1 | 4 | 3 | 2 | 3 | 2 | 1 | 2 | 1 | 1 | 1 |
| 36 | 8.0 (8.96) | 2 | | | | | | | | | | | 5 | | 5 | 4 | | 5 | | 4 | 4 |
| | 4.0 (4.48) | 3 | 2 | 3 | 4 | 5 | 4 | 3 | 5 | 5 | 4 | 5 | 5 | 5 | 5 | 4 | 4 | 5 | 5 | 4 | 5 |
| | 2.0 (2.24) | 2 | 2 | 2 | 2 | 5 | 4 | 3 | 3 | 3 | 4 | 5 | 4 | 4 | 5 | 4 | 4 | 4 | 3 | 3 | 5 |
| | 1.0 (1.12) | 2 | 2 | 2 | 2 | 5 | 4 | 3 | 4 | 3 | 4 | 5 | 4 | 4 | 5 | 4 | 4 | 5 | 3 | 4 | 5 |
| | 1.0 (1.12) | 1 | 1 | 2 | 1 | 3 | 4 | 2 | 4 | 4 | 4 | 5 | 5 | 4 | 4 | 4 | 3 | 3 | 3 | 2 | 3 |
| | 0.50 (0.56) | 1 | 1 | 1 | 1 | 2 | 4 | 2 | 3 | 3 | 2 | 5 | 5 | 4 | 4 | 4 | 2 | 4 | 2 | 1 | 3 |
| | 0.25 (0.28) | 1 | 1 | 1 | 1 | 2 | 1 | 1 | 2 | 1 | 1 | 4 | 3 | 2 | 2 | 1 | 1 | 2 | 1 | 1 | 1 |
| 37 | 8.0 (8.96) | 1 | | | | | | | | | | | 1 | | 1 | 1 | | 1 | | 1 | 2 |
| 38 | 8.0 (8.96) | 1 | | | | | | | | | | | 2 | | 3 | 2 | | 2 | | 1 | 1 |
| 39 | 8.0 (8.96) | 1 | | | | | | | | | | | 3 | | 1 | 1 | | 2 | | 1 | 1 |
| 40 | 8.0 (8.96) | 1 | | | | | | | | | | | 4 | | 4 | 4 | | 3 | | 4 | 4 |
| | 4.0 (4.48) | 1 | 1 | 1 | 1 | 3 | 2 | 2 | 3 | 1 | 3 | 5 | 5 | 4 | 5 | 5 | 1 | 3 | 4 | 3 | 2 |
| | 2.0 (2.24) | 1 | 1 | 1 | 1 | 2 | 3 | 2 | 5 | 3 | 3 | 4 | 4 | 2 | 5 | 4 | 3 | 4 | 2 | 1 | 1 |
| | 1.0 (1.12) | 1 | 1 | 1 | 1 | 3 | 3 | 1 | 2 | 1 | 1 | 4 | 3 | 2 | 4 | 4 | 1 | 2 | 2 | 1 | 2 |
| | 1.0 (1.12) | 1 | 1 | 1 | 1 | 1 | 3 | 3 | 3 | 2 | 2 | | 4 | 3 | | 4 | 1 | 4 | 2 | 3 | 2 |
| | 0.50 (0.56) | 1 | 1 | 1 | 1 | | 2 | 2 | 1 | 1 | 1 | | 4 | 2 | | 2 | 2 | 1 | 1 | 1 | 1 |
| | 0.25 (0.28) | 1 | 1 | 1 | 1 | | 1 | 1 | 1 | 1 | 1 | | 2 | 1 | | 1 | 2 | 1 | 1 | 1 | 1 |
| 41 | 8.0 (8.96) | | | | | | | | | 2 | 1 | | 1 | 1 | 1 | 1 | 1 | 1 | | 1 | 1 |
| 42 | 8.0 (8.96) | 3 | | | | | | | | | | | 4 | | 5 | 4 | | 4 | | 2 | 4 |
| | 4.0 (4.48) | 1 | 1 | 1 | 2 | 3 | 4 | 2 | 5 | 3 | 2 | 5 | 5 | 4 | 4 | 4 | 3 | 5 | 2 | 4 | 2 |
| | 2.0 (2.24) | 1 | 1 | 1 | 1 | 2 | 4 | 1 | 2 | 1 | 2 | 5 | 4 | 2 | 2 | 4 | 2 | | 1 | 2 | 2 |
| | 1.0 (1.12) | 1 | 1 | 1 | 1 | 2 | 2 | 1 | 2 | 1 | 2 | 5 | 4 | 2 | 3 | 4 | 2 | 3 | 2 | 3 | 1 |
| | 1.0 (1.12) | 1 | 1 | 1 | 1 | 2 | 2 | 1 | 1 | 1 | 1 | 1 | 1 | 1 | 1 | 1 | 1 | 1 | 1 | 1 | 1 |
| | 0.5 (0.56) | 1 | 1 | 1 | 1 | 1 | 1 | 1 | 1 | 1 | 1 | 1 | 1 | 1 | 1 | 1 | 1 | 1 | 1 | 1 | 1 |
| | 0.25 (0.28) | 1 | 1 | 1 | 1 | 1 | 1 | 1 | 1 | 1 | 1 | 1 | 1 | 1 | 1 | 1 | 1 | 1 | 1 | 1 | 1 |
| 43 | 8.0 (8.96) | 2 | | | | | | | | | | | 4 | | 4 | 3 | | 4 | | 3 | 3 |
| | 4.0 (4.48) | 1 | 1 | 1 | 1 | 2 | 2 | 1 | 4 | 1 | 1 | 4 | 4 | 2 | 4 | 2 | 1 | 2 | 1 | 1 | 1 |
| | 2.0 (2.24) | 1 | 1 | 1 | 1 | 1 | 3 | 1 | 2 | 1 | 1 | 3 | 3 | 2 | 3 | 2 | 1 | 2 | 1 | 1 | 1 |
| | 1.0 (1.12) | 1 | 1 | 1 | 1 | 1 | 1 | 1 | 1 | 1 | 1 | 3 | 1 | 2 | 3 | 1 | 1 | 1 | 1 | 1 | 1 |
| 44 | 8.0 (8.96) | 3 | | | | | | | | | | | 5 | | 5 | 4 | | 4 | | 3 | 3 |
| | 4.0 (4.48) | 1 | 1 | 1 | 1 | 3 | 3 | 2 | 4 | 4 | 1 | 5 | 4 | 4 | 5 | 3 | 1 | 3 | 1 | 3 | 3 |
| | 2.0 (2.24) | 1 | 1 | 1 | 1 | 1 | 1 | 1 | 1 | 1 | 1 | 3 | 3 | 2 | 3 | 2 | 1 | 2 | 1 | 1 | 1 |
| | 1.0 (1.12) | 1 | 1 | 1 | 1 | 1 | 1 | 1 | 1 | 1 | 1 | 1 | 1 | 1 | 1 | 1 | 1 | 1 | 1 | 1 | 1 |
| 45 | 8.0 (8.96) | | | | | | | | | 2 | 1 | | 4 | 2 | 2 | 3 | 1 | 2 | | 2 | 2 |
| 46 | 8.0 (8.96) | | | | | | | | | 2 | 2 | | 4 | 4 | 5 | 4 | 2 | 4 | | 2 | 2 |
| | 4.0 (4.48) | 3 | 2 | 2 | 1 | 5 | 4 | 2 | 5 | 4 | 3 | 4 | 4 | 4 | 5 | 4 | 3 | 5 | 4 | 5 | 4 |
| | 2.0 (2.24) | 1 | 2 | 2 | 1 | 5 | 4 | 2 | 5 | 4 | 3 | 4 | 4 | 4 | 5 | 3 | 3 | 4 | 2 | 3 | 3 |
| | 1.0 (1.12) | 1 | 1 | 1 | 1 | 4 | 4 | 2 | 3 | 2 | 2 | 5 | 4 | 4 | 4 | 3 | 2 | 4 | 3 | 1 | 4 |
| | 1.0 (1.12) | 2 | 2 | 1 | 1 | 4 | 4 | 2 | 4 | 3 | 2 | 5 | 4 | 4 | 4 | 4 | 1 | 4 | 2 | 1 | 3 |
| | 0.05 (0.56) | 1 | 1 | 1 | 1 | 3 | 3 | 2 | 2 | 2 | 1 | 4 | 2 | 3 | 3 | 3 | 1 | 3 | 2 | 1 | 2 |
| | 0.25 (0.28) | 1 | 1 | 1 | 1 | 2 | 2 | 1 | 2 | 1 | 1 | 5 | 3 | 2 | 2 | 3 | 1 | 2 | 1 | 1 | 1 |
| | 0.25 (0.28) | 1 | 1 | 1 | 1 | 1 | 3 | 2 | 2 | 1 | 1 | 3 | 3 | 3 | 2 | 2 | 1 | 1 | 1 | 1 | 2 |
| | 0.12 (0.14) | 1 | 1 | 1 | 1 | 1 | 1 | 2 | 1 | 1 | 1 | 2 | 2 | 1 | 1 | 2 | 1 | 1 | 1 | 2 | 1 |
| | 0.0625 (0.07) | 1 | 1 | 1 | 1 | 1 | 1 | 1 | 1 | 1 | 1 | 1 | 1 | 1 | 1 | 1 | 1 | 1 | 1 | 1 | 1 |
| 47 | 8.0 (8.96) | 2 | | | | | | | | | | | 5 | | 5 | 4 | | 4 | | 1 | 3 |
| | 4.0 (4.48) | 2 | 2 | 2 | 2 | 4 | 4 | 2 | 4 | 4 | 4 | 5 | 5 | 5 | 5 | 4 | 4 | 4 | 3 | 3 | 5 |
| | 2.0 (2.24) | 1 | 2 | 1 | 1 | 4 | 4 | 2 | 4 | 4 | 3 | 5 | 5 | 4 | 5 | 4 | 3 | 2 | 1 | 1 | 3 |
| | 1.0 (1.12) | 1 | 1 | 1 | 1 | 2 | 3 | 1 | 3 | 2 | 1 | 5 | 3 | 1 | 4 | 3 | 2 | 2 | 1 | 1 | 1 |
| | 1.0 (1.12) | 1 | 1 | 1 | 1 | 1 | 4 | 1 | 3 | 2 | 2 | 5 | 3 | 3 | 4 | 4 | 1 | 1 | 1 | 1 | 1 |
| | 0.50 (0.56) | 1 | 1 | 1 | 1 | 2 | 2 | 2 | 2 | 1 | 1 | 5 | 3 | 1 | 2 | 2 | 1 | 1 | 1 | 1 | 1 |
| | 0.25 (0.28) | 1 | 1 | 1 | 1 | 1 | 1 | 1 | 1 | 1 | 1 | 4 | 1 | 3 | 3 | 3 | 1 | 1 | 1 | 1 | 1 |
| 48 | 8.0 (8.96) | - | | | | | | | | 3 | 4 | | 5 | 3 | 4 | 4 | 3 | 4 | | 1 | 3 |
| | 1.0 (1.12) | 1 | 1 | 2 | 1 | 3 | 3 | 1 | 2 | 2 | 1 | 4 | 4 | 2 | 4 | 2 | 1 | 1 | 3 | 2 | 2 |
| | 0.5 (0.56) | 1 | 1 | 2 | 1 | 1 | 1 | 1 | 3 | 1 | 1 | 4 | 3 | 1 | 4 | 1 | 1 | 2 | 1 | 1 | 2 |
| | 0.25 (0.28) | 1 | 1 | 1 | 1 | 1 | 1 | 1 | 1 | 1 | 1 | 1 | 3 | 1 | 3 | 2 | 1 | 2 | 1 | 2 | 1 |
| 49 | 8.0 (8.96) | 1 | | | | | | | | | | | 2 | | 4 | 3 | | 2 | | 1 | 3 |

4,620,865

TABLE II-continued

Preemergence

| Example No. of Compound Tested | Rate of Appln. lbs/acre | (kg/ha) | Crops | | | | | | | | | Weeds | | | | | | | | | | |
|---|---|---|---|---|---|---|---|---|---|---|---|---|---|---|---|---|---|---|---|---|---|
| | | | A | B | C | D | E | F | G | H | I | J | K | L | M | N | O | P | Q | R | S | T |
| 50 | 8.0 | (8.96) | 2 | | | | | | | | | | | 4 | | 4 | 3 | | 2 | | 1 | 3 |
| | 4.0 | (4.48) | 1 | 2 | 1 | 2 | 2 | 3 | 1 | 2 | 1 | 2 | 4 | 3 | 3 | 4 | 2 | 1 | 1 | 1 | 1 | 2 |
| | 2.0 | (2.24) | 1 | 1 | 2 | 1 | 2 | 3 | 1 | 2 | 1 | 2 | 4 | 3 | 2 | 3 | 2 | 2 | 1 | 1 | 1 | 1 |
| | 1.0 | (1.12) | 1 | 1 | 1 | 1 | 1 | 2 | 1 | 1 | 1 | 1 | 1 | 1 | 1 | 2 | 1 | 1 | 1 | 1 | 1 | 1 |
| 51 | 8.0 | (8.96) | | | | | | | | | 1 | 1 | | 2 | 2 | 1 | 2 | 1 | 1 | | | 1 | 2 |
| 52 | 8.0 | (8.96) | | | | | | | | | 4 | 5 | | 5 | 5 | 5 | 5 | 3 | 5 | | 3 | 5 |
| | 4.0 | (4.48) | 2 | 2 | 2 | 2 | 4 | 5 | 2 | 5 | 5 | 3 | 5 | 4 | | 5 | 3 | 4 | 5 | 5 | 2 | 4 |
| | 2.0 | (2.24) | 2 | 2 | 2 | 1 | 4 | 5 | 2 | 3 | 2 | 2 | 5 | 4 | | 5 | 4 | 2 | 4 | 1 | 1 | 2 |
| | 1.0 | (1.12) | 1 | 1 | 1 | 2 | 3 | 4 | 1 | 3 | 2 | 2 | 5 | 2 | | 5 | 4 | 2 | 3 | 3 | 1 | 2 |
| | 1.0 | (1.12) | 1 | 1 | 1 | 1 | 2 | 3 | 1 | 2 | 1 | 2 | 5 | 4 | 2 | 4 | 2 | 1 | 3 | 1 | 1 | 3 |
| | 0.50 | (0.56) | 1 | 1 | 1 | 1 | 1 | 2 | 1 | 2 | 2 | 3 | 4 | 3 | 1 | 2 | 2 | 1 | 1 | 1 | 1 | 1 |
| | 0.25 | (0.28) | 1 | 1 | 1 | 1 | 1 | 1 | 1 | 2 | 1 | 1 | 2 | 2 | 1 | 2 | 1 | 1 | 1 | 1 | 1 | 1 |
| 53 | 8.0 | (8.96) | 1 | | | | | | | | | | | 4 | | 5 | 3 | | 1 | | | 1 | 1 |
| | 4.0 | (4.48) | 1 | 1 | 1 | 1 | 1 | 2 | 1 | 1 | 1 | 4 | 4 | 4 | 2 | 5 | 3 | 1 | 2 | 2 | 1 | 2 |
| | 2.0 | (2.24) | 1 | 1 | 1 | 1 | 1 | 2 | 1 | 1 | 1 | 3 | 4 | 4 | 2 | 4 | 1 | 1 | 1 | 1 | 1 | 1 |
| | 1.0 | (1.12) | 1 | 1 | 1 | 1 | 1 | 1 | 1 | 1 | 1 | 2 | 4 | 2 | 1 | 3 | 1 | 1 | 2 | 1 | 1 | 1 |
| 54 | 8.0 | (8.96) | 1 | | | | | | | | | | | 2 | | 2 | 2 | | 1 | | | 1 | 1 |
| 55 | 8.0 | (8.96) | 2 | | | | | | | | | | | 4 | | 4 | 4 | | 2 | | | 1 | 2 |
| | 4.0 | (4.48) | 1 | 1 | 1 | 1 | 2 | 4 | 2 | 3 | 3 | 3 | 4 | 4 | 2 | 4 | 4 | 1 | 3 | 2 | 2 | 4 |
| | 2.0 | (2.24) | 1 | 1 | 1 | 1 | 2 | 4 | 1 | 3 | 3 | 3 | 5 | 4 | 2 | 1 | 3 | 2 | 5 | 2 | 1 | 3 |
| | 1.0 | (1.12) | 1 | 1 | 1 | 1 | 1 | 4 | 1 | 2 | 1 | 1 | 5 | 4 | 2 | 1 | 2 | 2 | 3 | 1 | 1 | 3 |
| | 1.0 | (1.12) | 1 | 1 | 1 | 1 | 4 | 1 | 1 | 3 | 1 | 2 | 3 | 5 | 3 | | 3 | 1 | 2 | 1 | 1 | 2 |
| | 0.50 | (0.56) | 1 | 1 | 1 | 1 | 1 | 1 | 1 | 1 | 1 | 1 | 2 | 4 | 2 | | 2 | 1 | 2 | 1 | 1 | 1 |
| | 0.25 | (0.28) | 1 | 1 | 1 | 1 | 1 | 1 | 1 | 1 | 1 | 1 | 3 | 3 | 4 | 2 | 1 | 1 | 1 | 1 | 1 | 1 |
| 56 | 8.0 | (8.96) | 2 | | | | | | | | | | | 4 | 3 | | 3 | | 1 | | | 2 | 1 |
| 57 | 8.0 | (8.96) | 2 | | | | | | | | | | | 4 | 3 | | 3 | | 2 | | | 1 | 1 |
| 58 | 8.0 | (8.96) | | | | | | | | | 4 | 4 | | 5 | 3 | 5 | 4 | 3 | 5 | | 4 | 5 |
| | 4.0 | (4.48) | 1 | 2 | 2 | 1 | 4 | 4 | 2 | 3 | 1 | 3 | 4 | 3 | 3 | 4 | 4 | 1 | 4 | 2 | 1 | 5 |
| | 2.0 | (2.24) | 1 | 1 | 1 | 1 | 3 | 4 | 2 | 3 | 1 | 2 | 4 | 3 | 3 | 3 | 3 | 1 | 3 | 2 | 1 | 2 |
| | 1.0 | (1.12) | 1 | 1 | 1 | 1 | 1 | 1 | 1 | 2 | 1 | 1 | 4 | 2 | 1 | 3 | 3 | 1 | 1 | 1 | 1 | 1 |
| 59 | 8.0 | (8.96) | 1 | | | | | | | | | | | 4 | | 4 | 4 | | 3 | | | 1 | 3 |
| | 4.0 | (4.48) | 1 | 1 | 1 | 1 | 3 | 2 | 1 | 3 | 1 | 2 | 4 | 4 | 2 | 5 | 4 | 2 | 2 | 1 | 2 | 2 |
| | 2.0 | (2.24) | 1 | 1 | 1 | 1 | 1 | 2 | 1 | 1 | 1 | 1 | 3 | 4 | 2 | 5 | 4 | 1 | 1 | 2 | 2 | 2 |
| | 1.0 | (1.12) | 1 | 1 | 1 | 1 | 1 | 2 | 1 | 2 | 1 | 1 | 3 | 3 | 1 | 3 | 2 | 1 | | 2 | 2 | 3 |
| 60 | 8.0 | (8.96) | 1 | | | | | | | | | | | 4 | | 5 | 2 | | 3 | | | 2 | 3 |
| | 4.0 | (4.48) | 1 | 1 | 1 | 1 | 1 | 1 | 1 | 2 | 1 | 1 | 3 | 3 | 2 | 1 | 1 | 1 | 1 | 1 | 1 | 1 |
| | 2.0 | (2.24) | 1 | 1 | 1 | 1 | 1 | 1 | 1 | 1 | 1 | 1 | 1 | 1 | 1 | 1 | 1 | 1 | 1 | 1 | 1 | 1 |
| | 1.0 | (1.12) | 1 | 1 | 1 | 1 | 1 | 1 | 1 | 1 | 1 | 1 | 1 | 1 | 1 | 1 | 1 | 1 | 1 | 1 | 1 | 1 |
| 61 | 8.0 | (8.96) | 1 | | | | | | | | | | | 5 | | 5 | 4 | | 4 | | | 2 | 2 |
| | 4.0 | (4.48) | 1 | 1 | 1 | 1 | 2 | 3 | 2 | 2 | 1 | 1 | 2 | 3 | 2 | 2 | 2 | 1 | 1 | 1 | 1 | 1 |
| | 2.0 | (2.24) | 1 | 1 | 1 | 1 | 1 | 2 | 2 | 2 | 1 | 1 | 1 | 2 | 1 | 2 | 2 | 1 | 2 | 1 | 1 | 1 |
| | 1.0 | (1.12) | 1 | 1 | 1 | 1 | 1 | 2 | 1 | 1 | 1 | 1 | 1 | 2 | 1 | 1 | 1 | 1 | 1 | 1 | 1 | 1 |
| 62 | 8.0 | (8.96) | 2 | | | | | | | | | | | 5 | | 5 | 4 | | 3 | | | 3 | 3 |
| | 4.0 | (4.48) | 1 | 1 | 2 | 1 | 2 | 2 | 1 | 3 | 1 | 2 | 4 | 4 | 3 | 5 | 4 | 4 | 3 | 4 | 1 | 5 |
| | 2.0 | (2.24) | 1 | 1 | 2 | 1 | 2 | 2 | 1 | 2 | 1 | 1 | 4 | 4 | 2 | 5 | 4 | 3 | 3 | 2 | 2 | 4 |
| | 1.0 | (1.12) | 1 | 1 | 1 | 1 | 3 | 2 | 1 | 1 | 1 | 1 | 4 | 4 | 2 | 5 | 4 | 1 | 2 | 1 | 1 | 3 |
| | 1.0 | (1.12) | 1 | 1 | 1 | 3 | 4 | 2 | 2 | 3 | 3 | 1 | 4 | 4 | 4 | 4 | 2 | 2 | 2 | 1 | 1 | 2 |
| | 0.50 | (0.56) | 1 | 1 | 1 | 1 | 2 | 3 | 2 | 3 | 2 | 1 | 3 | 4 | 1 | 4 | 4 | 1 | 1 | 1 | 1 | 2 |
| | 0.25 | (0.28) | 1 | 1 | 1 | 1 | 1 | 1 | 1 | 1 | 1 | 1 | 3 | 1 | 2 | 2 | 1 | 1 | 1 | 1 | 1 | 1 |
| 63 | 8.0 | (8.96) | 1 | | | | | | | | | | | 4 | | 4 | 3 | | 5 | | 1 | 1 | 2 |
| | 4.0 | (4.48) | 1 | 1 | 2 | 1 | 2 | 3 | 1 | 3 | 1 | 1 | 4 | 4 | 3 | 5 | 3 | 1 | 2 | 2 | 1 | 2 |
| | 2.0 | (2.24) | 1 | 1 | 3 | 1 | 1 | 2 | 2 | 2 | 1 | 1 | 3 | 3 | 2 | 3 | 3 | 1 | 1 | 1 | 1 | 1 |
| | 1.0 | (1.12) | 1 | 1 | 1 | 1 | 2 | 1 | 1 | 2 | 1 | 1 | 3 | 3 | 2 | 3 | 2 | 1 | 1 | 1 | 1 | 1 |
| 64 | 8.0 | (8.96) | | | | | | | | | 1 | 2 | | 1 | 2 | 2 | 3 | 1 | 4 | | | 1 | 2 |
| 65 | 8.0 | (8.96) | | | | | | | | | 1 | 1 | | 3 | 2 | 3 | 3 | 1 | 1 | | | 1 | 1 |
| 66 | 8.0 | (8.96) | 3 | | | | | | | | | | | 5 | | 5 | 5 | | 5 | | | 2 | 3 |
| | 4.0 | (4.48) | 2 | 1 | 3 | 2 | 5 | 5 | 2 | 4 | 5 | 4 | 5 | 5 | 3 | 5 | 4 | 3 | 5 | 3 | 1 | 3 |
| | 2.0 | (2.24) | 1 | 1 | 1 | 1 | 3 | 5 | 1 | 3 | 4 | 3 | 5 | 5 | 3 | 5 | 4 | 3 | 4 | 2 | 1 | 2 |
| | 1.0 | (1.12) | 1 | 1 | 1 | 1 | 4 | 4 | 1 | 3 | 2 | 1 | 4 | 4 | 3 | 5 | 4 | 1 | 1 | 1 | 1 | 2 |
| | 1.0 | (1.12) | 1 | 1 | 1 | 1 | 3 | 3 | 1 | 1 | 4 | 1 | 3 | 4 | 1 | 3 | 1 | 1 | 3 | 1 | 1 | 1 |
| | 0.50 | (0.56) | 1 | 1 | 1 | 1 | 1 | 1 | 2 | 1 | 1 | 1 | 4 | 1 | 4 | 1 | 1 | 2 | 1 | 1 | 1 | 1 |
| | 0.25 | (0.28) | 1 | 1 | 1 | 1 | 1 | 1 | 1 | 1 | 1 | 1 | 1 | 1 | 1 | 4 | 1 | 1 | 1 | 1 | 1 | 1 |
| 67 | 8.0 | (8.96) | 2 | | | | | | | | | | | 4 | | 4 | 3 | | 3 | | 3 | 3 | 3 |
| | 4.0 | (4.48) | 1 | 1 | 1 | 2 | 4 | 5 | 2 | 3 | 3 | 2 | 4 | 4 | 3 | 5 | 4 | 2 | 4 | 2 | 2 | 3 |
| | 2.0 | (2.24) | 1 | 2 | 1 | 2 | 2 | 4 | 1 | 4 | 2 | 1 | 4 | 2 | 1 | 5 | 3 | 1 | 1 | 1 | 1 | 2 |
| | 1.0 | (1.12) | 1 | 1 | 1 | 1 | 1 | 3 | 1 | 2 | 1 | 1 | 3 | 1 | 1 | 2 | 1 | 1 | 1 | 1 | 1 | 1 |
| 68 | 8.0 | (8.96) | | | | | | | | | 3 | 2 | | 3 | 4 | 4 | 4 | 1 | 4 | | | 2 | 2 |
| | 4.0 | (4.48) | 1 | 1 | 1 | 1 | 1 | 1 | 2 | 1 | 1 | 2 | 4 | 3 | 3 | 4 | 2 | 2 | 2 | 1 | 2 | 2 |
| | 2.0 | (2.24) | 1 | 2 | 1 | 1 | 1 | 2 | 2 | 2 | 1 | 1 | 4 | 3 | 2 | 3 | 3 | 2 | 1 | 1 | 2 | 2 |
| | 1.0 | (1.12) | 1 | 1 | 1 | 1 | 1 | 1 | 1 | 1 | 1 | 1 | 4 | 1 | 1 | 2 | 3 | 2 | 1 | 1 | 2 | 2 |
| 69 | 8.0 | (8.96) | | | | | | | | | 1 | 1 | | 1 | 1 | 1 | 1 | 1 | 1 | | | 1 | 1 |
| 70 | 8.0 | (8.96) | 2 | | | | | | | | | | | 5 | | 5 | 5 | | 5 | | | 3 | 4 |
| | 4.0 | (4.48) | 2 | 1 | 1 | 1 | 3 | 4 | 2 | 4 | 4 | 3 | 5 | 5 | 4 | 4 | 4 | 2 | 5 | 4 | 1 | 2 |
| | 2.0 | (2.24) | 1 | 4 | 2 | 1 | 2 | 4 | 2 | 4 | 3 | 3 | 5 | 5 | 4 | 5 | 4 | 2 | 5 | 5 | 3 | 4 |
| | 1.0 | (1.12) | 1 | 1 | 1 | 1 | 2 | 3 | 1 | 1 | 3 | 2 | 4 | 4 | 1 | 4 | 3 | 1 | 4 | 3 | 1 | 1 |
| | 1.0 | (1.12) | 1 | 2 | 1 | 1 | 1 | 3 | 2 | 1 | 1 | 3 | 5 | 4 | 3 | 4 | 1 | 1 | 4 | 3 | 3 | 2 |

TABLE II-continued

Preemergence

| Example No. of Compound Tested | Rate of Appln. lbs/acre | (kg/ha) | Crops | | | | | | | | | Weeds | | | | | | | | | | |
|---|---|---|---|---|---|---|---|---|---|---|---|---|---|---|---|---|---|---|---|---|---|---|
| | | | A | B | C | D | E | F | G | H | I | J | K | L | M | N | O | P | Q | R | S | T |
| | 0.50 | (0.56) | 1 | 1 | 1 | 1 | 1 | 1 | 1 | 1 | 1 | 1 | 2 | 2 | 1 | 1 | 1 | 1 | 2 | 1 | 1 | 1 |
| | 0.25 | (0.28) | 1 | 1 | 1 | 1 | 1 | 1 | 1 | 1 | 1 | 1 | 1 | 1 | 1 | 1 | 1 | 1 | 3 | 1 | 1 | 1 |
| 71 | 8.0 | (8.96) | 1 | | | | | | | | | | | 3 | | 4 | 1 | | 1 | | | 2 | 1 |
| 72 | 8.0 | (8.96) | 2 | | | | | | | | | | | 4 | | 5 | 3 | | 4 | | | 4 | 4 |
| | 4.0 | (4.48) | 1 | 1 | 1 | 1 | | 4 | 2 | 3 | 1 | 1 | | 4 | 3 | | 4 | 1 | 3 | 1 | 2 | 3 |
| | 2.0 | (2.24) | 1 | 1 | 1 | 1 | | 4 | 2 | 2 | 1 | 1 | | 4 | 4 | | 4 | 1 | 2 | 1 | 2 | 2 |
| | 1.0 | (1.12) | 1 | 1 | 1 | 1 | 1 | 1 | 1 | 1 | 2 | 1 | | 3 | 2 | | 1 | 1 | 1 | 1 | 1 | 1 |
| 73 | 8.0 | (8.96) | 1 | | | | | | | | | | | 4 | | 4 | 4 | | 2 | | | 1 | 2 |
| | 4.0 | (4.48) | 1 | 1 | 2 | 1 | | 4 | 2 | 4 | 2 | 3 | | 5 | 3 | | 4 | 2 | 4 | 2 | 3 | 2 |
| | 2.0 | (2.24) | 1 | 1 | 1 | 1 | | 3 | 2 | 2 | 3 | 3 | | 4 | 2 | | 3 | 2 | 2 | 1 | 2 | 2 |
| | 1.0 | (1.12) | 1 | 1 | 1 | 1 | 1 | 1 | 1 | 1 | 1 | 1 | | 3 | 2 | 2 | 2 | 1 | 1 | 1 | 1 | 1 |
| 74 | 8.0 | (8.96) | 1 | | | | | | | | | | | 5 | | 5 | 3 | | 5 | | | 2 | 2 |
| | 4.0 | (4.48) | 1 | 1 | 2 | 1 | 1 | 4 | 1 | 2 | 2 | 1 | 5 | 4 | 3 | 3 | 3 | 1 | 3 | 2 | 2 | 1 |
| | 2.0 | (2.24) | 1 | 1 | 2 | 1 | 1 | 3 | 1 | 2 | 1 | 1 | 4 | 4 | 2 | 3 | 3 | 1 | 3 | 1 | 2 | 1 |
| | 1.0 | (1.12) | 1 | 1 | 1 | 1 | 1 | 3 | 1 | 2 | 1 | 1 | 4 | 4 | 2 | 2 | 2 | 1 | 2 | 1 | 2 | 2 |
| | 1.0 | (1.12) | 1 | 1 | 1 | 1 | 1 | 1 | 1 | 1 | 1 | 1 | 1 | 1 | 1 | 1 | 1 | 1 | 1 | 1 | 1 | 1 |
| | 0.50 | (0.56) | 1 | 1 | 1 | 1 | 1 | 1 | 1 | 1 | 1 | 1 | 1 | 1 | 1 | 1 | 1 | 1 | 1 | 1 | 1 | 1 |
| | 0.25 | (0.28) | 1 | 1 | 1 | 1 | 1 | 1 | 1 | 1 | 1 | 1 | 1 | 1 | 1 | 1 | 1 | 1 | 1 | 1 | 1 | 1 |
| 75 | 8.0 | (8.96) | | | | | | | | | 4 | 1 | | 4 | 2 | 3 | 4 | 1 | 4 | | | 2 | 2 |
| | 4.0 | (4.48) | 1 | 2 | 2 | 1 | 2 | 4 | 1 | 1 | 1 | 1 | 4 | 2 | 3 | 3 | 3 | 1 | 3 | 2 | 2 | 2 |
| | 2.0 | (2.24) | 1 | 1 | 1 | 1 | 2 | 1 | 1 | 1 | 1 | 1 | 4 | 2 | 2 | 3 | 3 | 1 | 3 | 2 | 1 | 1 |
| | 1.0 | (1.12) | 1 | 1 | 1 | 1 | 1 | 1 | 1 | 1 | 1 | 1 | 3 | 1 | 1 | 1 | 2 | 1 | 1 | 1 | 1 | 1 |
| 76 | 8.0 | (8.96) | | | | | | | | | 4 | 3 | | 4 | 3 | 3 | 4 | 2 | 5 | | | 2 | 3 |
| | 4.0 | (4.48) | 3 | 2 | 2 | 1 | 4 | 4 | 2 | 5 | 3 | 3 | 5 | 4 | 4 | 5 | 4 | 1 | 5 | 4 | 2 | 3 |
| | 2.0 | (2.24) | 1 | 1 | 2 | | 1 | 4 | 2 | 2 | 2 | 2 | 5 | 4 | 4 | 4 | 3 | 1 | 5 | 3 | 2 | 4 |
| | 1.0 | (1.12) | 1 | 1 | 1 | 1 | 2 | 2 | 1 | 1 | 1 | 1 | 4 | 4 | 2 | 3 | 1 | 1 | 2 | 2 | 1 | 1 |
| | 1.0 | (1.12) | 1 | 1 | 1 | 1 | 3 | 3 | 1 | 2 | 1 | 1 | 4 | 3 | 2 | 3 | 3 | 1 | 1 | 1 | 1 | 1 |
| | 0.50 | (0.56) | 1 | 1 | 1 | 1 | 2 | 2 | 1 | 1 | 1 | 1 | 1 | 2 | 1 | 2 | 1 | 1 | 1 | 1 | 1 | 1 |
| | 0.25 | (0.28) | 1 | 1 | 1 | 1 | 1 | 1 | 1 | 1 | 1 | 1 | 2 | 1 | 1 | 2 | 1 | 1 | 1 | 1 | 1 | 1 |
| 77 | 8.0 | (8.96) | | | | | | | | | 4 | 3 | | 5 | 3 | 5 | 4 | 3 | 4 | | | 2 | 4 |
| | 4.0 | (4.48) | 2 | 3 | 3 | 2 | 5 | 4 | 2 | 4 | 2 | 2 | 4 | 5 | 4 | 5 | 4 | 4 | 4 | 3 | 4 | 3 |
| | 2.0 | (2.24) | 2 | 2 | 1 | 1 | 5 | 3 | 3 | 4 | 3 | 3 | 4 | 4 | 4 | 5 | 5 | 3 | 4 | 3 | 4 | 3 |
| | 1.0 | (1.12) | 1 | 1 | 2 | 1 | 4 | 4 | 2 | 4 | 2 | 1 | 5 | 4 | 3 | 4 | 4 | 1 | 3 | 3 | 1 | 3 |
| | 1.0 | (1.12) | 1 | 1 | 2 | 2 | 5 | 4 | 2 | 3 | 3 | 2 | 4 | 4 | 4 | 5 | 3 | 2 | 5 | 2 | 2 | 4 |
| | 0.50 | (0.56) | 1 | 1 | 1 | 1 | 4 | 4 | 1 | 3 | 2 | 2 | 3 | 4 | 2 | 3 | 3 | 1 | 4 | 2 | 2 | 2 |
| | 0.25 | (0.28) | 1 | 1 | 1 | 1 | 2 | 2 | 1 | 2 | 1 | 1 | 4 | 4 | 3 | 3 | 1 | 1 | 4 | 2 | 1 | 2 |
| | 0.25 | (0.28) | 1 | 1 | 1 | 1 | 2 | 4 | 2 | 3 | 2 | 1 | 3 | 3 | 2 | 4 | 2 | 1 | 2 | 1 | 2 | 1 |
| | 0.125 | (0.14) | 1 | 1 | 1 | 1 | 1 | 1 | 1 | 1 | 1 | 1 | 3 | 3 | 3 | 1 | 1 | 1 | 2 | 1 | 2 | 2 |
| | 0.0625 | (0.07) | 1 | 1 | 1 | 1 | 1 | 1 | 1 | 1 | 1 | 1 | 1 | 2 | 1 | 1 | 2 | 1 | 1 | 1 | 1 | 2 |
| 78 | 8.0 | (8.96) | | | | | | | | | 1 | 1 | | 4 | 2 | 2 | 3 | 1 | 2 | | | 1 | 1 |
| 79 | 8.0 | (8.96) | | | | | | | | | 2 | 2 | | 3 | 4 | 5 | 3 | 2 | 2 | | | 1 | 2 |
| | 4.0 | (4.48) | 1 | 1 | 1 | 1 | 1 | 3 | 1 | 1 | 1 | 1 | 5 | 2 | 3 | 3 | 3 | 1 | 1 | 1 | 1 | 1 |
| | 2.0 | (2.24) | 1 | 1 | 1 | 1 | 1 | 2 | 1 | 1 | 1 | 1 | 5 | 2 | 2 | 2 | 1 | 1 | 1 | 1 | 1 | 1 |
| | 1.0 | (1.12) | 1 | 1 | 1 | 1 | 1 | 1 | 1 | 1 | 1 | 1 | 1 | 1 | 1 | 1 | 1 | 1 | 1 | 1 | 1 | 1 |
| 80 | 8.0 | (8.96) | | | | | | | | | 4 | 1 | | 4 | 4 | 5 | 4 | 3 | 2 | | 3 | | |
| | 4.0 | (4.48) | 1 | 1 | 1 | 1 | 2 | 1 | 1 | 1 | 1 | 1 | 2 | 2 | 2 | 3 | 1 | 2 | 4 | 1 | 1 | 2 |
| | 2.0 | (2.24) | 1 | 1 | 1 | 1 | 1 | 2 | 1 | 1 | 1 | 1 | 1 | 2 | 3 | 3 | 1 | 1 | 2 | 1 | 1 | 2 |
| | 1.0 | (1.12) | 1 | 1 | 1 | 1 | 1 | 1 | 1 | 1 | 1 | 1 | 1 | 1 | 1 | 1 | 2 | 1 | 1 | 1 | 1 | 1 |
| 82 | 8.0 | (8.96) | | | | | | | | | 4 | 2 | | 4 | 4 | 2 | 5 | 2 | 5 | | | 2 | 5 |
| | 4.0 | (4.48) | 2 | 1 | 1 | 1 | 3 | 3 | 1 | 5 | 4 | 2 | 3 | 3 | 4 | 3 | 4 | 1 | 4 | 2 | 2 | 2 |
| | 2.0 | (2.24) | 2 | 1 | 1 | 1 | 3 | 2 | 1 | 4 | 4 | 3 | 2 | 2 | 4 | 2 | 4 | 1 | 3 | 1 | 1 | 2 |
| | 1.0 | (1.12) | 1 | 1 | 1 | 1 | 1 | 2 | 1 | 2 | 2 | 1 | 1 | 2 | 3 | 2 | 2 | 1 | 1 | 1 | 2 | 2 |
| 83 | 8.0 | (8.96) | | | | | | | | | 1 | 1 | | 2 | 2 | 2 | 1 | 1 | 1 | | | 1 | 1 |
| 84 | 8.0 | (8.96) | | | | | | | | | 1 | 1 | | 3 | 1 | 4 | 3 | 2 | 3 | | | 2 | 3 |
| 85 | 8.0 | (8.96) | | | | | | | | | 5 | 4 | | 5 | 5 | 5 | 5 | 3 | 5 | | | 3 | 5 |
| | 4.0 | (4.48) | 1 | 3 | 2 | 2 | 4 | 3 | 2 | 5 | 3 | 1 | 5 | 5 | 5 | 5 | 4 | 1 | 4 | 2 | 3 | 5 |
| | 2.0 | (2.24) | 1 | 2 | 2 | 1 | 3 | 3 | 2 | 4 | 1 | 1 | 5 | 4 | 5 | 5 | 2 | 1 | 2 | 1 | 2 | 2 |
| | 1.0 | (1.12) | 1 | 1 | 1 | 1 | 1 | 3 | 1 | 2 | 2 | | 4 | 3 | 4 | 4 | 2 | 1 | 1 | 1 | 1 | 1 |
| | 1.0 | (1.12) | 1 | 1 | 1 | 1 | 2 | 3 | 1 | 2 | 1 | 1 | 4 | 2 | 2 | 3 | 2 | 1 | 2 | 1 | 1 | 2 |
| | 0.5 | (0.56) | 1 | 1 | 1 | 1 | 2 | 2 | 2 | 2 | 1 | 1 | 2 | 1 | 2 | 2 | 1 | 1 | 1 | 1 | 1 | 1 |
| | 0.25 | (0.28) | 1 | 1 | 1 | 1 | 1 | 1 | 1 | 1 | 1 | 1 | 1 | 1 | 1 | 1 | 1 | 1 | 1 | 1 | 1 | 1 |
| 86 | 8.0 | (8.96) | | | | | | | | | 4 | 3 | | 4 | 4 | 4 | 4 | 2 | 5 | | | 4 | 5 |
| | 4.0 | (4.48) | 2 | 5 | 5 | 2 | 4 | 4 | 1 | 4 | 5 | 4 | 5 | 4 | 5 | 5 | 5 | 4 | 4 | 5 | 3 | 5 |
| | 2.0 | (2.24) | 1 | 1 | 2 | 1 | 2 | 4 | 2 | 3 | 5 | 2 | 4 | 4 | 4 | 4 | 5 | 3 | 3 | 2 | 3 | 2 |
| | 1.0 | (1.12) | 1 | 1 | 1 | 1 | 2 | 3 | 1 | 5 | 5 | 2 | 5 | 4 | 4 | 4 | 5 | 1 | 2 | 5 | 1 | 2 |
| | 1.0 | (1.12) | 1 | 1 | 1 | 1 | 1 | 1 | 1 | 1 | 1 | 1 | 3 | 1 | 3 | 2 | 1 | 1 | 1 | 3 | 1 | 1 |
| | 0.5 | (0.56) | 1 | 1 | 1 | 1 | 3 | 1 | 1 | 2 | 1 | 1 | 4 | 2 | 3 | 1 | 1 | 1 | 1 | 2 | 1 | 5 |
| | 0.25 | (0.28) | 1 | 1 | 1 | 1 | 3 | 1 | 1 | 1 | 1 | 1 | 1 | 1 | 1 | 1 | 1 | 1 | 1 | 1 | 1 | 1 |
| 87 | 8.0 | (8.96) | | | | | | | | | 5 | 3 | | 5 | 5 | 5 | 4 | 4 | 4 | | | 4 | 4 |
| | 2.0 | (2.24) | 1 | 2 | 2 | 2 | 2 | 4 | 2 | 3 | 3 | 4 | 4 | 4 | 4 | 5 | 5 | 2 | 5 | 4 | 1 | 4 |
| | 1.0 | (1.12) | 1 | 1 | 1 | 1 | 2 | 2 | 2 | 2 | 2 | 1 | 4 | 4 | 4 | 4 | 2 | 3 | 1 | 1 | 2 |
| | 1.0 | (1.12) | 1 | 1 | 1 | 1 | 3 | 2 | 1 | 1 | 1 | 1 | 4 | 2 | 2 | 3 | 3 | 1 | 4 | 2 | 1 | 3 |
| | 0.5 | (0.56) | 1 | 2 | 1 | 1 | 2 | 2 | 1 | 2 | 1 | 1 | 2 | 4 | 1 | 4 | 4 | 1 | 2 | 1 | 1 | 1 |
| | 0.5 | (0.56) | 1 | 1 | 1 | 1 | 2 | 2 | 1 | 1 | 1 | 1 | 1 | 1 | 1 | 3 | 1 | 1 | 2 | 1 | 1 | 1 |
| | 0.25 | (0.28) | 1 | 1 | 1 | 1 | 1 | 1 | 1 | 1 | 1 | 1 | 1 | 1 | 1 | 1 | 1 | 1 | 1 | 1 | 1 | 1 |
| 88 | 8.0 | (8.96) | | | | | | | | | 4 | 3 | 5 | 5 | 5 | 5 | 5 | 5 | 5 | | | 5 | 5 |

TABLE II-continued

Preemergence

| Example No. of Compound Tested | Rate of Appln. lbs/acre (kg/ha) | | Crops | | | | | | | | | Weeds | | | | | | | | | |
|---|---|---|---|---|---|---|---|---|---|---|---|---|---|---|---|---|---|---|---|---|---|
| | | | A | B | C | D | E | F | G | H | I | J | K | L | M | N | O | P | Q | R | S | T |
| | 4.0 | (4.48) | 1 | 2 | 2 | 1 | 5 | 5 | 3 | 5 | 4 | 4 | 5 | 5 | 4 | 5 | 4 | 2 | 5 | 4 | 4 | 5 |
| | 2.0 | (2.24) | 1 | 1 | 1 | 1 | 4 | 4 | 1 | 3 | 2 | 2 | 5 | 4 | 3 | 5 | 4 | 1 | 4 | 2 | 2 | 2 |
| | 1.0 | (1.12) | 1 | 1 | 1 | 1 | 3 | 3 | 1 | 2 | 1 | 1 | 4 | 4 | 2 | 4 | 4 | 1 | 3 | 1 | 1 | 1 |
| | 1.0 | (1.12) | 1 | 1 | 1 | 1 | 4 | 3 | 1 | 2 | 2 | 3 | 2 | 3 | 4 | 4 | 3 | 2 | 3 | 1 | 1 | 1 |
| | 0.5 | (0.56) | 1 | 1 | 1 | 1 | 3 | 3 | 1 | 1 | 1 | 1 | 1 | 1 | 1 | 1 | 1 | 1 | 1 | 1 | 1 | 1 |
| | 0.25 | (0.28) | 1 | 1 | 1 | 1 | 3 | 3 | 1 | 1 | 2 | 1 | 2 | 1 | 1 | 2 | 1 | 1 | 1 | 1 | 1 | 1 |
| 89 | 8.0 | (8.96) | | | | | | | | | 3 | 3 | | 3 | 3 | 4 | 4 | 4 | 4 | | | 3 | 5 |
| | 4.0 | (4.48) | 1 | 1 | 1 | 1 | 3 | 2 | 2 | 4 | 1 | 1 | 5 | 4 | 4 | 4 | 2 | 2 | 2 | 1 | 1 | 2 |
| | 2.0 | (2.24) | 1 | 1 | 1 | 1 | 1 | 2 | 1 | 2 | 1 | 1 | 4 | 5 | 4 | 5 | 2 | 1 | 4 | 2 | 1 | 3 |
| | 1.0 | (1.12) | 1 | 1 | 1 | 1 | 1 | 1 | 1 | 1 | 1 | 1 | 1 | 2 | 2 | 3 | 2 | 1 | 1 | 1 | 1 | 1 |
| 90 | 8.0 | (8.96) | | | | | | | | | 1 | 1 | | 4 | 4 | 4 | 4 | 2 | 3 | | | 1 | 1 |
| | 4.0 | (4.48) | 1 | 1 | 1 | 1 | 1 | 1 | 1 | 1 | 1 | 1 | 1 | 3 | 1 | 4 | 2 | 1 | 1 | 1 | 1 | 1 |
| | 2.0 | (2.24) | 1 | 1 | 1 | 1 | 1 | 1 | 1 | 1 | 1 | 1 | 1 | 1 | 1 | 1 | 1 | 1 | 1 | 1 | 1 | 1 |
| | 1.0 | (1.12) | 1 | 1 | 1 | 1 | 1 | 1 | 1 | 1 | 1 | 1 | 1 | 1 | 1 | 1 | 1 | 1 | 1 | 1 | 1 | 1 |
| 91 | 8.0 | (8.96) | | | | | | | | | 4 | 4 | | 5 | 3 | 5 | 5 | 2 | 5 | | | 3 | 3 |
| | 4.0 | (4.48) | 1 | 3 | 2 | 1 | 5 | 5 | 2 | 3 | 5 | 4 | 5 | 5 | 5 | 5 | 5 | 2 | 4 | 2 | 2 | 4 |
| | 2.0 | (2.24) | 1 | 1 | 2 | 1 | 4 | 4 | 2 | 3 | 4 | 3 | 5 | 5 | 5 | 5 | 3 | 5 | 2 | 2 | 2 | 4 |
| | 1.0 | (1.12) | 1 | 1 | 1 | 1 | 3 | 4 | 1 | 4 | 2 | 1 | 4 | 4 | 3 | 4 | 4 | 1 | 3 | 1 | 2 | 4 |
| | 1.0 | (1.12) | 1 | 1 | 1 | 1 | 4 | 4 | 1 | 1 | 3 | 1 | 3 | 3 | 3 | 4 | 3 | 1 | 4 | 1 | 1 | 2 |
| | 0.5 | (0.56) | 1 | 2 | 1 | 1 | 1 | 3 | 1 | 3 | 2 | 1 | 3 | 3 | 4 | 4 | 3 | 1 | 4 | 1 | 1 | 3 |
| | 0.25 | (0.28) | 1 | 1 | 1 | 1 | 1 | 1 | 1 | 1 | 1 | 1 | 1 | 1 | 1 | 3 | 2 | 1 | 1 | 1 | 1 | 1 |
| 92 | 8.0 | (8.96) | | | | | | | | | 2 | 4 | | 3 | 3 | 5 | 4 | 2 | 4 | | | 2 | 3 |
| | 4.0 | (4.48) | 1 | 1 | 2 | 1 | 2 | 3 | 2 | 4 | 2 | 1 | 4 | 4 | 2 | 5 | 4 | 2 | 4 | 2 | 4 | 4 |
| | 2.0 | (2.24) | 1 | 1 | 2 | 1 | 2 | 3 | 2 | 4 | 2 | 1 | 4 | 4 | 2 | 5 | 4 | 1 | 2 | 2 | 2 | 2 |
| | 1.0 | (1.12) | 1 | 1 | 1 | 1 | 2 | 2 | 2 | 3 | 2 | 1 | 1 | 3 | 1 | 3 | 3 | 1 | 1 | 1 | 1 | 1 |
| 93 | 8.0 | (8.96) | | | | | | | | | 4 | 2 | | 2 | 4 | 5 | 4 | 2 | 5 | | | 2 | 3 |
| | 4.0 | (4.48) | 1 | 1 | 1 | 1 | 2 | 1 | 1 | 1 | 1 | 1 | 2 | 3 | 2 | 2 | 2 | 1 | 1 | 1 | 1 | 2 |
| | 2.0 | (2.24) | 1 | 1 | 1 | 1 | 1 | 1 | 1 | 1 | 1 | 1 | 1 | 1 | 1 | 2 | 1 | 1 | 1 | 1 | 1 | 1 |
| | 1.0 | (1.12) | 1 | 1 | 1 | 1 | 1 | 1 | 1 | 1 | 1 | 1 | 3 | 2 | 2 | 3 | 1 | 1 | 1 | 1 | 1 | 1 |
| 94 | 8.0 | (8.96) | | | | | | | | | 3 | 2 | | 2 | 3 | 5 | 2 | 3 | 5 | | | 2 | 5 |
| | 4.0 | (4.48) | 1 | 2 | 2 | 1 | 1 | 2 | 2 | 3 | 2 | 1 | 2 | 1 | 3 | 2 | 2 | 1 | 2 | 2 | 2 | 1 |
| | 2.0 | (2.24) | 1 | 2 | 1 | 1 | 1 | 2 | 2 | 2 | 2 | | | | | | | | | | | | |
| | 1.0 | (1.12) | 1 | 1 | 1 | 1 | 1 | 1 | 2 | 2 | 1 | 1 | 2 | 1 | 2 | 1 | 1 | 1 | 2 | 1 | 1 | 1 |
| 95 | 8.0 | (8.96) | | | | | | | | | 5 | 5 | | 5 | 5 | 5 | 5 | 4 | 5 | | | 5 | 5 |
| | 4.0 | (4.48) | 3 | 5 | 4 | 4 | 5 | 5 | 3 | 5 | 5 | 5 | 5 | 5 | 5 | 5 | 5 | 5 | 5 | 5 | 5 | 5 |
| | 2.0 | (2.24) | 1 | 4 | 3 | 3 | 5 | 5 | 3 | 4 | 4 | 4 | 5 | 5 | 4 | 5 | 5 | 4 | 5 | 5 | 4 | 5 |
| | 1.0 | (1.12) | 1 | 2 | 1 | 2 | 5 | 5 | 2 | 4 | 4 | 4 | 5 | 5 | 1 | 5 | 5 | 3 | 5 | 5 | 4 | 4 |
| | 1.0 | (1.12) | 1 | 1 | 1 | 1 | 5 | 5 | 2 | 2 | 2 | 1 | 5 | 5 | 1 | 5 | 4 | 2 | 5 | 3 | 4 | 3 |
| | 0.5 | (0.56) | 1 | 1 | 1 | 1 | 5 | 4 | 1 | 2 | 2 | 1 | 5 | 4 | 1 | 4 | 3 | 2 | 4 | 4 | 3 | 1 |
| | 0.25 | (0.28) | 1 | 1 | 1 | 1 | 4 | 4 | 1 | 2 | 2 | 1 | 5 | 3 | 1 | 4 | 1 | 1 | 1 | 1 | 1 | 1 |
| 96 | 8.0 | (8.96) | | | | | | | | | 4 | 4 | | 5 | 4 | 5 | 5 | 2 | 5 | | | 4 | 4 |
| | 4.0 | (4.48) | 1 | 3 | 2 | 1 | 5 | 5 | 2 | 3 | 3 | 2 | 5 | 4 | 3 | 5 | 4 | 2 | 4 | 2 | 3 | 4 |
| | 2.0 | (2.24) | 1 | 1 | 1 | 1 | 5 | 4 | 1 | 2 | 2 | | | | | | | | | | | | |
| | 1.0 | (1.12) | 1 | 1 | 1 | 1 | 3 | 3 | 1 | 2 | 1 | 1 | 5 | 3 | 2 | 3 | 2 | 1 | 1 | 2 | 1 | 1 |
| 97 | 8.0 | (8.96) | | | | | | | | | 5 | 5 | | 5 | 5 | 5 | 5 | 5 | 5 | | | 5 | 5 |
| | 4.0 | (4.48) | 3 | 4 | 5 | 4 | 5 | 5 | 4 | 5 | 5 | 5 | 5 | 5 | 5 | 5 | 5 | 5 | 5 | 5 | 5 | 5 |
| | 2.0 | (2.24) | 1 | 4 | 4 | 4 | 5 | 5 | 2 | 5 | 5 | 4 | 5 | 5 | 3 | 5 | 4 | 3 | 5 | 5 | 5 | 4 |
| | 1.0 | (1.12) | 2 | 2 | 2 | 3 | 5 | 5 | 3 | 4 | 3 | 4 | 5 | 5 | 2 | 5 | 5 | 2 | 5 | 4 | 4 | 4 |
| | 1.0 | (1.12) | 1 | 1 | 2 | 2 | 5 | 5 | 2 | 4 | 2 | 4 | 5 | 5 | 1 | 5 | 5 | 2 | 5 | 5 | 4 | 3 |
| | 0.5 | (0.56) | 1 | 1 | 2 | 1 | 5 | 5 | 2 | 3 | 2 | 1 | 5 | 5 | 1 | 5 | 5 | 1 | 5 | 5 | 3 | 3 |
| | 0.25 | (0.28) | 1 | 1 | 1 | 1 | 5 | 5 | 1 | 2 | 1 | 1 | 5 | 4 | 1 | 4 | 3 | 1 | 3 | 3 | 1 | 1 |
| 98 | 8.0 | (8.96) | | | | | | | | | 5 | 5 | | 5 | 5 | 5 | 5 | 4 | 5 | | | 5 | 5 |
| | 4.0 | (4.48) | 1 | 1 | 1 | 1 | 5 | 5 | 2 | 4 | 2 | 1 | 5 | 5 | 2 | 5 | 3 | 1 | 5 | 2 | 2 | 2 |
| | 2.0 | (2.24) | 1 | 1 | 1 | 1 | 5 | 5 | 1 | 3 | 2 | 1 | 5 | 4 | 1 | 5 | 1 | 1 | 4 | 2 | 1 | 1 |
| | 1.0 | (1.12) | 1 | 1 | 1 | 1 | 4 | 4 | 1 | 2 | 1 | 1 | 5 | 3 | 1 | 4 | 1 | 1 | 2 | 1 | 1 | 1 |
| 99 | 8.0 | (8.96) | | | | | | | | | 4 | 4 | | 5 | 5 | 4 | 4 | 2 | 5 | | | 4 | 4 |
| | 4.0 | (4.48) | 1 | 1 | 2 | 1 | 5 | 5 | 1 | 3 | 2 | 1 | 5 | 4 | 3 | 5 | 3 | 1 | 2 | 2 | 2 | 1 |
| | 2.0 | (2.24) | 1 | 1 | 1 | 1 | 5 | 4 | 1 | 3 | 2 | 1 | 5 | 3 | 3 | 4 | 2 | 1 | 1 | 2 | 1 | 1 |
| | 1.0 | (1.12) | 1 | 1 | 1 | 1 | 4 | 5 | 1 | 2 | 1 | 1 | 5 | 3 | 1 | 3 | 1 | 1 | 2 | 1 | 1 | 1 |
| 100 | 8.0 | (8.96) | | | | | | | | | 5 | 2 | | 5 | 5 | 5 | 4 | 3 | 5 | | | 4 | 4 |
| | 4.0 | (4.48) | 1 | 3 | 2 | 2 | 5 | 5 | 2 | 4 | 5 | 2 | 5 | 4 | 5 | 5 | 4 | 2 | 5 | 4 | 4 | 3 |
| | 2.0 | (2.24) | 1 | 3 | 2 | 2 | 5 | 5 | 2 | 4 | 4 | 1 | 5 | 1 | 3 | 5 | 3 | 2 | 4 | 3 | 3 | 3 |
| | 1.0 | (1.12) | 1 | 2 | 1 | 2 | 5 | 5 | 1 | 3 | 3 | 1 | 5 | 1 | 2 | 4 | 2 | 1 | 3 | 2 | 2 | 2 |
| 101 | 1.0 | (1.12) | 1 | 1 | 1 | 1 | 5 | 4 | 1 | 4 | 2 | 2 | 5 | 5 | 5 | 5 | 2 | 2 | 5 | 3 | 3 | 4 |
| | 0.5 | (0.56) | 1 | 1 | 1 | 1 | 4 | 4 | 1 | 4 | 3 | 2 | 5 | 5 | 4 | 5 | 1 | 1 | 5 | 3 | 2 | 3 |
| | 0.25 | (0.28) | 1 | 1 | 1 | 1 | 4 | 3 | 1 | 3 | 2 | 1 | 4 | 3 | 3 | 1 | 1 | 1 | 1 | 1 | 1 | 1 |
| 102 | 8.0 | (8.96) | | | | | | | | | 5 | 4 | | 5 | 5 | 5 | 5 | 5 | 5 | | | 5 | 5 |
| | 4.0 | (4.48) | 2 | 5 | 5 | 4 | 5 | 4 | 3 | 5 | 5 | 4 | 4 | 5 | 5 | 5 | 5 | 5 | 5 | 5 | 5 | 5 |
| | 2.0 | (2.24) | 1 | 4 | 2 | 2 | 5 | 5 | 3 | 5 | 5 | 4 | 5 | 5 | 5 | 5 | 5 | 4 | 5 | 4 | 5 | 5 |
| | 1.0 | (1.12) | 1 | 2 | 2 | 2 | 4 | 3 | 2 | 5 | 4 | 2 | 4 | 4 | 2 | 4 | 3 | 4 | 5 | 4 | 3 | 5 |
| | 1.0 | (1.12) | 1 | 2 | 1 | 1 | 5 | 5 | 2 | 4 | 4 | 3 | 5 | 5 | 5 | 5 | 3 | 2 | 4 | 5 | 3 | 4 |
| | 0.5 | (0.56) | 1 | 2 | 1 | 1 | 5 | 5 | 2 | 4 | 2 | 3 | 5 | 5 | 5 | 5 | 3 | 3 | 5 | 5 | 3 | 2 |
| | 0.25 | (0.28) | 1 | 2 | 1 | 1 | 5 | 4 | 1 | 2 | 1 | 1 | 5 | 4 | 2 | 4 | 2 | 1 | 2 | 4 | 1 | 1 |
| | 0.25 | (0.28) | 1 | 1 | 1 | 1 | 1 | 1 | 1 | 1 | 1 | 1 | 2 | 3 | 2 | 1 | 1 | 1 | 1 | 1 | 1 | 1 |
| | 0.125 | (0.14) | 1 | 1 | 1 | 1 | 1 | 1 | 1 | 1 | 1 | | 1 | 1 | 1 | 1 | 1 | 1 | 1 | 1 | 1 | 1 |
| | 0.0625 | (0.07) | 1 | 1 | 1 | 1 | 1 | 1 | 1 | 1 | 1 | 1 | 1 | 1 | 1 | 1 | 1 | 1 | 1 | 1 | 1 | 1 |

TABLE II-continued

Preemergence

| Example No. of Compound Tested | Rate of Appln. lbs/acre (kg/ha) | Crops | | | | | | | | | Weeds | | | | | | | | | |
|---|---|---|---|---|---|---|---|---|---|---|---|---|---|---|---|---|---|---|---|---|
| | | A | B | C | D | E | F | G | H | I | J | K | L | M | N | O | P | Q | R | S | T |
| 103 | 8.0 (8.96) | | | | | | | | | 5 | 5 | | 5 | 5 | 5 | 5 | 5 | 2 | 5 | | 5 | 5 |
| | 4.0 (4.48) | 3 | 5 | 3 | 2 | 5 | 5 | 3 | 5 | 5 | 4 | 5 | 5 | 5 | 5 | 5 | 5 | 5 | 5 | 5 | 4 | 5 |
| | 2.0 (2.24) | 3 | 4 | 3 | 3 | 5 | 5 | 3 | 5 | 5 | 4 | 5 | 5 | 5 | 5 | 5 | 5 | 5 | 5 | 4 | 4 | 5 |
| | 1.0 (1.12) | 2 | 4 | 2 | 2 | 4 | 5 | 2 | 5 | 4 | 3 | 5 | 5 | 4 | 5 | 5 | 5 | 5 | 4 | 4 | 4 |
| | 1.0 (1.12) | 3 | 5 | 4 | 4 | 5 | 5 | 4 | 5 | 5 | 4 | 5 | 5 | 5 | 4 | 4 | 5 | 5 | 4 | 5 | 5 |
| | 0.5 (0.56) | 1 | 5 | 4 | 4 | 5 | 5 | 2 | 5 | 5 | 3 | 5 | 5 | 2 | 4 | 3 | 4 | 5 | 4 | 4 | 4 |
| | 0.25 (0.28) | | | | | | | | | | | | | | | | | | | | | |
| | 0.25 (0.28) | 1 | 1 | 1 | 1 | 3 | 3 | 2 | 3 | 2 | 2 | 4 | 4 | 2 | 4 | 3 | 2 | 3 | 3 | 3 | 3 |
| | 0.125 (0.14) | 1 | 1 | 1 | 1 | 2 | 2 | 2 | 2 | 1 | 2 | 4 | 3 | 2 | 4 | 2 | 1 | 2 | 1 | 1 | 2 |
| | 0.0625 (0.07) | 1 | 1 | 1 | 1 | 1 | 1 | 2 | 2 | 1 | 1 | 3 | 2 | 1 | 3 | 2 | 1 | 2 | 1 | 1 | 1 |
| 104 | 8.0 (8.96) | | | | | | | | | 5 | 3 | | 5 | 5 | 5 | 4 | 3 | 5 | | 3 | 5 |
| | 4.0 (4.48) | 2 | 3 | 3 | 2 | 5 | 4 | 2 | 5 | 4 | 2 | 4 | 4 | 4 | 5 | 4 | 2 | 5 | 3 | 5 | 3 |
| | 2.0 (2.24) | 1 | 2 | 2 | 1 | 4 | 4 | 2 | 4 | 3 | 2 | 4 | 4 | 3 | 5 | 4 | 2 | 4 | 2 | 3 | 2 |
| | 1.0 (1.12) | 1 | 2 | 2 | 1 | 3 | 3 | 2 | 3 | 1 | 2 | 4 | 4 | 3 | 5 | 2 | 1 | 4 | 1 | 2 | 2 |
| | 1.0 (1.12) | 1 | 2 | 2 | 1 | 4 | 3 | 1 | 4 | 3 | 1 | 3 | 4 | 3 | 5 | 3 | 1 | 5 | 2 | 3 | 3 |
| | 0.5 (0.56) | 1 | 2 | 1 | 1 | 2 | 2 | 1 | 3 | 2 | 1 | 3 | 4 | 2 | 4 | 2 | 1 | 2 | 2 | 2 | 1 |
| | 0.25 (0.28) | 1 | 1 | 1 | 1 | 1 | 1 | 1 | 2 | 1 | 1 | 2 | 2 | 2 | 4 | 1 | 1 | 3 | 1 | 1 | 1 |
| 105 | 8.0 (8.96) | | | | | | | | | 4 | 5 | | 5 | 5 | 5 | 4 | 5 | | 5 | 5 |
| | 4.0 (4.48) | 2 | 5 | 4 | 2 | 5 | 5 | 2 | 5 | 5 | 4 | 4 | 3 | 5 | 5 | 4 | 2 | 5 | 4 | 4 | 5 |
| | 2.0 (2.24) | 1 | 3 | 2 | 1 | 5 | 4 | 2 | 5 | 4 | 3 | 5 | 3 | 5 | 5 | 3 | 1 | 5 | 2 | 1 | 4 |
| | 1.0 (1.12) | 1 | 1 | 1 | 1 | 4 | 2 | 2 | 5 | 2 | 2 | 4 | 2 | 5 | 5 | 2 | 1 | 4 | 1 | 1 | 3 |
| | 1.0 (1.12) | 1 | 3 | 1 | 1 | 3 | 2 | 1 | 4 | 2 | 2 | 4 | 2 | 4 | 4 | 2 | 1 | 5 | 2 | 1 | 3 |
| | 0.5 (0.56) | 1 | 1 | 1 | 1 | 2 | 2 | 1 | 4 | 1 | 1 | 3 | 1 | 2 | 2 | 1 | 1 | 4 | 1 | 1 | 2 |
| | 0.25 (0.28) | 1 | 2 | 1 | 1 | 2 | 1 | 2 | 2 | 1 | 2 | 2 | 2 | 2 | 2 | 1 | 1 | 4 | 1 | 1 | 2 |
| 106 | 8.0 (8.96) | | | | | | | | | 5 | 4 | | 5 | 5 | 5 | 5 | 4 | 5 | | 4 | 5 |
| | 4.0 (4.48) | 1 | 3 | 2 | 3 | 5 | 5 | 2 | 5 | 4 | 4 | 5 | 5 | 5 | 5 | 4 | 4 | 5 | 5 | 4 | 5 |
| | 2.0 (2.24) | 1 | 2 | 1 | 3 | 5 | 5 | 2 | 4 | 3 | 3 | 5 | 4 | 5 | 5 | 3 | 3 | 5 | 4 | 3 | 5 |
| | 1.0 (1.12) | 1 | 2 | 1 | 1 | 5 | 5 | 1 | 3 | 1 | 1 | 5 | 3 | 2 | 4 | 1 | 1 | 3 | 2 | 2 | 3 |
| 107 | 8.0 (8.96) | | | | | | | | | 5 | 3 | | 5 | 5 | 5 | 5 | 3 | 5 | | 4 | 5 |
| | 4.0 (4.48) | 2 | 3 | 3 | 3 | 5 | 5 | 2 | 5 | 5 | 3 | 5 | 5 | 5 | 5 | 4 | 4 | 5 | 4 | 4 | 5 |
| | 2.0 (2.24) | 1 | 3 | 2 | 2 | 5 | 5 | 2 | 4 | 4 | 2 | 5 | 3 | 5 | 5 | 3 | 3 | 5 | 3 | 3 | 4 |
| | 1.0 (1.12) | 1 | 2 | 1 | 2 | 5 | 5 | 1 | 3 | 3 | 1 | 5 | 1 | 3 | 4 | 2 | 2 | 4 | 2 | 2 | 3 |
| 109 | 8.0 (8.96) | | | | | | | | | 5 | 4 | | 5 | 5 | 5 | 5 | 5 | 5 | | 5 | 5 |
| | 4.0 (4.48) | 1 | 4 | 3 | 2 | 5 | 5 | 3 | 5 | 5 | 4 | 5 | 5 | 5 | 5 | 5 | 2 | 5 | 5 | 5 | 5 |
| | 2.0 (2.24) | 1 | 3 | 2 | 1 | 5 | 5 | 1 | 5 | 5 | 4 | 5 | 5 | 5 | 5 | 5 | 1 | 5 | 5 | 5 | 5 |
| | 1.0 (1.12) | 1 | 1 | 1 | 1 | 5 | 5 | 1 | 4 | 4 | 4 | 5 | 5 | 5 | 5 | 5 | 1 | 5 | 5 | 5 | 5 |
| 110 | 8.0 (8.96) | | | | | | | | | 5 | 5 | | 5 | 5 | 5 | 5 | 5 | 5 | | 5 | 5 |
| | 4.0 (4.48) | 3 | 3 | 3 | 3 | 5 | 5 | 3 | 5 | 5 | 5 | 5 | 5 | 5 | 5 | 5 | 1 | 5 | 5 | 5 | 5 |
| | 2.0 (2.24) | 2 | 2 | 1 | 2 | 5 | 5 | 2 | 4 | 5 | 4 | 5 | 5 | 5 | 5 | 5 | 1 | 5 | 5 | 5 | 5 |
| | 1.0 (1.12) | 1 | 1 | 1 | 1 | 5 | 5 | 2 | 3 | 5 | 3 | 5 | 5 | 5 | 5 | 5 | 1 | 5 | 5 | 5 | 4 |
| | 1.0 (1.12) | 1 | 1 | 1 | 2 | 5 | 5 | 2 | 5 | 5 | 4 | 5 | 5 | 5 | 5 | 5 | 2 | 5 | 5 | 5 | 5 |
| | 0.5 (0.56) | 1 | 1 | 1 | 1 | 4 | 5 | 2 | 5 | 4 | 2 | 5 | 4 | 5 | 5 | 3 | 2 | 4 | 4 | 3 | 5 |
| | 0.25 (0.28) | 1 | 1 | 1 | 1 | 4 | 5 | 1 | 2 | 3 | 1 | 5 | 4 | 5 | 5 | 4 | 1 | 3 | 4 | 2 | 4 |
| 112 | 8.0 (8.96) | | | | | | | | | 5 | 5 | | 5 | 5 | 5 | 5 | 5 | 5 | | 5 | 5 |
| | 4.0 (4.48) | 2 | 3 | 3 | 2 | 5 | 5 | 2 | 5 | 4 | 4 | 5 | 5 | 5 | 5 | 5 | 2 | 5 | 5 | 5 | 5 |
| | 2.0 (2.24) | 2 | 1 | 2 | 2 | 5 | 5 | 2 | 4 | 5 | 4 | 5 | 5 | 5 | 5 | 5 | 2 | 5 | 5 | 5 | 5 |
| | 1.0 (1.12) | 1 | 1 | 2 | 2 | 5 | 5 | 2 | 3 | 2 | 4 | 5 | 5 | 5 | 5 | 5 | 2 | 5 | 5 | 4 | 5 |
| | 1.0 (1.12) | 3 | 3 | 3 | 2 | 5 | 5 | 3 | 4 | 5 | 4 | 5 | 5 | 5 | 5 | 5 | 1 | 5 | 5 | 5 | 5 |
| | 0.5 (0.56) | 1 | 1 | 1 | 1 | 5 | 5 | 2 | 5 | 5 | 3 | 5 | 5 | 5 | 5 | 5 | 1 | 5 | 5 | 3 | 4 |
| | 0.25 (0.28) | 1 | 1 | 1 | 1 | 5 | 5 | 2 | 3 | 4 | 3 | 5 | 5 | 5 | 5 | 5 | 1 | 5 | 5 | 2 | 5 |
| 113 | 8.0 (8.96) | | | | | | | | | 5 | 5 | | 5 | 5 | 5 | 5 | 5 | 5 | | 5 | 5 |
| | 4.0 (4.48) | 3 | 4 | 3 | 4 | 5 | 5 | 3 | 5 | 5 | 5 | 5 | 5 | 5 | 5 | 5 | 3 | 5 | 5 | 5 | 5 |
| | 2.0 (2.24) | 3 | 3 | 3 | 3 | 5 | 5 | 2 | 5 | 5 | 5 | 5 | 5 | 5 | 5 | 5 | 2 | 5 | 5 | 5 | 5 |
| | 1.0 (1.12) | 1 | 1 | 2 | 2 | 5 | 5 | 1 | 4 | 5 | 4 | 5 | 5 | 5 | 5 | 5 | 1 | 5 | 5 | 5 | 5 |
| | 1.0 (1.12) | 1 | 2 | 2 | 1 | 5 | 5 | 2 | 4 | 5 | 4 | 5 | 5 | 5 | 5 | 5 | 1 | 5 | 5 | 5 | 5 |
| | 0.5 (0.56) | 1 | 2 | 2 | 1 | 5 | 5 | 2 | 4 | 4 | 4 | 5 | 5 | 5 | 5 | 5 | 1 | 5 | 5 | 1 | 4 |
| | 0.25 (0.28) | 1 | 1 | 1 | 1 | 4 | 5 | 1 | 3 | 3 | 1 | 5 | 4 | 5 | 5 | 4 | 1 | 5 | 4 | 1 | 4 |
| 114 | 8.0 (8.96) | | | | | | | | | 5 | 4 | | 5 | 5 | 5 | 5 | 2 | 5 | | 5 | 5 |
| | 4.0 (4.48) | 1 | 1 | 3 | 2 | 5 | 5 | 1 | 3 | 4 | 2 | 5 | 4 | 4 | 5 | 2 | 1 | 4 | 3 | 3 | 3 |
| | 2.0 (2.24) | 1 | 1 | 1 | 1 | 5 | 5 | 1 | 2 | 1 | 1 | 5 | 3 | 2 | 5 | 2 | 1 | 3 | 2 | 1 | 3 |
| | 1.0 (1.12) | 1 | 1 | 1 | 1 | 5 | 5 | 1 | 1 | 1 | 1 | 5 | 3 | 3 | 5 | 1 | 1 | 3 | 2 | 1 | 2 |
| 115 | 1.0 (1.12) | 2 | 4 | 3 | 3 | 5 | 5 | 4 | 5 | 5 | 4 | 5 | 5 | 5 | 5 | 5 | | 5 | 5 | 3 | 5 |
| | 0.5 (0.56) | 1 | 3 | 3 | 1 | 5 | 5 | 3 | 5 | 3 | 4 | 5 | 5 | 5 | 5 | 5 | 1 | 5 | 5 | 3 | 5 |
| | 0.25 (0.28) | 1 | 1 | 1 | 1 | 5 | 5 | 2 | 4 | 2 | 3 | 5 | 5 | 5 | 5 | 2 | 1 | 5 | 2 | 1 | 5 |
| 116 | 1.0 (1.12) | 1 | 1 | 1 | 2 | 5 | 5 | 1 | 4 | 5 | 4 | 5 | 5 | 5 | 5 | 5 | 4 | 5 | 5 | 4 | 4 |
| | 0.5 (0.56) | 1 | 1 | 1 | 1 | 5 | 5 | 1 | 2 | 4 | 1 | 5 | 5 | 5 | 5 | 4 | 3 | 5 | 5 | 4 | 3 |
| | 0.25 (0.28) | 1 | 1 | 1 | 1 | 5 | 5 | 1 | 1 | 2 | 1 | 5 | 1 | 4 | 4 | 1 | 1 | 2 | 2 | 1 | 1 |
| 117 | 1.0 (1.12) | 1 | 1 | 2 | 1 | 5 | 5 | 2 | 4 | 5 | 3 | 5 | 5 | 5 | 5 | 5 | 2 | 5 | 5 | 2 | 5 |
| | 0.5 (0.56) | 1 | 1 | 1 | 1 | 5 | 5 | 3 | 3 | 4 | 2 | 5 | 5 | 5 | 5 | 5 | 2 | 5 | 5 | 2 | 5 |
| | 0.25 (0.28) | 1 | 1 | 1 | 1 | 5 | 5 | 2 | 2 | 1 | 2 | 5 | 4 | 4 | 3 | 2 | 1 | 4 | 4 | 1 | 3 |
| 118 | 8.0 (8.96) | | | | | | | | | 5 | 5 | | 5 | 5 | 5 | 5 | 4 | 5 | | 5 | 5 |
| | 4.0 (4.48) | 3 | 3 | 3 | 3 | 5 | 5 | 3 | 5 | 5 | 4 | 5 | 5 | 5 | 5 | 4 | 5 | 4 | 4 | 4 | 5 |
| | 2.0 (2.24) | 2 | 3 | 2 | 2 | 5 | 5 | 2 | 5 | 4 | 4 | 5 | 4 | 5 | 5 | 4 | 2 | 5 | 4 | 4 | 5 |
| | 1.0 (1.12) | 1 | 1 | 1 | 1 | 4 | 4 | 1 | 4 | 2 | 2 | 4 | 3 | 4 | 4 | 4 | 2 | 4 | 2 | 3 | 4 |
| | 1.0 (1.12) | 1 | 3 | 3 | 2 | 5 | 5 | 2 | 4 | 2 | 3 | 5 | 5 | 5 | 5 | 4 | 2 | 5 | 5 | 4 | 5 |
| | 0.5 (0.56) | 1 | 1 | 1 | 1 | 5 | 5 | 2 | 3 | 1 | 1 | 4 | 3 | 4 | 4 | 2 | 1 | 3 | 1 | 2 | 2 |

TABLE II-continued

Preemergence

| Example No. of Compound Tested | Rate of Appln. lbs/acre (kg/ha) | Crops | | | | | | | | | Weeds | | | | | | | | | |
|---|---|---|---|---|---|---|---|---|---|---|---|---|---|---|---|---|---|---|---|---|
| | | A | B | C | D | E | F | G | H | I | J | K | L | M | N | O | P | Q | R | S | T |
| | 0.25 (0.28) | 1 | 2 | 1 | 2 | 5 | 5 | 2 | 4 | 1 | 1 | 5 | 5 | 5 | 5 | 4 | 2 | 5 | 5 | 4 | 4 |
| | 0.25 (0.28) | 1 | 1 | 1 | 1 | 5 | 5 | 2 | 4 | 1 | 2 | 5 | 1 | 4 | 4 | 3 | 1 | 3 | 2 | 2 | 2 |
| | 0.125 (0.14) | 1 | 1 | 1 | 1 | 4 | 4 | 2 | 2 | 1 | 1 | 5 | 1 | 2 | 4 | 1 | 1 | 3 | 1 | 1 | 1 |
| | 0.0625 (0.07) | 1 | 1 | 1 | 1 | 2 | 3 | 1 | 1 | 1 | 1 | 4 | 2 | 1 | 3 | 1 | 1 | 2 | 1 | 1 | 1 |
| 119 | 8.0 (8.96) | | | | | | | | | 5 | 4 | | 5 | 5 | 5 | 5 | 4 | 5 | | | 5 | 5 |
| | 4.0 (4.48) | 5 | 5 | 5 | 5 | 5 | 5 | 5 | 5 | 5 | 5 | 5 | 5 | 5 | 5 | 5 | 5 | 5 | 5 | 5 | 5 |
| | 2.0 (2.24) | 5 | 5 | 5 | 5 | 5 | 5 | 5 | 5 | 5 | 5 | 5 | 5 | 5 | 5 | 5 | 5 | 5 | 5 | 5 | 5 |
| | 1.0 (1.12) | 4 | 5 | 5 | 4 | 5 | 5 | 4 | 5 | 5 | 5 | 5 | 5 | 5 | 5 | 5 | 4 | 5 | 5 | 5 | 5 |
| | 1.0 (1.12) | 3 | 5 | 5 | 4 | 5 | 5 | 4 | 5 | 5 | 5 | 5 | 5 | 5 | 5 | 5 | 4 | 5 | 5 | 5 | 5 |
| | 0.5 (0.56) | 2 | 4 | 4 | 3 | 5 | 5 | 4 | 5 | 5 | 5 | 5 | 5 | 5 | 5 | 5 | 1 | 5 | 5 | 5 | 5 |
| | 0.25 (0.28) | 1 | 3 | 1 | 2 | 5 | 5 | 2 | 4 | 5 | 4 | 5 | 5 | 5 | 5 | 4 | 1 | 5 | 5 | 4 | 4 |
| | 0.25 (0.28) | 1 | 2 | 1 | 2 | 5 | 5 | 1 | 3 | 5 | 2 | 5 | 5 | 5 | 5 | 4 | 1 | 5 | 4 | 4 | 5 |
| | 0.125 (0.14) | 1 | 1 | 1 | 1 | 5 | 4 | 1 | 1 | 3 | 1 | 5 | 4 | 5 | 5 | 3 | 1 | 5 | 3 | 3 | 3 |
| | 0.0625 (0.07) | 1 | 1 | 1 | 1 | 3 | 3 | 1 | 1 | 1 | 1 | 5 | 3 | 1 | 1 | 1 | 1 | 1 | 1 | 2 | 1 |
| 120 | 8.0 (8.96) | | | | | | | | | 4 | 1 | | 4 | 4 | 5 | 2 | 2 | 5 | | 4 | 4 |
| | 4.0 (4.48) | 1 | 2 | 2 | 2 | 5 | 5 | 1 | 4 | 3 | 1 | 5 | 3 | 3 | 4 | 3 | 1 | 4 | 3 | 3 | 3 |
| | 2.0 (2.24) | 1 | 1 | 1 | 2 | 5 | 5 | 1 | 3 | 4 | 1 | 5 | 2 | 4 | 3 | 1 | 1 | 3 | 3 | 2 | 2 |
| | 1.0 (1.12) | 1 | 1 | 1 | 2 | 5 | 5 | 2 | 4 | 4 | 1 | 5 | 2 | 4 | 3 | 1 | 1 | 3 | 3 | 2 | 3 |
| | 1.0 (1.12) | 1 | 1 | 1 | 1 | 2 | 3 | 1 | 2 | 1 | 1 | 4 | 2 | 2 | 4 | 1 | 1 | 2 | 2 | 1 | 1 |
| | 0.5 (0.56) | 1 | 1 | 1 | 1 | 1 | 2 | 1 | 2 | 1 | 1 | 4 | 1 | 1 | 4 | 1 | 1 | 2 | 1 | 1 | 1 |
| | 0.25 (0.28) | 1 | 1 | 1 | 1 | 1 | 1 | 1 | 1 | 1 | 1 | 4 | 1 | 1 | 3 | 1 | 1 | 1 | 1 | 1 | 1 |
| 121 | 8.0 (8.96) | | | | | | | | | 5 | 4 | | 5 | 5 | 5 | 5 | 4 | 5 | | | 5 | 5 |
| | 4.0 (4.48) | 1 | 4 | 2 | 2 | 5 | 5 | 2 | 3 | 4 | 1 | 5 | 5 | 4 | 5 | 3 | 2 | 4 | 3 | 4 | 3 |
| | 2.0 (2.24) | 1 | 1 | 2 | 1 | 5 | 5 | 2 | 3 | 2 | 1 | 5 | 4 | 4 | 5 | 2 | 2 | 4 | 3 | 3 | 3 |
| | 1.0 (1.12) | 1 | 1 | 1 | 1 | 5 | 4 | 1 | 2 | 1 | 1 | 4 | 2 | 3 | 5 | 1 | 1 | 3 | 1 | 1 | 1 |
| | 1.0 (1.12) | 1 | 1 | 1 | 1 | 5 | 4 | 1 | 3 | 1 | 1 | 5 | 1 | 3 | 5 | 2 | 1 | 3 | 2 | 3 | 2 |
| | 0.5 (0.56) | 1 | 1 | 1 | 1 | 5 | 4 | 1 | 2 | 1 | 1 | 5 | 1 | 3 | 5 | 1 | 1 | 3 | 2 | 2 | 1 |
| | 0.25 (0.28) | 1 | 1 | 1 | 1 | 5 | 4 | 1 | 1 | 1 | 1 | 4 | 1 | 2 | 4 | 1 | 1 | 1 | 1 | 1 | 1 |
| 122 | 8.0 (8.96) | | | | | | | | | 4 | 3 | | 5 | 5 | 5 | 4 | 3 | 4 | | 4 | 5 |
| | 4.0 (4.48) | 1 | 1 | 2 | 2 | 5 | 5 | 1 | 3 | 2 | 1 | 4 | 4 | 3 | 5 | 2 | 1 | 3 | 3 | 2 | 3 |
| | 2.0 (2.24) | 1 | 1 | 1 | 2 | 5 | 4 | 1 | 2 | 2 | 1 | 4 | 2 | 3 | 4 | 1 | 1 | 2 | 2 | 1 | 2 |
| | 1.0 (1.12) | 1 | 1 | 1 | 1 | 4 | 3 | 1 | 2 | 2 | 1 | 4 | 2 | 2 | 3 | 1 | 1 | 2 | 1 | 1 | 2 |
| 123 | 8.0 (8.96) | | | | | | | | | 5 | 3 | | 5 | 5 | 5 | 5 | 4 | 5 | | 5 | 5 |
| | 4.0 (4.48) | 3 | 2 | 3 | 4 | 5 | 5 | 3 | 5 | 5 | 4 | 5 | 4 | 5 | 5 | 5 | 3 | 5 | 5 | 5 | 5 |
| | 2.0 (2.24) | 2 | 2 | 3 | 3 | 5 | 5 | 3 | 5 | 5 | 3 | 5 | 4 | 5 | 5 | 5 | 2 | 5 | 4 | 4 | 5 |
| | 1.0 (1.12) | 1 | 2 | 2 | 2 | 5 | 5 | 2 | 4 | 3 | 2 | 5 | 4 | 4 | 5 | 4 | 1 | 5 | 4 | 2 | 5 |
| | 1.0 (1.12) | 1 | 1 | 1 | 1 | 5 | 5 | 1 | 2 | 1 | 1 | 5 | 4 | 4 | 5 | 2 | 1 | 4 | 2 | 1 | 3 |
| | 0.5 (0.56) | 1 | 1 | 1 | 1 | 5 | 5 | 1 | 2 | 1 | 1 | 5 | 3 | 3 | 5 | 1 | 1 | 3 | 1 | 1 | 1 |
| | 0.25 (0.28) | 1 | 1 | 1 | 1 | 3 | 3 | 1 | 2 | 1 | 1 | 5 | 1 | 1 | 4 | 1 | 1 | 2 | 1 | 1 | 1 |
| 124 | 8.0 (8.96) | | | | | | | | | 5 | 3 | | 5 | 5 | 5 | 5 | 4 | 5 | | 5 | 5 |
| | 4.0 (4.48) | 1 | 2 | 1 | 2 | 5 | 5 | 2 | 4 | 4 | 3 | 5 | 4 | 5 | 5 | 4 | 1 | 5 | 4 | 3 | 4 |
| | 2.0 (2.24) | 1 | 2 | 1 | 2 | 5 | 5 | 2 | 3 | 3 | 2 | 5 | 5 | 4 | 5 | 3 | 1 | 5 | 3 | 1 | 1 |
| | 1.0 (1.12) | 1 | 1 | 1 | 1 | 5 | 5 | 1 | 3 | 2 | 1 | 5 | 3 | 3 | 5 | 1 | 1 | 4 | 1 | 1 | 3 |
| | 1.0 (1.12) | 1 | 1 | 1 | 1 | 4 | 4 | 2 | 2 | 2 | 1 | 5 | 3 | 3 | 5 | 1 | 1 | 2 | 2 | 1 | 1 |
| | 0.5 (0.56) | 1 | 1 | 1 | 1 | 2 | 3 | 1 | 2 | 1 | 1 | 5 | 3 | 2 | 5 | 1 | 1 | 1 | 1 | 1 | 1 |
| | 0.25 (0.28) | 1 | 1 | 1 | 1 | 1 | 1 | 1 | 1 | 1 | 1 | 4 | 1 | 1 | 4 | 1 | 1 | 1 | 1 | 1 | 1 |
| 125 | 8.0 (8.96) | | | | | | | | | 5 | 4 | | 5 | 5 | 5 | 5 | 3 | 5 | | 5 | 5 |
| | 4.0 (4.48) | 1 | 2 | 1 | 3 | 5 | 5 | 2 | 5 | 5 | 3 | 5 | 4 | 5 | 5 | 4 | 1 | 5 | 5 | 3 | 5 |
| | 2.0 (2.24) | 1 | 1 | 1 | 1 | 5 | 5 | 2 | 5 | 5 | 1 | 5 | 2 | 5 | 5 | 2 | 1 | 5 | 3 | 3 | 4 |
| | 1.0 (1.12) | 1 | 1 | 1 | 1 | 5 | 4 | 1 | 2 | 3 | 1 | 5 | 3 | 3 | 5 | 1 | 1 | 3 | 1 | 1 | 2 |
| | 1.0 (1.12) | 1 | 1 | 1 | 1 | 3 | 4 | 1 | 3 | 3 | 1 | 5 | 3 | 4 | 5 | 1 | 1 | 5 | 1 | 1 | 2 |
| | 0.5 (0.56) | 1 | 1 | 1 | 1 | 1 | 3 | 1 | 1 | 1 | 1 | 4 | 1 | 2 | 3 | 1 | 1 | 3 | 1 | 1 | 1 |
| | 0.25 (0.28) | 1 | 1 | 1 | 1 | 3 | 3 | 1 | 1 | 1 | 1 | 1 | 1 | 1 | 1 | 1 | 1 | 1 | 1 | 1 | 1 |
| 126 | 8.0 (8.96) | | | | | | | | | 5 | 4 | | 5 | 5 | 5 | 5 | 5 | 5 | | 5 | 5 |
| | 4.0 (4.48) | 2 | 3 | 3 | 3 | 5 | 5 | 2 | 4 | 4 | 3 | 5 | 5 | 5 | 5 | 5 | 2 | 5 | 5 | 3 | 5 |
| | 2.0 (2.24) | 1 | 2 | 3 | 2 | 5 | 5 | 2 | 3 | 3 | 2 | 5 | 5 | 5 | 5 | 4 | 2 | 5 | 4 | 2 | 5 |
| | 1.0 (1.12) | 1 | 1 | 1 | 2 | 5 | 5 | 1 | 2 | 1 | 1 | 5 | 4 | 4 | 5 | 3 | 1 | 4 | 3 | 2 | 4 |
| | 1.0 (1.12) | 1 | 1 | 1 | 1 | 5 | 5 | 1 | 3 | 1 | 1 | 5 | 5 | 5 | 5 | 3 | 1 | 5 | 4 | 3 | 4 |
| | 0.5 (0.56) | 1 | 1 | 1 | 1 | 5 | 4 | 1 | 2 | 1 | 1 | 5 | 3 | 3 | 4 | 1 | 1 | 2 | 2 | 1 | 3 |
| | 0.25 (0.28) | 1 | 1 | 1 | 1 | 5 | 1 | 1 | 3 | 1 | 1 | 5 | 5 | 5 | 5 | 3 | 1 | 5 | 4 | 3 | 4 |
| 128 | 8.0 (8.96) | | | | | | | | | 4 | 4 | | 5 | 5 | 5 | 5 | 3 | 5 | | 4 | 5 |
| | 4.0 (4.48) | 1 | 2 | 2 | 2 | 5 | 5 | 2 | 4 | 4 | 3 | 5 | 5 | 5 | 5 | 4 | 2 | 5 | 5 | 4 | 4 |
| | 2.0 (2.24) | 1 | 1 | 2 | 2 | 5 | 5 | 1 | 4 | 4 | 3 | 5 | 4 | 4 | 5 | 3 | 2 | 5 | 4 | 3 | 3 |
| | 1.0 (1.12) | 1 | 1 | 1 | 1 | 5 | 5 | 1 | 3 | 3 | 1 | 5 | 4 | 3 | 5 | 3 | 2 | 4 | 3 | 3 | 2 |
| | 1.0 (1.12) | 1 | 1 | 1 | 2 | 4 | 5 | 1 | 4 | 2 | 2 | 5 | 4 | 4 | 3 | 1 | 4 | 2 | 2 | 2 |
| | 0.5 (0.56) | 1 | 1 | 1 | 1 | 3 | 4 | 1 | 3 | 2 | 1 | 5 | 2 | 3 | 3 | 2 | 1 | 3 | 2 | 2 | 2 |
| | 0.25 (0.28) | 1 | 1 | 1 | 1 | 4 | 4 | 1 | 2 | 1 | 1 | 4 | 2 | 2 | 3 | 1 | 1 | 2 | 2 | 2 | 2 |
| 129 | 8.0 (8.96) | | | | | | | | | 1 | 1 | | 3 | 3 | 5 | 1 | 1 | 3 | | 2 | 1 |
| | 4.0 (4.48) | 1 | 1 | 1 | 1 | 3 | 4 | 1 | 2 | 2 | 1 | 4 | 1 | 3 | 3 | 1 | 1 | 3 | 1 | 1 | 1 |
| | 2.0 (2.24) | 1 | 1 | 1 | 1 | 2 | 3 | 1 | 2 | 1 | 1 | 4 | 1 | 2 | 2 | 1 | 1 | 2 | 1 | 1 | 1 |
| | 1.0 (1.12) | 1 | 1 | 1 | 1 | 1 | 2 | 1 | 2 | 1 | 1 | 3 | 1 | 1 | 3 | 1 | 1 | 1 | 1 | 1 | 1 |
| 135 | 1.0 (1.12) | 1 | 2 | 2 | 1 | 5 | 5 | 2 | 3 | 1 | 3 | 5 | 4 | 3 | 4 | 2 | 1 | 3 | 1 | 1 | 4 |
| | 0.5 (0.56) | 1 | 1 | 1 | 1 | 5 | 5 | 2 | 2 | 1 | 1 | 4 | 2 | 3 | 3 | 1 | 1 | 1 | 1 | 1 | 1 |
| | 0.25 (0.28) | 1 | 1 | 1 | 1 | 3 | 2 | 1 | 1 | 1 | 1 | 3 | 2 | 2 | 2 | 1 | 1 | 1 | 1 | 1 | 1 |
| 136 | 1.0 (1.12) | 1 | 1 | 2 | 1 | 5 | 5 | 3 | 5 | 5 | 5 | 5 | 5 | 5 | 5 | 5 | 2 | 5 | 5 | 4 | 5 |
| | 0.5 (0.56) | 1 | 1 | 1 | 1 | 5 | 5 | 2 | 4 | 1 | 3 | 5 | 4 | 5 | 5 | 2 | 3 | 5 | 2 | 3 | 4 |

TABLE II-continued

Preemergence

| Example No. of Compound Tested | Rate of Appln. lbs/acre | (kg/ha) | Crops | | | | | | | | | Weeds | | | | | | | | | |
|---|---|---|---|---|---|---|---|---|---|---|---|---|---|---|---|---|---|---|---|---|---|
| | | | A | B | C | D | E | F | G | H | I | J | K | L | M | N | O | P | Q | R | S | T |
| | 0.25 | (0.28) | 1 | 1 | 1 | 1 | 3 | 4 | 1 | 2 | 1 | 1 | 5 | 4 | 5 | 4 | 2 | 1 | 3 | 1 | 2 | 4 |
| 140 | 8.0 | (8.96) | | | | | | | | | 3 | 5 | | 5 | 5 | 5 | 5 | 2 | 5 | | | 5 | 5 |
| | 4.0 | (4.48) | 1 | 3 | 1 | 2 | 5 | 5 | 3 | 5 | 1 | 4 | 5 | 5 | 5 | 5 | 5 | 1 | 5 | 2 | 3 | 5 |
| | 2.0 | (2.24) | 1 | 1 | 1 | 1 | 5 | 5 | 2 | 5 | 1 | 4 | 5 | 5 | 5 | 5 | 5 | 1 | 5 | 1 | 3 | 5 |
| | 1.0 | (1.12) | 1 | 1 | 1 | 1 | 3 | 4 | 1 | 3 | 1 | 1 | 5 | 3 | 2 | 5 | 1 | 1 | 5 | 1 | 1 | 4 |
| 141 | 8.0 | (8.96) | | | | | | | | | 5 | 5 | | 5 | 5 | 5 | 5 | 1 | 5 | | | 5 | 5 |
| | 4.0 | (4.48) | 1 | 4 | 2 | 1 | 5 | 5 | 2 | 3 | 2 | 3 | 5 | 5 | 5 | 5 | 5 | 1 | 5 | 5 | 5 | 5 |
| | 2.0 | (2.24) | 1 | 1 | 1 | 1 | 5 | 5 | 1 | 2 | 2 | 4 | 5 | 5 | 5 | 5 | 5 | 1 | 5 | 4 | 4 | 5 |
| | 1.0 | (1.12) | 1 | 1 | 1 | 1 | 5 | 4 | 1 | 2 | 2 | 3 | 5 | 5 | 5 | 5 | 5 | 1 | 5 | 1 | 4 | 4 |
| 142 | 8.0 | (8.96) | | | | | | | | | 5 | 4 | | 5 | 5 | 5 | 5 | 2 | 5 | | | 5 | 5 |
| | 4.0 | (4.48) | 1 | 3 | 1 | 1 | 5 | 5 | 3 | 5 | 2 | 3 | 5 | 5 | 5 | 5 | 5 | 2 | 5 | 4 | 5 | 4 |
| | 2.0 | (2.24) | 1 | 1 | 1 | 1 | 5 | 5 | 1 | 4 | 1 | 2 | 5 | 4 | 5 | 5 | 2 | 1 | 5 | 2 | 3 | 4 |
| | 1.0 | (1.12) | 1 | 1 | 1 | 1 | 5 | 5 | 1 | 3 | 1 | 1 | 5 | 5 | 4 | 4 | 2 | 1 | 1 | 1 | 3 | 3 |
| 143 | 8.0 | (8.96) | | | | | | | | | 3 | 4 | | 5 | 5 | 5 | 5 | 2 | 5 | | | 4 | 4 |
| | 4.0 | (4.48) | 1 | 1 | 1 | 1 | 2 | 5 | 1 | 1 | 1 | 1 | 5 | 5 | 5 | 5 | 3 | 1 | 5 | 2 | 1 | 1 |
| | 2.0 | (2.24) | 1 | 1 | 1 | 1 | 2 | 5 | 1 | 1 | 1 | 1 | 5 | 3 | 4 | 5 | 2 | 1 | 4 | 3 | 1 | 1 |
| | 1.0 | (1.12) | 1 | 1 | 1 | 1 | 1 | 4 | 1 | 1 | 1 | 1 | 5 | 2 | 5 | 4 | 1 | 1 | 2 | 2 | 1 | 1 |
| 144 | 8.0 | (8.96) | | | | | | | | | 2 | 4 | | 5 | 5 | 5 | 5 | 1 | 5 | | | 4 | 5 |
| | 4.0 | (4.48) | 1 | 1 | 1 | 1 | 2 | 5 | 2 | 2 | 1 | 3 | 5 | 5 | 5 | 5 | 3 | 1 | 5 | 5 | 2 | 5 |
| | 2.0 | (2.24) | 1 | 1 | 1 | 1 | 1 | 5 | 2 | 1 | 1 | 1 | 5 | 4 | 3 | 5 | 1 | 1 | 4 | 2 | 1 | 3 |
| | 1.0 | (1.12) | 1 | 1 | 1 | 1 | 1 | 5 | 1 | 2 | 1 | 1 | 5 | 2 | 2 | 5 | 1 | 1 | 4 | 1 | 1 | 1 |
| 145 | 8.0 | (8.96) | | | | | | | | | 4 | 4 | | 5 | 5 | 5 | 5 | 3 | 5 | | | 5 | 5 |
| | 4.0 | (4.48) | 2 | 3 | 3 | 4 | 5 | 5 | 2 | 5 | 4 | 1 | 5 | 4 | 5 | 5 | 3 | 2 | 5 | 3 | 3 | 5 |
| | 2.0 | (2.24) | 1 | 1 | 2 | 2 | 5 | 5 | 2 | 3 | 1 | 1 | 5 | 4 | 5 | 4 | 2 | 5 | 4 | 3 | 3 |
| | 1.0 | (1.12) | 1 | 1 | 1 | 2 | 3 | 5 | 1 | 2 | 2 | 1 | 5 | 4 | 3 | 5 | 2 | 1 | 5 | 4 | 2 | 2 |
| 146 | 8.0 | (8.96) | | | | | | | | | 5 | 5 | | 5 | 5 | 5 | 5 | 4 | 5 | | | 5 | 5 |
| | 4.0 | (4.48) | 3 | 2 | 2 | 3 | 5 | 5 | 3 | 5 | 5 | 4 | 5 | 5 | 5 | 5 | 5 | 4 | 5 | 5 | 5 | 5 |
| | 2.0 | (2.24) | 2 | 1 | 2 | 3 | 5 | 5 | 3 | 4 | 5 | 4 | 5 | 5 | 5 | 5 | 5 | 2 | 5 | 5 | 3 | 5 |
| | 1.0 | (1.12) | 1 | 1 | 1 | 2 | 4 | 5 | 3 | 4 | 3 | 3 | 5 | 5 | 4 | 5 | 5 | 2 | 5 | 4 | 3 | 3 |
| | 1.0 | (1.12) | 2 | 1 | 2 | 4 | 5 | 5 | 3 | 5 | 5 | 4 | 5 | 5 | 5 | 5 | 4 | 2 | 5 | 5 | 2 | 5 |
| | 0.5 | (0.56) | 1 | 1 | 1 | 2 | 4 | 5 | 2 | 3 | 2 | 3 | 5 | 4 | 4 | 5 | 2 | 1 | 5 | 4 | 2 | 3 |
| | 0.25 | (0.28) | 1 | 1 | 1 | 2 | 3 | 5 | 1 | 2 | 2 | 1 | 5 | 1 | 2 | 3 | 1 | 1 | 2 | 2 | 1 | 1 |
| 147 | 8.0 | (8.96) | | | | | | | | | 4 | 3 | | 5 | 4 | 4 | 3 | 2 | 4 | | | 3 | 3 |
| | 4.0 | (4.48) | 1 | 1 | 2 | 2 | 4 | 5 | 2 | 4 | 2 | 1 | 5 | 5 | 4 | 5 | 1 | 2 | 2 | 2 | 1 | 1 |
| | 2.0 | (2.24) | 1 | 1 | 1 | 1 | 2 | 1 | 1 | 2 | 1 | 1 | 4 | 4 | 3 | 5 | 1 | 1 | 2 | 2 | 1 | 1 |
| | 1.0 | (1.12) | 1 | 1 | 1 | 1 | 2 | 1 | 1 | 2 | 1 | 1 | 4 | 1 | 2 | 2 | 1 | 1 | 1 | 1 | 1 | 1 |
| 148 | 8.0 | (8.96) | | | | | | | | | 3 | 1 | | 5 | 4 | 5 | 3 | 2 | 3 | | | 3 | 3 |
| | 4.0 | (4.48) | 1 | 1 | 1 | 1 | 5 | 5 | 1 | 3 | 3 | 1 | 5 | 4 | 4 | 4 | 3 | 3 | 3 | 4 | 2 | 3 |
| | 2.0 | (2.24) | 1 | 1 | 1 | 1 | 3 | 5 | 1 | 2 | 1 | 1 | 5 | 1 | 3 | 1 | 1 | 1 | 1 | 1 | 1 | 1 |
| | 1.0 | (1.12) | 1 | 1 | 1 | 1 | 1 | 3 | 1 | 2 | 1 | 1 | 4 | 1 | 2 | 1 | 1 | 1 | 1 | 1 | 1 | 1 |
| 149 | 8.0 | (8.96) | | | | | | | | | 5 | 4 | | 5 | 5 | 5 | 5 | 5 | 5 | | | 5 | 5 |
| | 4.0 | (4.48) | 2 | 5 | 4 | 3 | 5 | 5 | 3 | 5 | 5 | 4 | 5 | 5 | 5 | 5 | 4 | 4 | 5 | 4 | 4 | 5 |
| | 2.0 | (2.24) | 1 | 4 | 3 | 3 | 5 | 5 | 3 | 5 | 4 | 3 | 5 | 5 | 5 | 5 | 4 | 3 | 5 | 4 | 4 | 5 |
| | 1.0 | (1.12) | 1 | 4 | 3 | 2 | 5 | 5 | 3 | 4 | 3 | 3 | 5 | 4 | 4 | 5 | 4 | 2 | 5 | 3 | 3 | 4 |
| 150 | 8.0 | (8.96) | | | | | | | | | 5 | 5 | | 5 | 5 | 5 | 5 | 5 | 5 | | | 5 | 5 |
| | 4.0 | (4.48) | 3 | 5 | 5 | 4 | 5 | 5 | 4 | 5 | 5 | 4 | 5 | 5 | 5 | 5 | 5 | 4 | 5 | 5 | 5 | 5 |
| | 2.0 | (2.24) | 3 | 5 | 5 | 4 | 5 | 5 | 4 | 5 | 5 | 4 | 4 | 5 | 5 | 5 | 5 | 4 | 5 | 5 | 5 | 5 |
| | 1.0 | (1.12) | 2 | 5 | 4 | 4 | 5 | 5 | 4 | 5 | 5 | 4 | 5 | 5 | 5 | 5 | 3 | 5 | 4 | 5 | 5 |
| 151 | 8.0 | (8.96) | | | | | | | | | 3 | 4 | | 5 | 3 | 5 | 3 | 2 | 4 | | | 4 | 4 |
| | 4.0 | (4.48) | 1 | 2 | 3 | 2 | 5 | 5 | 2 | 3 | 4 | 2 | 5 | 2 | 4 | 5 | 2 | 3 | 5 | 5 | 4 | 4 |
| | 2.0 | (2.24) | 1 | 2 | 3 | 1 | 5 | 4 | 2 | 3 | 4 | 1 | 5 | 1 | 3 | 5 | 3 | 1 | 4 | 2 | 3 | 3 |
| | 1.0 | (1.12) | 1 | 1 | 2 | 1 | 5 | 3 | 1 | 3 | 3 | 1 | 5 | 1 | 2 | 5 | 1 | 1 | 4 | 2 | 3 | 3 |
| 154 | 8.0 | (8.96) | | | | | | | | | 3 | 1 | | 2 | 3 | | 1 | 1 | 1 | | | 1 | 1 |
| 156 | 8.0 | (8.96) | | | | | | | | | 4 | 3 | | 4 | 4 | 5 | 4 | 2 | 5 | | | 4 | 4 |
| | 4.0 | (4.48) | 2 | 3 | 2 | 3 | 5 | 5 | 3 | 4 | 4 | 2 | 5 | 4 | 4 | 4 | 2 | 2 | 4 | 2 | 3 | 3 |
| | 2.0 | (2.24) | 1 | 2 | 2 | 2 | 5 | 4 | 2 | 3 | 2 | 2 | 5 | 4 | 3 | 3 | 2 | 2 | 3 | 1 | 1 | 1 |
| | 1.0 | (1.12) | 1 | 2 | 1 | 2 | 3 | 3 | 1 | 3 | 3 | 1 | 4 | 3 | 2 | 1 | 1 | 1 | 1 | 1 | 1 | 1 |
| 157 | 8.0 | (8.96) | | | | | | | | | 5 | 4 | | 5 | 5 | 5 | 5 | 4 | 5 | | | 4 | 5 |
| | 4.0 | (4.48) | 3 | 4 | 4 | 4 | 5 | 5 | 3 | 5 | 5 | 3 | 5 | 5 | 4 | 5 | 4 | 4 | 5 | 4 | 4 | 4 |
| | 2.0 | (2.24) | 2 | 4 | 2 | 3 | 5 | 5 | 3 | 5 | 4 | 3 | 5 | 5 | 4 | 5 | 3 | 3 | 5 | 3 | 4 | 4 |
| | 1.0 | (1.12) | 2 | 3 | 2 | 3 | 5 | 5 | 3 | 5 | 3 | 2 | 5 | 5 | 4 | 5 | 4 | 2 | 5 | 3 | 3 | 3 |
| | 1.0 | (1.12) | 1 | 2 | 2 | 2 | 5 | 5 | 2 | 4 | 3 | 2 | 5 | 5 | 5 | 3 | 3 | 5 | 4 | 3 | 3 |
| | 0.5 | (0.56) | 1 | 1 | 1 | 2 | 5 | 5 | 2 | 3 | 3 | 1 | 4 | 3 | 4 | 4 | 1 | 2 | 4 | 2 | 3 | 3 |
| | 0.25 | (0.28) | 1 | 1 | 1 | 2 | 5 | 4 | 2 | 2 | 1 | 1 | 4 | 3 | 2 | 4 | 1 | 1 | 4 | 2 | 2 | 3 |

TABLE III

Postemergence

| Example No. of Compound tested | Rate of Appln. lbs/acre | (kg/ha) | Corn | Tomato | Large Crabgrass | Pigweed | Foxtail | Velvetleaf | Morningglory | Zinnia | Barnyard Grass | Mustard | Wild Oats |
|---|---|---|---|---|---|---|---|---|---|---|---|---|---|
| 1 | 8.0 | (8.96) | 1 | | 4 | 4 | 3 | 5 | 3 | 4 | | | |
| | 4.0 | (4.48) | 3 | | ˙4 | 5 | 4 | 4 | 3 | 4 | | | |

TABLE III-continued

Postemergence

| Cmpd | lb/A | (kg/ha) | | | | | | | | | | | |
|---|---|---|---|---|---|---|---|---|---|---|---|---|---|
| | 2.0 | (2.24) | 1 | | 4 | 5 | 4 | 4 | 3 | 4 | | | |
| | 1.0 | (1.12) | 1 | | 4 | 5 | 3 | 3 | 4 | 4 | | | |
| | 1.0 | (1.12) | 1 | | 4 | 4 | 3 | 3 | 3 | 3 | | | |
| | 0.5 | (0.56) | 1 | | 3 | 4 | 2 | 3 | 3 | 3 | | | |
| | 0.25 | (0.28) | 1 | | 2 | 4 | 2 | 2 | 3 | 3 | | | |
| 2 | 8.0 | (8.96) | 2 | | 4 | 4 | 3 | 3 | 2 | 3 | | | |
| | 4.0 | (4.48) | 1 | | 2 | 4 | 2 | 2 | 1 | 3 | | | |
| | 2.0 | (2.24) | 1 | | 1 | 4 | 1 | 2 | 1 | 2 | | | |
| | 1.0 | (1.12) | 1 | | 2 | 3 | 2 | 2 | 1 | 3 | | | |
| 3 | 8.0 | (8.96) | 1 | | 4 | 4 | 4 | 4 | 3 | 4 | | | |
| | 4.0 | (4.48) | 1 | | 4 | 5 | 3 | 4 | 3 | 4 | | | |
| | 2.0 | (2.24) | 1 | | 4 | 5 | 3 | 4 | 3 | 3 | | | |
| | 1.0 | (1.12) | 1 | | 4 | 5 | 2 | 4 | 3 | 3 | | | |
| | 1.0 | (1.12) | 1 | | 4 | | 3 | 4 | 3 | 4 | | | |
| | 0.50 | (0.56) | 1 | | 3 | 4 | 3 | 3 | 2 | 3 | | | |
| | 0.25 | (0.28) | 1 | | 3 | 4 | 2 | 2 | 1 | 3 | | | |
| 4 | 8.0 | (8.96) | | 4 | 5 | 5 | 3 | 4 | 4 | 3 | 3 | 4 | 3 |
| | 4.0 | (4.48) | | 2 | 2 | 4 | 3 | 3 | 3 | 3 | 2 | 3 | 2 |
| | 2.0 | (2.24) | | 1 | 2 | 3 | 1 | 2 | 3 | 2 | 2 | 2 | 2 |
| | 1.0 | (1.12) | | 1 | 2 | 2 | 1 | 2 | 1 | 1 | 1 | 3 | 1 |
| 5 | 8.0 | (8.96) | 1 | | 2 | 3 | 2 | 3 | 2 | 2 | | | |
| 6 | 8.0 | (8.96) | 1 | | 4 | 3 | 1 | 3 | 1 | 3 | | | |
| 7 | 8.0 | (8.96) | 1 | | 4 | 3 | 1 | 1 | 1 | 3 | | | |
| 8 | 8.0 | (8.96) | 1 | | 2 | 5 | 2 | 3 | 2 | 3 | | | |
| | 4.0 | (4.48) | 1 | | 4 | 4 | 2 | 4 | 3 | 3 | | | |
| | 2.0 | (2.24) | 1 | | 3 | 5 | 2 | 3 | 3 | 3 | | | |
| | 1.0 | (1.12) | 1 | | 2 | 3 | 2 | 3 | 3 | 3 | | | |
| 9 | 8.0 | (8.96) | 1 | | 2 | 2 | 2 | 3 | 2 | 1 | | | |
| | 8.0 | (8.96) | 1 | | 1 | 1 | 1 | 2 | 1 | 2 | | | |
| 10 | 8.0 | (8.96) | 1 | | 1 | 2 | 1 | 1 | 1 | 3 | | | |
| 11 | 8.0 | (8.96) | | 1 | 1 | 1 | 1 | 1 | 1 | 1 | 1 | 1 | 1 |
| 12 | 8.0 | (8.96) | | 1 | 2 | 2 | 4 | 2 | 2 | 2 | 3 | 2 | 2 |
| 13 | 8.0 | (8.96) | | 1 | 1 | 1 | 1 | 1 | 1 | 1 | 1 | 1 | 1 |
| 14 | 8.0 | (8.96) | | 1 | 1 | 2 | 3 | 1 | 2 | 3 | 1 | 3 | 1 |
| 15 | 8.0 | (8.96) | 1 | | 1 | 1 | 1 | 1 | 1 | 1 | | | |
| 16 | 8.0 | (8.96) | 1 | | 3 | 3 | 1 | 3 | 2 | 2 | | | |
| 17 | 8.0 | (8.96) | 1 | | 2 | 2 | 1 | 1 | 2 | 2 | | | |
| 18 | 8.0 | (8.96) | 1 | | 4 | 3 | 1 | 2 | 2 | 3 | | | |
| 19 | 8.0 | (8.96) | 2 | | 4 | 5 | 4 | 5 | 3 | 3 | | | |
| | 4.0 | (4.48) | 2 | | 3 | 4 | 2 | 3 | 3 | 3 | | | |
| | 2.0 | (2.24) | 1 | | 3 | 3 | 3 | 3 | 3 | 3 | | | |
| | 1.0 | (1.12) | 1 | | 3 | 3 | 2 | 3 | 2 | 3 | | | |
| 20 | 8.0 | (8.96) | 1 | | 4 | 4 | 3 | 4 | 3 | 4 | | | |
| | 4.0 | (4.48) | 2 | | 4 | 4 | 3 | 4 | 4 | 3 | | | |
| | 2.0 | (2.24) | 1 | | 3 | 4 | 2 | 4 | 3 | 3 | | | |
| | 1.0 | (1.12) | 1 | | 3 | 4 | 2 | 3 | 3 | 3 | | | |
| 21 | 8.0 | (8.96) | | 2 | 2 | 2 | 2 | 2 | 3 | 1 | 4 | 2 | 1 |
| 22 | 8.0 | (8.96) | | 1 | 1 | 1 | 1 | 1 | 1 | 1 | 1 | 1 | 1 |
| 23 | 8.0 | (8.96) | 1 | | 4 | 4 | 3 | 2 | 3 | 3 | | | |
| | 4.0 | (4.48) | 1 | | 3 | 4 | 3 | 2 | 2 | 3 | | | |
| | 2.0 | (2.24) | 1 | | 3 | 4 | 1 | 3 | 3 | 2 | | | |
| | 1.0 | (1.12) | 1 | | 3 | 3 | 1 | 2 | 1 | 1 | | | |
| 24 | 8.0 | (8.96) | 1 | | 4 | 5 | 4 | 3 | 3 | 4 | | | |
| | 4.0 | (4.48) | 1 | | 4 | 5 | 3 | 3 | 3 | 4 | | | |
| | 2.0 | (2.24) | 1 | | 4 | 3 | 3 | 3 | 3 | 3 | | | |
| | 1.0 | (1.12) | 1 | | 3 | 4 | 2 | 3 | 2 | 3 | | | |
| 25 | 8.0 | (8.96) | | 2 | 3 | 1 | 3 | 2 | 1 | 2 | 1 | 2 | 1 |
| 26 | 8.0 | (8.96) | 1 | | 1 | 3 | 1 | 1 | 1 | 1 | | | |
| 27 | 8.0 | (8.96) | 1 | | 3 | 4 | 1 | 1 | 3 | 2 | | | |
| 28 | 8.0 | (8.96) | | 2 | 3 | 3 | 3 | 1 | 1 | 2 | 2 | 3 | 1 |
| 29 | 8.0 | (8.96) | 1 | | 1 | 1 | 1 | 2 | 1 | 1 | | | |
| 30 | 8.0 | (8.96) | 1 | | 2 | 1 | 1 | 2 | 1 | 1 | | | |
| 31 | 8.0 | (8.96) | 1 | | 4 | 5 | 3 | 4 | 3 | 3 | | | |
| | 4.0 | (4.48) | 1 | | 4 | 3 | 3 | 3 | 3 | 3 | | | |
| | 2.0 | (2.24) | 2 | | 2 | 3 | 2 | 2 | 3 | 3 | | | |
| | 1.0 | (1.12) | 1 | | 2 | 3 | 2 | 2 | 2 | 2 | | | |
| 32 | 8.0 | (8.96) | | 1 | | 1 | 1 | 1 | 1 | 1 | 1 | 2 | 1 |
| 33 | 8.0 | (8.96) | | 1 | 1 | 1 | 1 | 1 | 2 | 2 | 1 | 2 | 1 |
| 34 | 8.0 | (8.96) | 1 | | 3 | 4 | 2 | 2 | 2 | 3 | | | |
| 35 | 8.0 | (8.96) | 2 | | 4 | 5 | 3 | 4 | 4 | 4 | | | |
| | 4.0 | (4.48) | 1 | | 3 | 4 | 2 | 3 | 3 | 3 | | | |
| | 2.0 | (2.24) | 1 | | 1 | 4 | 2 | 2 | 3 | 3 | | | |
| | 1.0 | (1.12) | 1 | | 1 | 4 | 2 | 2 | 3 | 2 | | | |
| 36 | 8.0 | (8.96) | 3 | | 4 | 5 | 3 | 4 | 3 | 4 | | | |
| | 4.0 | (4.48) | 1 | | 4 | 4 | 3 | 5 | 3 | 4 | | | |
| | 2.0 | (2.24) | 1 | | 3 | 4 | 3 | 4 | 3 | 3 | | | |
| | 1.0 | (1.12) | 1 | | 3 | 4 | 3 | 3 | 3 | 4 | | | |
| | 1.0 | (1.12) | | | 2 | 5 | 2 | 3 | 2 | 2 | | | |
| | 0.50 | (0.56) | | | 1 | 5 | 2 | 3 | 1 | 2 | | | |
| | 0.25 | (0.28) | | | 1 | 4 | 1 | 3 | 1 | 1 | | | |
| 37 | 8.0 | (8.96) | 1 | | 1 | 1 | 1 | 1 | 1 | 1 | | | |

TABLE III-continued

Postemergence

| | | | | | | | | | | | | |
|---|---|---|---|---|---|---|---|---|---|---|---|---|
| 38 | 8.0 | (8.96) | 1 | | 1 | 1 | 1 | 1 | 1 | 1 | | | |
| 39 | 8.0 | (8.96) | 1 | | 1 | 1 | 1 | 2 | 2 | 3 | | | |
| 40 | 8.0 | (8.96) | 1 | | 4 | 4 | 4 | 3 | 4 | 4 | | | |
| | 4.0 | (4.48) | 1 | | 4 | 5 | 4 | 3 | 3 | 4 | | | |
| | 2.0 | (2.24) | 1 | | 4 | 4 | 3 | 3 | 3 | 3 | | | |
| | 1.0 | (1.12) | 1 | | 3 | 4 | 2 | 3 | 2 | 3 | | | |
| 41 | 8.0 | (8.96) | | 1 | 1 | 1 | 1 | 1 | 1 | 2 | 1 | 1 | 1 |
| 42 | 8.0 | (8.96) | 3 | | 4 | 5 | 4 | 4 | 3 | 3 | | | |
| | 4.0 | (4.48) | 2 | | 3 | 3 | 3 | 3 | 2 | 2 | | | |
| | 2.0 | (2.24) | 2 | | 3 | 3 | 4 | 3 | 1 | 3 | | | |
| | 1.0 | (1.12) | 1 | | 3 | 3 | 3 | 3 | 1 | 2 | | | |
| 43 | 8.0 | (8.96) | 2 | | 4 | 4 | 3 | 4 | 3 | 3 | | | |
| | 4.0 | (4.48) | 1 | | 3 | 4 | 3 | 3 | 3 | 3 | | | |
| | 2.0 | (2.24) | 1 | | 3 | 3 | 3 | 2 | 2 | 3 | | | |
| | 1.0 | (1.12) | 1 | | 3 | 2 | 2 | 2 | 3 | 2 | | | |
| 44 | 8.0 | (8.96) | 1 | | 3 | 4 | 3 | 3 | 3 | 3 | | | |
| 45 | 8.0 | (8.96) | | 2 | 4 | 3 | 3 | 2 | 2 | 1 | 1 | 3 | 1 |
| 46 | 8.0 | (8.96) | | 4 | 5 | 5 | 4 | 5 | 2 | 4 | 4 | 4 | 2 |
| | 4.0 | (4.48) | | 4 | 4 | 5 | 4 | 4 | 4 | 4 | 4 | 5 | 2 |
| | 2.0 | (2.24) | | 4 | 5 | 5 | 4 | 5 | 4 | 4 | 4 | 4 | 3 |
| | 1.0 | (1.12) | | 4 | 5 | 5 | 4 | 4 | 3 | 3 | 4 | 4 | 2 |
| | 1.0 | (1.12) | | 4 | 3 | 5 | 4 | 5 | 3 | 3 | 2 | 4 | 2 |
| | 0.50 | (0.56) | | 2 | 3 | 5 | 3 | 3 | 2 | 3 | 1 | 3 | 1 |
| | 0.25 | (0.28) | | 2 | 1 | 3 | 2 | 3 | 2 | 2 | 1 | 3 | 1 |
| 47 | 8.0 | (8.96) | 3 | | 5 | 5 | 4 | 4 | 3 | 3 | | | |
| | 4.0 | (4.48) | 1 | | 4 | 5 | 4 | 4 | 3 | 3 | | | |
| | 2.0 | (2.24) | 1 | | 3 | 5 | 3 | 4 | 3 | 3 | | | |
| | 1.0 | (1.12) | 1 | | 3 | 4 | 3 | 3 | 3 | 3 | | | |
| 48 | 8.0 | (8.96) | | 3 | 5 | 4 | 3 | 5 | 3 | 3 | 4 | 4 | 2 |
| | 1.0 | (1.12) | | 2 | 4 | 4 | 3 | 3 | 2 | 2 | 2 | 3 | 2 |
| | 0.50 | (0.56) | | 1 | 3 | 4 | 2 | 3 | 2 | 3 | 1 | 3 | 1 |
| | 0.25 | (0.28) | | 2 | 3 | 3 | 2 | 2 | 2 | 2 | 2 | 2 | 1 |
| 49 | 8.0 | (8.96) | 1 | | 2 | 4 | 2 | 3 | 3 | 2 | | | |
| 50 | 8.0 | (8.96) | 1 | | 3 | 3 | 2 | 2 | 2 | 2 | | | |
| 51 | 8.0 | (8.96) | | 2 | 1 | 1 | 1 | 1 | 2 | 2 | 2 | 2 | 1 |
| 52 | 8.0 | (8.96) | | 3 | 3 | 4 | 2 | 2 | 2 | 4 | 3 | 4 | 2 |
| | 4.0 | (4.48) | | 3 | 3 | 3 | 2 | 3 | 2 | 3 | 2 | 5 | 2 |
| | 2.0 | (2.24) | | 2 | 3 | 3 | 2 | 4 | 2 | 2 | 1 | 4 | 2 |
| | 1.0 | (1.12) | | 1 | 1 | 3 | 2 | 2 | 2 | 2 | 1 | 3 | 2 |
| 53 | 8.0 | (8.96) | 1 | | 1 | 1 | 1 | 1 | 1 | 1 | | | |
| 54 | 8.0 | (8.96) | 1 | | 1 | 1 | 1 | 1 | 1 | 1 | | | |
| 55 | 8.0 | (8.96) | 1 | | 4 | 5 | 4 | 4 | 3 | 4 | | | |
| | 4.0 | (4.48) | 1 | | 4 | 4 | 2 | 2 | 3 | 4 | | | |
| | 2.0 | (2.24) | 1 | | 4 | 5 | 2 | 2 | 2 | 4 | | | |
| | 1.0 | (1.12) | 1 | | 3 | 4 | 2 | 1 | 2 | 3 | | | |
| 56 | 8.0 | (8.96) | 2 | | 3 | 5 | 2 | 2 | 3 | 3 | | | |
| | 4.0 | (4.48) | 1 | | 3 | 4 | 2 | 1 | 2 | 2 | | | |
| | 2.0 | (2.24) | 1 | | 2 | 3 | 2 | 1 | 2 | 2 | | | |
| | 1.0 | (1.12) | 1 | | 2 | 3 | 2 | 1 | 2 | 2 | | | |
| 57 | 8.0 | (8.96) | 1 | | 4 | 3 | 1 | 2 | 1 | 1 | | | |
| 58 | 8.0 | (8.96) | | 2 | 4 | 5 | 4 | 4 | 1 | 4 | 3 | 3 | 1 |
| | 4.0 | (4.48) | | 2 | 4 | 4 | 4 | 4 | 2 | 4 | 2 | 2 | 1 |
| | 2.0 | (2.24) | | 1 | 4 | 4 | 3 | 4 | 1 | 3 | 2 | 2 | 2 |
| | 1.0 | (1.12) | | 1 | 4 | 4 | 3 | 3 | 1 | 3 | 1 | 2 | 1 |
| | 1.0 | (1.12) | | 2 | 3 | 4 | 4 | 3 | 2 | 2 | 2 | 3 | 1 |
| | 0.50 | (0.56) | | 1 | 3 | 4 | 2 | 3 | 1 | 2 | 2 | 2 | 1 |
| | 0.25 | (0.28) | | 1 | 1 | 3 | 2 | 1 | 1 | 2 | 1 | 1 | 1 |
| 59 | 8.0 | (8.96) | 1 | | 4 | 5 | 3 | 5 | 3 | 4 | | | |
| | 4.0 | (4.48) | 1 | 3 | 4 | 3 | 3 | 1 | 4 | | | | |
| | 2.0 | (2.24) | 2 | | 4 | 4 | 4 | 3 | 2 | 3 | | | |
| | 1.0 | (1.12) | 1 | | 3 | 4 | 3 | 3 | 2 | 3 | | | |
| 60 | 8.0 | (8.96) | 3 | | 4 | 4 | 3 | 4 | 3 | 4 | | | |
| | 4.0 | (4.48) | 1 | | 4 | 4 | 2 | 3 | 3 | 3 | | | |
| | 2.0 | (2.24) | 1 | | 2 | 2 | 1 | 2 | 2 | 2 | | | |
| | 1.0 | (1.12) | 1 | | 1 | 1 | 1 | 1 | 1 | 1 | | | |
| 61 | 8.0 | (8.96) | 2 | | 4 | 4 | 3 | 4 | 3 | 3 | | | |
| | 4.0 | (4.48) | 1 | | 4 | 4 | 2 | 3 | 3 | 3 | | | |
| | 2.0 | (2.24) | 1 | | 3 | 2 | 1 | 3 | 3 | 3 | | | |
| | 1.0 | (1.12) | 1 | | 3 | 2 | 1 | 1 | 2 | 2 | | | |
| 62 | 8.0 | (8.96) | 1 | | 4 | 3 | 4 | 4 | 2 | 4 | | | |
| | 4.0 | (4.48) | 1 | | 4 | 5 | 3 | 3 | 3 | 4 | | | |
| | 2.0 | (2.24) | 1 | | 4 | 4 | 3 | 2 | 3 | 4 | | | |
| | 1.0 | (1.12) | 1 | | 4 | 4 | 1 | 2 | 3 | 3 | | | |
| | 1.0 | (1.12) | 1 | | 4 | 4 | 2 | 3 | 2 | 4 | | | |
| | 0.50 | (0.56) | 1 | | 4 | 4 | 2 | 2 | 2 | 3 | | | |
| | 0.25 | (0.28) | 1 | | 3 | 3 | 2 | 2 | 2 | 3 | | | |
| 63 | 8.0 | (8.96) | 1 | | 1 | 3 | 1 | 1 | 2 | 2 | | | |
| 64 | 8.0 | (8.96) | | 5 | 4 | 5 | 4 | 4 | 3 | 4 | 3 | 5 | 2 |
| | 4.0 | (4.48) | | 2 | 1 | 4 | 2 | 1 | 1 | 2 | 1 | 4 | 1 |
| | 2.0 | (2.24) | | 2 | 1 | 3 | 1 | 1 | 1 | 2 | 1 | 3 | 2 |
| | 1.0 | (1.12) | | 1 | 2 | 3 | 2 | 1 | 2 | 2 | 1 | 3 | 1 |

TABLE III-continued

| | | | | | | | | | | | | | |
|---|---|---|---|---|---|---|---|---|---|---|---|---|---|
| | | | | Postemergence | | | | | | | | | |
| 65 | 8.0 | (8.96) | | 2 | 2 | 4 | 2 | 3 | 3 | 2 | 2 | 4 | 2 |
| | 4.0 | (4.48) | | 3 | 3 | 4 | 3 | 4 | 3 | 4 | 3 | 3 | 3 |
| | 2.0 | (2.24) | | 2 | 4 | 3 | 2 | 3 | 2 | 2 | 2 | 2 | 1 |
| | 1.0 | (1.12) | | 2 | 2 | 3 | 2 | 3 | 2 | 2 | 2 | 2 | 1 |
| 66 | 8.0 | (8.96) | 2 | | 5 | 5 | 3 | 4 | 2 | 4 | | | |
| | 4.0 | (4.48) | 2 | | 4 | 3 | 3 | 4 | 2 | 3 | | | |
| | 2.0 | (2.24) | 1 | | 3 | 4 | 3 | 4 | 2 | 3 | | | |
| | 1.0 | (1.12) | 1 | | 4 | 3 | 3 | 3 | 2 | 4 | | | |
| | 1.0 | (1.12) | 2 | | 3 | 5 | 3 | 3 | 4 | 4 | | | |
| | 0.50 | (0.56) | 2 | | 3 | 5 | 3 | 4 | 2 | 3 | | | |
| | 0.25 | (0.28) | 1 | | 3 | 4 | 2 | 3 | 2 | 3 | | | |
| 67 | 8.0 | (8.96) | 3 | | 4 | 5 | 2 | 3 | 3 | 3 | | | |
| | 4.0 | (4.48) | 1 | | 2 | 4 | 2 | 2 | 3 | 2 | | | |
| | 2.0 | (2.24) | 1 | | 3 | 4 | 2 | 2 | 2 | 2 | | | |
| | 1.0 | (1.12) | 1 | | 1 | 4 | 1 | 1 | 1 | 2 | | | |
| 68 | 8.0 | (8.96) | | 3 | 4 | 5 | 4 | 2 | 2 | 3 | 2 | 4 | 1 |
| | 4.0 | (4.48) | | 2 | 4 | 5 | 2 | 1 | 1 | 3 | 2 | 4 | 1 |
| | 2.0 | (2.24) | | 2 | 3 | 4 | 2 | 1 | 2 | 3 | 1 | 4 | 1 |
| | 1.0 | (1.12) | | 1 | 3 | 3 | 1 | 1 | 1 | 2 | 1 | 2 | 1 |
| 69 | 8.0 | (8.96) | | 3 | 2 | 4 | 4 | 4 | 2 | 3 | 1 | 4 | 1 |
| | 4.0 | (4.48) | | 3 | 4 | 4 | 2 | 2 | 3 | 4 | 3 | 4 | 1 |
| | 2.0 | (2.24) | | 2 | 4 | | 2 | 2 | 3 | 3 | 1 | 4 | 1 |
| | 1.0 | (1.12) | | 2 | 3 | 4 | 1 | 2 | 2 | 3 | 1 | 3 | 1 |
| 70 | 8.0 | (8.96) | 2 | 4 | 4 | 4 | 5 | 3 | 4 | | | | |
| | 4.0 | (4.48) | 1 | 3 | 3 | 3 | 4 | 2 | 3 | | | | |
| | 2.0 | (2.24) | 3 | 3 | 5 | 3 | 5 | 3 | 4 | | | | |
| | 1.0 | (1.12) | 1 | 3 | 4 | 3 | 4 | 2 | 3 | | | | |
| | 1.0 | (1.12) | 2 | 4 | 5 | 4 | 4 | 4 | 4 | | | | |
| | 0.50 | (0.56) | 2 | 4 | 4 | 3 | 4 | 2 | 4 | | | | |
| | 0.25 | (0.28) | 1 | 3 | 4 | 2 | 3 | 2 | 3 | | | | |
| 71 | 8.0 | (8.96) | 2 | | 4 | 4 | 2 | 4 | 3 | 4 | | | |
| | 4.0 | (4.48) | 1 | | 4 | 4 | 4 | 4 | 3 | 3 | | | |
| | 2.0 | (2.24) | 1 | | 3 | 4 | 2 | 3 | 3 | 3 | | | |
| | 1.0 | (1.12) | 1 | | 4 | 3 | 3 | 3 | 3 | 3 | | | |
| 72 | 8.0 | (8.96) | 1 | | 1 | 3 | 1 | 1 | 1 | 1 | | | |
| | 8.0 | (8.96) | 1 | | 3 | 4 | 2 | 3 | 3 | 3 | | | |
| 73 | 8.0 | (8.96) | 1 | | 3 | 4 | 1 | 1 | 1 | 2 | | | |
| | 8.0 | (8.96) | 1 | | 4 | 4 | 3 | 3 | 2 | 3 | | | |
| | 4.0 | (4.48) | 1 | | 3 | 4 | 2 | 3 | 2 | 2 | | | |
| | 2.0 | (2.24) | 1 | | 4 | 3 | 1 | 3 | 2 | 2 | | | |
| | 1.0 | (1.12) | 1 | | 3 | 2 | 1 | 1 | 1 | 1 | | | |
| 74 | 8.0 | (8.96) | 1 | | 1 | 3 | 1 | 2 | 1 | 2 | | | |
| 75 | 8.0 | (8.96) | | 1 | 1 | 2 | 3 | 1 | 1 | 2 | 1 | 2 | 1 |
| 76 | 8.0 | (8.96) | | 3 | 4 | 4 | 4 | 4 | 2 | 3 | 2 | 4 | 2 |
| | 4.0 | (4.48) | | 3 | 3 | 5 | 2 | 4 | 2 | 3 | 1 | 4 | 2 |
| | 2.0 | (2.24) | | 2 | 3 | 4 | 2 | 4 | 1 | 3 | 1 | 4 | 1 |
| | 1.0 | (1.12) | | 2 | 3 | 3 | 2 | 2 | 1 | 2 | 1 | 3 | 1 |
| 77 | 8.0 | (8.96) | | 5 | 4 | 5 | 5 | 5 | 4 | 4 | 4 | 5 | 3 |
| | 4.0 | (4.48) | | 4 | 4 | 5 | 3 | 5 | 4 | 5 | 4 | 4 | 2 |
| | 2.0 | (2.24) | | 5 | 4 | 5 | 4 | 5 | 4 | 3 | 4 | 4 | 2 |
| | 1.0 | (1.12) | | 4 | 3 | 5 | 4 | 5 | 4 | 3 | 4 | 4 | 2 |
| | 1.0 | (1.12) | | 4 | 3 | 5 | 3 | 5 | 3 | 3 | 1 | 3 | 2 |
| | 0.50 | (0.56) | | 3 | 3 | 5 | 2 | 3 | 1 | 2 | 1 | 3 | 1 |
| | 0.25 | (0.28) | | 2 | 2 | 4 | 1 | 3 | 1 | 2 | 1 | 3 | 1 |
| 78 | 8.0 | (8.96) | | 3 | 2 | 5 | 3 | 2 | 1 | 2 | 2 | 3 | 1 |
| | 4.0 | (4.48) | | 2 | 1 | 3 | 1 | 1 | 1 | 1 | 2 | 3 | 1 |
| | 2.0 | (2.24) | | 1 | 1 | 1 | 1 | 1 | 1 | 2 | 1 | 3 | 1 |
| | 1.0 | (1.12) | | 1 | 1 | 1 | 1 | 1 | 1 | 1 | 1 | 1 | 1 |
| 79 | 8.0 | (8.96) | | 1 | 2 | 3 | 2 | 1 | 1 | 2 | 1 | 2 | 1 |
| 80 | 8.0 | (8.96) | | 1 | 3 | 4 | 3 | 2 | 1 | 2 | 1 | 3 | 1 |
| 82 | 8.0 | (8.96) | | 3 | 3 | 4 | 3 | 2 | 1 | 3 | 1 | 4 | 1 |
| | 4.0 | (4.48) | | 2 | 2 | 2 | 2 | 2 | 2 | 2 | 1 | 4 | 1 |
| | 2.0 | (2.24) | | 2 | 1 | 1 | 3 | 2 | 2 | 2 | 2 | 3 | 1 |
| | 1.0 | (1.12) | | 1 | 1 | 1 | 2 | 2 | 1 | 2 | 1 | 3 | 1 |
| 83 | 8.0 | (8.96) | | 1 | 1 | 1 | 1 | 1 | 1 | 1 | 1 | 1 | 1 |
| 84 | 8.0 | (8.96) | | 5 | 5 | 5 | 4 | 4 | 4 | 5 | 3 | 5 | 4 |
| | 4.0 | (4.48) | | 2 | 4 | 5 | 2 | 2 | 2 | 4 | 1 | 4 | 2 |
| | 2.0 | (2.24) | | 2 | 2 | 2 | 2 | 2 | 1 | 3 | 1 | 4 | 2 |
| | 1.0 | (1.12) | | 1 | 4 | 4 | 2 | 1 | 2 | 2 | 1 | 5 | 1 |
| 85 | 8.0 | (8.96) | | 2 | 2 | 5 | 2 | 3 | 3 | 3 | 1 | 4 | 2 |
| | 4.0 | (4.48) | | 4 | 2 | 4 | 2 | 3 | 3 | 5 | 1 | 5 | 2 |
| | 2.0 | (2.24) | | 3 | 2 | 3 | 2 | 2 | 2 | 3 | 1 | 5 | 3 |
| | 1.0 | (1.12) | | 2 | 1 | 4 | 2 | 2 | 2 | 2 | 1 | 4 | 1 |
| | 1.0 | (1.12) | | 2 | 2 | 4 | 2 | 3 | 1 | 1 | 1 | 3 | 2 |
| | 0.5 | (0.56) | | 2 | 2 | 2 | 2 | 2 | 1 | 1 | 1 | 3 | 2 |
| | 0.25 | (0.28) | | 1 | 1 | | 1 | 1 | 1 | 1 | 1 | 2 | 1 |
| 86 | 8.0 | (8.96) | | 4 | 2 | 5 | 4 | 4 | 3 | 4 | 2 | 5 | 2 |
| | 4.0 | (4.48) | | 4 | 4 | 4 | 4 | 5 | 4 | 5 | 1 | 5 | 2 |
| | 2.0 | (2.24) | | 4 | 1 | 3 | 3 | 4 | 4 | 4 | 1 | 5 | 2 |
| | 1.0 | (1.12) | | 4 | 4 | 2 | 2 | 5 | 4 | 4 | 1 | 4 | 2 |
| | 1.0 | (1.12) | | 5 | 2 | 3 | 2 | 3 | 2 | 3 | 1 | 5 | 2 |

TABLE III-continued

Postemergence

| Example No. of Compound Tested | Rate of Appln. lbs/acre | (kg/ha) | Tomato | Barn-Yard grass | Large Crab-grass | Mustard | Pig-weed | Fox-tail | Wild Oats | Velvet-leaf | Morning-glory | Zinnia |
|---|---|---|---|---|---|---|---|---|---|---|---|---|
| | 0.5 | (0.56) | 5 | 2 | 3 | 3 | 3 | 2 | 1 | 1 | 4 | 2 |
| | 0.25 | (0.28) | 3 | 1 | 1 | 2 | 3 | 1 | 2 | 1 | 4 | 2 |
| 87 | 8.0 | (8.96) | 5 | 4 | 5 | 2 | 4 | 2 | 5 | 2 | 5 | 2 |
| | 2.0 | (2.24) | 5 | 4 | 2 | 2 | 4 | 2 | 5 | 1 | 5 | 1 |
| | 1.0 | (1.12) | 5 | 4 | 5 | 2 | 3 | 2 | 5 | 1 | 5 | 1 |
| | 1.0 | (1.12) | 4 | 2 | 2 | 2 | 2 | 1 | 2 | 1 | 4 | 2 |
| | 0.5 | (0.56) | 4 | 4 | 2 | 2 | 1 | 2 | 4 | 1 | 4 | 2 |
| | 0.5 | (0.56) | 2 | 2 | 3 | 2 | 2 | 1 | 2 | 1 | 4 | 2 |
| | 0.25 | (0.28) | 1 | 1 | 2 | 2 | 1 | 1 | 1 | 1 | 3 | 1 |
| 88 | 8.0 | (8.96) | 5 | 5 | 5 | 4 | 5 | 5 | 5 | 3 | 5 | 4 |
| | 4.0 | (4.48) | 5 | 5 | 3 | 3 | 5 | 4 | 5 | 3 | 5 | 4 |
| | 2.0 | (2.24) | 5 | 4 | 4 | 2 | 4 | 4 | 5 | 2 | 5 | 4 |
| | 1.0 | (1.12) | 5 | 4 | 3 | 2 | 3 | 4 | 5 | 1 | 5 | 2 |
| | 1.0 | (1.12) | 3 | 2 | | 2 | 4 | 2 | 4 | 2 | 4 | 2 |
| | 0.5 | (0.56) | 4 | 3 | 2 | 2 | 3 | 2 | 2 | 2 | 3 | 2 |
| | 0.25 | (0.28) | 2 | 2 | 1 | 2 | 2 | 2 | 2 | 2 | 2 | 2 |
| 89 | 8.0 | (8.96) | 3 | 2 | 4 | 2 | 2 | 3 | 5 | 1 | 4 | 2 |
| | 4.0 | (4.48) | 4 | 1 | 3 | 2 | 4 | 2 | 5 | 1 | 4 | 1 |
| | 2.0 | (2.24) | 3 | 2 | 3 | 2 | 1 | 2 | 3 | 1 | 4 | 1 |
| | 1.0 | (1.12) | 1 | 2 | 2 | 1 | 2 | 1 | 1 | 1 | 3 | 1 |
| 90 | 8.0 | (8.96) | 3 | 4 | 2 | 2 | 2 | 2 | 2 | 1 | 5 | 2 |
| | 4.0 | (4.48) | 1 | 3 | 2 | 3 | 1 | 1 | 2 | 1 | 4 | 1 |
| | 2.0 | (2.24) | 1 | 2 | 2 | 1 | 1 | 2 | 2 | 1 | 4 | 1 |
| | 1.0 | (1.12) | 1 | 2 | 2 | 1 | 1 | 1 | 2 | 1 | 4 | 1 |
| 91 | 8.0 | (8.96) | 5 | 4 | 3 | 2 | 4 | 3 | 5 | 2 | 5 | 2 |
| | 4.0 | (4.48) | 5 | 4 | 4 | 3 | 5 | 3 | 5 | 2 | 5 | 3 |
| | 2.0 | (2.24) | 5 | 4 | 4 | 5 | 5 | 5 | 5 | 2 | 5 | 5 |
| | 1.0 | (1.12) | 5 | 4 | 1 | 5 | 5 | 4 | 5 | 2 | 4 | 4 |
| | 1.0 | (1.12) | 4 | 2 | 5 | 2 | 2 | 2 | 3 | 2 | 4 | 3 |
| | 0.5 | (0.56) | 5 | 2 | 2 | 2 | 2 | 2 | 5 | 1 | 4 | 3 |
| | 0.25 | (0.28) | 4 | 2 | 2 | 2 | 2 | 2 | 2 | 2 | 4 | 3 |
| | 0.25 | (0.28) | 4 | 2 | 5 | 3 | 4 | 2 | 5 | 2 | 4 | 3 |
| | 0.125 | (0.14) | 3 | 1 | 4 | 2 | 3 | 2 | 3 | 1 | 3 | 2 |
| | 0.0625 | (0.07) | 2 | 1 | 3 | 1 | 2 | 1 | 3 | 1 | 2 | 1 |
| 92 | 8.0 | (8.96) | 2 | 4 | 4 | 2 | 5 | 4 | 4 | 2 | 4 | 3 |
| | 4.0 | (4.48) | 2 | 3 | 5 | 3 | 5 | 3 | 3 | 2 | 2 | 2 |
| | 2.0 | (2.24) | 1 | 2 | 4 | 2 | 3 | 2 | 2 | 2 | 2 | 2 |
| | 1.0 | (1.12) | 1 | 1 | 2 | 1 | 2 | 2 | 2 | 1 | 1 | 1 |
| 93 | 8.0 | (8.96) | 1 | 2 | 4 | 2 | 1 | 3 | 1 | 1 | 4 | 1 |
| | 4.0 | (4.48) | 1 | 3 | 3 | 1 | 1 | 1 | 2 | 1 | 3 | 1 |
| | 2.0 | (2.24) | 1 | 2 | 1 | 1 | 1 | 1 | 2 | 1 | 2 | 1 |
| | 1.0 | (1.12) | 1 | 1 | 1 | 1 | 1 | 1 | 1 | 1 | 2 | 1 |

| Example No. of Compound Tested | Rate of Appln. lbs/acre | (kg/ha) | Tomato | Barn-Yard grass | Large Crab-grass | Mustard | Pig-weed | Fox-tail | Wild Oats | Velvet-leaf | Morning-glory | Zinnia |
|---|---|---|---|---|---|---|---|---|---|---|---|---|
| 94 | 8.0 | (8.96) | 4 | 1 | 1 | 4 | | 2 | 1 | 4 | 2 | 2 |
| | 4.0 | (4.48) | 3 | 1 | 2 | 3 | 4 | 2 | 1 | 3 | 2 | 2 |
| | 2.0 | (2.24) | 2 | 1 | 2 | 2 | 4 | 2 | 1 | 3 | 2 | 2 |
| | 1.0 | (1.12) | 2 | 1 | 1 | 2 | 4 | 2 | 1 | 3 | 2 | 2 |
| 95 | 8.0 | (8.96) | 5 | 5 | 4 | 5 | 5 | 5 | 4 | 5 | 4 | 5 |
| | 4.0 | (4.48) | 5 | 3 | 3 | 5 | 5 | 5 | 3 | 5 | 4 | 4 |
| | 2.0 | (2.24) | 5 | 3 | 2 | 4 | 5 | 5 | 2 | 5 | 4 | 4 |
| | 1.0 | (1.12) | 4 | 1 | 3 | 3 | 5 | 4 | 2 | 4 | 4 | 2 |
| | 1.0 | (1.12) | 4 | 1 | 2 | 3 | 5 | 3 | 2 | 4 | 3 | 2 |
| | 0.5 | (0.56) | 3 | 1 | 1 | 2 | 5 | 3 | 2 | 4 | 3 | 2 |
| | 0.25 | (0.28) | 1 | 1 | 1 | 1 | 4 | 1 | 1 | 1 | 2 | 1 |
| 96 | 8.0 | (8.96) | 5 | 1 | 2 | 4 | 5 | 2 | 2 | 4 | 4 | 4 |
| | 4.0 | (4.48) | 3 | 1 | 1 | 2 | 5 | 1 | 1 | 2 | 3 | 2 |
| | 2.0 | (2.24) | 2 | 1 | 1 | 1 | 5 | 1 | 1 | 1 | 2 | 2 |
| | 1.0 | (1.12) | 2 | 1 | 1 | 1 | 4 | 1 | 1 | 1 | 2 | 2 |
| 97 | 8.0 | (8.96) | 5 | 5 | 3 | 5 | 5 | 5 | 3 | 5 | 5 | 5 |
| | 4.0 | (4.48) | 5 | 4 | 5 | 5 | 5 | 5 | 4 | 5 | 5 | 5 |
| | 2.0 | (2.24) | 5 | 4 | 5 | 4 | 5 | 5 | 4 | 5 | 4 | 5 |
| | 1.0 | (1.12) | 5 | 3 | 4 | 4 | 5 | 4 | 4 | 5 | 4 | 4 |
| | 1.0 | (1.12) | 5 | 1 | 4 | 4 | 5 | 3 | 3 | 4 | 4 | 4 |
| | 0.5 | (0.56) | 5 | 1 | 2 | 3 | 5 | 3 | 2 | 3 | 3 | 3 |
| | 0.25 | (0.28) | 4 | 1 | 2 | 2 | 5 | 2 | 2 | 3 | 3 | 3 |
| 98 | 8.0 | (8.96) | 5 | 4 | 5 | 5 | 5 | 4 | 4 | 5 | 5 | 5 |
| | 4.0 | (4.48) | 4 | 1 | 2 | 3 | 5 | 2 | 2 | 1 | 3 | 2 |
| | 2.0 | (2.24) | 2 | 1 | 2 | 1 | 5 | 1 | 2 | 1 | 2 | 1 |
| | 1.0 | (1.12) | 2 | 1 | 1 | 1 | 2 | 1 | 1 | 1 | 2 | 1 |
| 99 | 8.0 | (8.96) | 5 | 3 | 3 | 5 | 5 | 3 | 2 | 4 | 4 | 4 |
| | 4.0 | (4.48) | 3 | 1 | 1 | 3 | 5 | 2 | 1 | 1 | 2 | 2 |
| | 2.0 | (2.24) | 1 | 1 | 1 | 2 | 4 | 1 | 1 | 1 | 2 | 1 |
| | 1.0 | (1.12) | 1 | 1 | 1 | 2 | 2 | 1 | 1 | 1 | 1 | 1 |
| 100 | 8.0 | (8.96) | 5 | 2 | 3 | 4 | 5 | 2 | 3 | 4 | 4 | 4 |
| | 4.0 | (4.48) | 4 | 2 | 1 | 2 | 5 | 3 | 1 | 3 | 3 | 1 |
| | 2.0 | (2.24) | 3 | 1 | 1 | 2 | 5 | 1 | 1 | 1 | 2 | 2 |
| | 1.0 | (1.12) | 3 | 1 | 1 | 2 | 3 | 1 | 1 | 1 | 2 | 1 |

4,620,865

TABLE III-continued

Postemergence

| | | | | | | | | | | | | |
|---|---|---|---|---|---|---|---|---|---|---|---|---|
| 102 | 8.0 | (8.96) | 5 | 4 | 4 | 5 | 5 | 4 | 5 | 5 | 4 | 5 |
| | 4.0 | (4.48) | 5 | 2 | 4 | 5 | 5 | 4 | 4 | 5 | 4 | 5 |
| | 2.0 | (2.24) | 5 | 2 | 3 | 5 | 5 | 4 | 4 | 5 | 5 | 5 |
| | 1.0 | (1.12) | 4 | 2 | 2 | | 5 | 3 | 3 | 4 | 2 | 4 |
| | 1.0 | (1.12) | 3 | 2 | 5 | 4 | 5 | 3 | 2 | 4 | 3 | 3 |
| | 0.5 | (0.56) | 4 | 3 | 4 | 4 | 3 | 5 | 4 | 4 | 5 | 5 |
| | 0.25 | (0.28) | 5 | 2 | 4 | 4 | 3 | 4 | 2 | 3 | 5 | 4 |
| | 0.25 | (0.28) | 2 | 1 | 2 | 2 | 4 | 2 | 1 | 3 | 2 | 2 |
| | 0.125 | (0.14) | 1 | 1 | 2 | 2 | 3 | 1 | 1 | 2 | 1 | 2 |
| | 0.0625 | (0.07) | 2 | 1 | 2 | 2 | 2 | 1 | 1 | 1 | 1 | 1 |
| 103 | 8.0 | (8.96) | 5 | 4 | 4 | 5 | 5 | 5 | 4 | 4 | 5 | 5 |
| | 4.0 | (4.48) | 5 | 3 | 5 | 5 | 5 | 3 | 2 | 4 | 3 | 4 |
| | 2.0 | (2.24) | 5 | 4 | 4 | 5 | 5 | 4 | 3 | 5 | 5 | 5 |
| | 1.0 | (1.12) | 4 | 2 | 4 | 4 | 5 | 3 | 2 | 4 | 3 | 3 |
| | 1.0 | (1.12) | 3 | 1 | 3 | 4 | 5 | 3 | 2 | 4 | | 4 |
| | 0.5 | (0.56) | 3 | 2 | 3 | 4 | 5 | 2 | 1 | 4 | 3 | 3 |
| | 0.25 | (0.28) | 2 | 1 | 2 | 2 | 5 | 2 | 2 | 4 | 3 | 2 |
| | 0.25 | (0.28) | 1 | 1 | 4 | 2 | 4 | 2 | 1 | 3 | 2 | 2 |
| | 0.125 | (0.14) | 1 | 1 | 1 | 1 | | 1 | 1 | 1 | 1 | 1 |
| | 0.0625 | (0.07) | 1 | 1 | 1 | 1 | 1 | 1 | 1 | 1 | 1 | 1 |
| 104 | 8.0 | (8.96) | 4 | 2 | 4 | 5 | 5 | 3 | 3 | 4 | 3 | 4 |
| | 4.0 | (4.48) | 3 | 1 | 4 | 4 | 5 | 2 | 2 | 4 | 3 | 3 |
| | 2.0 | (2.24) | 2 | 1 | 3 | 3 | 5 | 2 | 1 | 3 | 2 | 2 |
| | 1.0 | (1.12) | 2 | 1 | 2 | 2 | 4 | 2 | 1 | 3 | 2 | 2 |
| 105 | 8.0 | (8.96) | 5 | 3 | 5 | 5 | 5 | 4 | 2 | 5 | 3 | 5 |
| | 4.0 | (4.48) | 4 | 1 | 3 | 4 | | 2 | 2 | 3 | 3 | 3 |
| | 2.0 | (2.24) | 2 | 1 | 4 | 3 | 3 | 3 | 1 | 3 | 3 | 3 |
| | 1.0 | (1.12) | 2 | 1 | 3 | | | 3 | 1 | 2 | 1 | 3 |
| 106 | 8.0 | (8.96) | 5 | 2 | 3 | 4 | 5 | 4 | 3 | 4 | 4 | 5 |
| | 4.0 | (4.48) | 4 | 5 | 5 | 3 | 5 | 3 | 1 | 4 | 2 | 1 |
| | 2.0 | (2.24) | 3 | 1 | 1 | 2 | 4 | 3 | 1 | 3 | 2 | 1 |
| | 1.0 | (1.12) | 1 | 1 | 1 | 2 | 3 | 3 | 1 | 1 | 2 | 1 |
| 107 | 8.0 | (8.96) | 5 | 3 | 3 | 4 | 5 | 2 | 2 | 4 | 3 | 3 |
| | 4.0 | (4.48) | 4 | 1 | 2 | 3 | 5 | 1 | 1 | 2 | 3 | 2 |
| | 2.0 | (2.24) | 3 | 1 | 1 | 4 | 5 | 1 | 1 | 1 | 3 | 1 |
| | 1.0 | (1.12) | 1 | 1 | 1 | 2 | 4 | 1 | 1 | 1 | 2 | 1 |
| 109 | 8.0 | (8.96) | 5 | 5 | 4 | 5 | 5 | 4 | 2 | 4 | 4 | 5 |
| | 4.0 | (4.48) | 5 | 3 | 4 | 5 | 5 | 3 | 2 | 3 | 4 | 5 |
| | 2.0 | (2.24) | 5 | 2 | 3 | 5 | 5 | 3 | 2 | 3 | 4 | 5 |
| | 1.0 | (1.12) | 4 | 2 | 3 | 5 | 5 | 5 | 2 | 2 | 4 | 4 |
| | 1.0 | (1.12) | 5 | 2 | 3 | 4 | 5 | 5 | 2 | 3 | 5 | 5 |
| | 0.5 | (0.56) | 5 | 2 | 2 | 3 | 5 | 4 | 3 | 3 | 4 | 5 |
| | 0.25 | (0.28) | 4 | 1 | 2 | 2 | 4 | 3 | 3 | 2 | 3 | 5 |
| 110 | 8.0 | (8.96) | 5 | 5 | 5 | 5 | 5 | 5 | 4 | 5 | 5 | 5 |
| | 4.0 | (4.48) | 5 | 5 | 5 | 5 | 5 | 5 | 4 | 5 | 5 | 5 |
| | 2.0 | (2.24) | 5 | 4 | 4 | 5 | 5 | 5 | 4 | 5 | 5 | 5 |
| | 1.0 | (1.12) | 5 | 4 | 3 | 5 | 5 | 4 | 3 | 4 | 4 | 5 |
| | 1.0 | (1.12) | 5 | 2 | 4 | 5 | 5 | 5 | 3 | 3 | 5 | 5 |
| | 0.5 | (0.56) | 3 | 2 | 3 | 4 | 5 | 4 | 1 | 2 | 4 | 5 |
| | 0.25 | (0.28) | 5 | 2 | 3 | 5 | 5 | 5 | 2 | 3 | 5 | 5 |
| 112 | 8.0 | (8.96) | 5 | 4 | 5 | 5 | 5 | 5 | 4 | 5 | 5 | 5 |
| | 4.0 | (4.48) | 5 | 4 | 5 | 5 | 5 | 5 | 3 | 5 | 5 | 5 |
| | 2.0 | (2.24) | 5 | 4 | 2 | 4 | 5 | 5 | 3 | 5 | 4 | 4 |
| | 1.0 | (1.12) | 5 | 3 | 4 | 5 | 5 | 4 | 3 | 4 | 4 | 5 |
| | 1.0 | (1.12) | 5 | 2 | 2 | 5 | 4 | 3 | 2 | 3 | 4 | 5 |
| | 0.5 | (0.56) | 5 | 2 | 2 | 4 | 3 | 4 | 4 | 3 | 4 | 4 |
| | 0.25 | (0.28) | 4 | 2 | 2 | 2 | 3 | 3 | 2 | 3 | 3 | 5 |
| 113 | 8.0 | (8.96) | 5 | 5 | 5 | 5 | 5 | 5 | 4 | 5 | 5 | 5 |
| | 4.0 | (4.48) | 5 | 4 | 5 | 5 | 5 | 5 | 3 | 5 | 5 | 5 |
| | 2.0 | (2.24) | 5 | 4 | 5 | 5 | 5 | 5 | 3 | 5 | 5 | 5 |
| | 1.0 | (1.12) | 5 | 3 | 5 | 5 | 5 | 5 | 3 | 5 | 5 | 5 |
| | 1.0 | (1.12) | 5 | 2 | 2 | 5 | 5 | 3 | 2 | 2 | 5 | 5 |
| | 0.5 | (0.56) | 5 | 2 | 3 | 5 | 4 | 3 | 3 | 2 | 5 | 5 |
| | 0.25 | (0.28) | 5 | 1 | 4 | 5 | 4 | 2 | 2 | 2 | 5 | 5 |
| 114 | 8.0 | (8.96) | 5 | 2 | 4 | 5 | 5 | 4 | 2 | 5 | 4 | 5 |
| | 4.0 | (4.48) | 4 | 1 | 2 | 5 | 5 | 2 | 2 | 3 | 3 | 4 |
| | 2.0 | (2.24) | 4 | 1 | 1 | 4 | 5 | 2 | 2 | 3 | 3 | 4 |
| | 1.0 | (1.12) | 2 | 1 | 1 | 3 | 5 | 2 | 1 | 2 | 3 | 3 |
| 115 | 1.0 | (1.12) | 5 | 3 | 5 | 5 | 5 | 5 | 4 | 5 | 4 | 5 |
| | 0.5 | (0.56) | 5 | 3 | 5 | 5 | 5 | 5 | 5 | 5 | 4 | 5 |
| | 0.25 | (2.28) | 5 | 2 | 2 | 5 | 3 | 5 | 4 | 5 | 4 | 5 |
| 116 | 1.0 | (1.12) | 5 | 4 | 5 | 5 | 5 | 5 | 4 | 5 | 5 | 5 |
| | 0.5 | (0.56) | 5 | 1 | 4 | 5 | 5 | 5 | 4 | 4 | 5 | 5 |
| | 0.25 | (0.28) | 4 | 1 | 3 | 5 | 4 | 5 | 3 | 4 | 4 | 4 |
| 117 | 1.0 | (1.12) | 5 | 4 | 5 | 5 | 5 | 5 | 4 | 5 | 3 | 5 |
| | 0.5 | (0.56) | 5 | 3 | 4 | 5 | 5 | 5 | 4 | 5 | 3 | 5 |
| | 0.25 | (2.28) | 4 | 2 | 4 | 5 | 4 | 5 | 1 | 5 | 3 | 5 |
| 118 | 8.0 | (8.96) | 5 | 3 | 5 | 5 | 5 | 4 | 4 | 5 | 4 | 5 |
| | 4.0 | (4.48) | 5 | 3 | 5 | 5 | 5 | 3 | 3 | 5 | 4 | 5 |
| | 2.0 | (2.24) | 5 | 3 | 5 | 5 | 5 | 4 | 2 | 5 | 5 | 5 |
| | 1.0 | (1.12) | 5 | 2 | 4 | 4 | 4 | 3 | 2 | 4 | 4 | 4 |

4,620,865

TABLE III-continued

Postemergence

| | | | | | | | | | | | |
|---|---|---|---|---|---|---|---|---|---|---|---|
| | 1.0 | (1.12) | 5 | 3 | 3 | 4 | 5 | 2 | 2 | 4 | 4 | 4 |
| | 0.5 | (0.56) | 3 | 1 | 3 | 3 | 4 | 2 | 2 | 3 | 3 | 4 |
| | 0.25 | (0.28) | 3 | 1 | 2 | 3 | 3 | 2 | 2 | 4 | 3 | 2 |
| 119 | 8.0 | (8.96) | 5 | 4 | 5 | 5 | 5 | 5 | 5 | 5 | 5 | 5 |
| | 4.0 | (4.48) | 5 | 4 | 5 | 5 | 5 | 5 | 3 | 5 | 5 | 5 |
| | 2.0 | (2.24) | 5 | 3 | 5 | 5 | 5 | 4 | 2 | 5 | 5 | 5 |
| | 1.0 | (1.12) | 4 | 2 | 5 | 5 | 4 | 4 | 3 | 4 | 5 | 5 |
| | 1.0 | (1.12) | 5 | 2 | 4 | 5 | 5 | 4 | 3 | 5 | 5 | 5 |
| | 0.5 | (0.56) | 5 | 1 | 4 | 5 | 4 | 3 | 2 | 5 | 4 | 5 |
| | 0.25 | (0.28) | 5 | 1 | 3 | 4 | 4 | 2 | 2 | 4 | 4 | 4 |
| | 0.25 | (0.28) | 5 | 2 | 2 | 4 | 3 | 3 | 2 | 4 | 4 | 4 |
| | 0.125 | (0.14) | 4 | 1 | 1 | 4 | 3 | 2 | 2 | 4 | 4 | 3 |
| | 0.0625 | (0.07) | 3 | 1 | 1 | 3 | 3 | 2 | 2 | 3 | 3 | 3 |
| 120 | 8.0 | (8.96) | 2 | 1 | 1 | 3 | 3 | 1 | 1 | 1 | 2 | 2 |
| 121 | 8.0 | (8.96) | 5 | 2 | 4 | 5 | 5 | 2 | 3 | 4 | 4 | 4 |
| | 4.0 | (4.48) | 4 | 2 | 3 | 1 | 5 | 3 | 2 | 3 | 3 | 3 |
| | 2.0 | (2.24) | 3 | 1 | 2 | 4 | 5 | 3 | 2 | 3 | 3 | 2 |
| | 1.0 | (1.12) | 2 | 1 | 2 | 4 | 5 | 2 | 2 | 2 | 3 | 2 |
| 122 | 8.0 | (8.96) | 4 | 1 | 2 | 5 | 5 | 2 | 2 | 3 | 4 | 3 |
| | 4.0 | (4.48) | 3 | 1 | 1 | 4 | 5 | 2 | 2 | 3 | 3 | 3 |
| | 2.0 | (2.24) | 4 | 1 | 1 | 4 | 5 | 1 | 2 | 2 | 2 | 2 |
| | 1.0 | (1.12) | 5 | 1 | 1 | 5 | 5 | 1 | 1 | 2 | 2 | 2 |
| | 1.0 | (1.12) | 1 | 1 | 1 | 3 | 4 | 1 | 1 | 1 | 2 | 2 |
| | 0.5 | (0.56) | 1 | 1 | 1 | 2 | 3 | 1 | 1 | 1 | 1 | 1 |
| | 0.25 | (0.28) | 1 | 1 | 1 | 1 | 1 | 1 | 1 | 1 | 1 | 1 |
| 123 | 8.0 | (8.96) | 5 | 3 | 2 | 5 | 5 | 4 | 2 | 5 | 4 | 5 |
| | 4.0 | (4.48) | 5 | 2 | 4 | 5 | 5 | 4 | 2 | 5 | 4 | 5 |
| | 2.0 | (2.24) | 5 | 1 | 3 | 5 | 5 | 4 | 2 | 5 | 4 | 5 |
| | 1.0 | (1.12) | 4 | 1 | 1 | 3 | 5 | 2 | 2 | 4 | 4 | 4 |
| | 1.0 | (1.12) | 5 | 1 | 3 | 4 | 5 | 2 | 2 | 4 | 3 | 4 |
| | 0.5 | (0.56) | 4 | 1 | 2 | 3 | 4 | 2 | 2 | 3 | 3 | 3 |
| | 0.25 | (0.28) | 3 | 1 | 1 | 4 | 4 | 2 | 1 | 3 | 2 | 2 |
| 124 | 8.0 | (8.96) | 5 | 1 | 1 | 4 | 5 | 2 | 2 | 4 | 4 | 4 |
| | 4.0 | (4.48) | 4 | 1 | 3 | 5 | 5 | 4 | 2 | 4 | 4 | 4 |
| | 2.0 | (2.24) | 4 | 1 | 2 | 4 | 5 | 3 | 2 | 4 | 3 | 4 |
| | 1.0 | (1.12) | 3 | 1 | 1 | 3 | 4 | 2 | 1 | 3 | 4 | 3 |
| 125 | 8.0 | (8.96) | 5 | 4 | 5 | 5 | 5 | 5 | 4 | 5 | 5 | 5 |
| | 4.0 | (4.48) | 5 | 3 | 4 | 5 | 5 | 4 | 3 | 4 | 4 | 5 |
| | 2.0 | (2.24) | 5 | 3 | 3 | 5 | 5 | 4 | 3 | 4 | 4 | 5 |
| | 1.0 | (1.12) | 4 | 2 | 3 | 5 | 5 | 3 | 2 | 4 | 4 | 4 |
| | 1.0 | (1.12) | 4 | 2 | 2 | 5 | 4 | 3 | 2 | 3 | 3 | 4 |
| | 0.5 | (0.56) | 3 | 1 | 1 | 3 | 4 | 2 | 2 | 3 | 3 | |
| | 0.25 | (0.28) | 1 | 1 | 1 | 3 | 4 | 1 | 1 | 1 | 2 | 2 |
| 126 | 8.0 | (8.96) | 5 | 3 | 4 | 5 | 5 | 4 | 4 | 4 | 4 | 5 |
| | 4.0 | (4.48) | 4 | 2 | 2 | 5 | 5 | 3 | 2 | 3 | 3 | 4 |
| | 2.0 | (2.24) | 3 | 1 | 2 | 5 | 5 | 3 | 1 | 3 | 2 | 3 |
| | 1.0 | (1.12) | 2 | 1 | 1 | 3 | 5 | 2 | 1 | 2 | 2 | 2 |
| 127 | 8.0 | (8.96) | 3 | 1 | 1 | 4 | 4 | 1 | 1 | 1 | 3 | 3 |
| | 4.0 | (4.48) | 2 | 1 | 1 | 3 | 2 | 1 | 2 | 1 | 2 | 2 |
| | 2.0 | (2.24) | 1 | 1 | 1 | 2 | 2 | 1 | 1 | 1 | 1 | 2 |
| | 1.0 | (1.12) | 1 | 1 | 1 | 2 | 1 | 1 | 1 | 1 | 1 | 2 |
| 128 | 8.0 | (8.96) | 5 | 4 | 5 | 5 | 5 | 5 | 4 | 4 | 4 | 5 |
| | 4.0 | (4.48) | 5 | 2 | 4 | 5 | 5 | 3 | 4 | 4 | 4 | 4 |
| | 2.0 | (2.24) | 5 | 1 | 4 | 5 | 5 | 3 | 3 | 3 | 3 | 3 |
| | 1.0 | (1.12) | 3 | 1 | 2 | 4 | 5 | 2 | 1 | 2 | 2 | 3 |
| 129 | 8.0 | (8.96) | 1 | 1 | 1 | 2 | 1 | 1 | 1 | 2 | 2 | 1 |
| 136 | 1.0 | (1.12) | 4 | 5 | 4 | 5 | 4 | 5 | 3 | 3 | 5 | 5 |
| | 0.5 | (0.56) | 4 | 4 | 4 | 5 | 4 | 5 | 3 | 3 | 5 | 5 |
| | 0.25 | (0.28) | 4 | 2 | 4 | 5 | 5 | 5 | 2 | 3 | 5 | 5 |
| 140 | 8.0 | (8.96) | 4 | 5 | 4 | 5 | 5 | 4 | 2 | 4 | 4 | 5 |
| | 4.0 | (4.48) | 2 | 2 | 2 | 4 | 5 | 2 | 2 | 1 | 3 | 5 |
| | 2.0 | (2.24) | 1 | 2 | 2 | 3 | 5 | 4 | 2 | 1 | 4 | 5 |
| | 1.0 | (1.12) | 1 | 2 | 1 | 2 | 5 | 2 | 2 | 2 | 2 | 4 |
| 141 | 8.0 | (8.96) | 5 | 4 | 4 | 5 | 5 | 4 | 2 | 4 | 4 | 5 |
| | 4.0 | (4.48) | 5 | 2 | 3 | 5 | 5 | 3 | 1 | 2 | 4 | 5 |
| | 2.0 | (2.24) | 4 | 1 | 3 | 3 | 5 | 2 | 1 | 1 | 3 | 5 |
| | 1.0 | (1.12) | 4 | 2 | 3 | 5 | | 3 | 1 | 1 | 2 | 5 |
| 142 | 8.0 | (8.96) | 5 | 3 | 4 | 4 | 5 | 5 | 2 | 5 | 4 | 5 |
| | 4.0 | (4.48) | 5 | 3 | 3 | 5 | | 4 | 1 | 3 | 3 | 5 |
| | 2.0 | (2.24) | 4 | 2 | 3 | 4 | | 3 | 2 | 2 | 4 | 5 |
| | 1.0 | (1.12) | 3 | 2 | 2 | 3 | | 4 | 1 | 2 | 3 | 4 |
| 143 | 8.0 | (8.96) | 5 | 2 | 4 | 5 | 5 | 4 | 2 | 4 | 4 | 5 |
| | 4.0 | (4.48) | 3 | 2 | 3 | 4 | | 4 | 1 | 4 | 3 | 5 |
| | 2.0 | (2.24) | 5 | 2 | 3 | 5 | | 3 | 2 | 4 | 2 | 4 |
| | 1.0 | (1.12) | 2 | 2 | 2 | 3 | | 2 | 1 | 2 | 2 | 2 |
| 144 | 8.0 | (8.96) | 4 | 4 | 4 | 5 | 4 | 4 | 4 | 5 | 3 | 5 |
| | 4.0 | (4.48) | 1 | 1 | 1 | 3 | 5 | 1 | 2 | 1 | 2 | 3 |
| | 2.0 | (2.24) | 1 | 1 | 1 | 3 | 5 | 1 | 1 | 1 | 1 | 1 |
| | 1.0 | (1.12) | 1 | 1 | 1 | 3 | 4 | 1 | 1 | 1 | 1 | 1 |
| 145 | 8.0 | (8.96) | 4 | 2 | 4 | 5 | 5 | 3 | 2 | 2 | 3 | 4 |
| | 4.0 | (4.48) | 3 | 2 | 2 | 4 | 4 | 3 | 2 | 2 | 3 | 3 |

TABLE III-continued

Postemergence

| | | | | | | | | | | | |
|---|---|---|---|---|---|---|---|---|---|---|---|
| | 2.0 | (2.24) | 2 | 2 | 2 | 2 | 3 | 1 | 1 | 1 | 2 | 2 |
| | 1.0 | (1.12) | 2 | 1 | 2 | 4 | 4 | 1 | 1 | 1 | 3 | 3 |
| 146 | 8.0 | (8.96) | 5 | 4 | 5 | 5 | 5 | 5 | 4 | 4 | 5 | 5 |
| | 4.0 | (4.48) | 5 | 3 | 4 | 5 | 5 | 3 | 2 | 4 | 5 | 5 |
| | 2.0 | (2.24) | 5 | 3 | 4 | 5 | 5 | 3 | 2 | 4 | 5 | 5 |
| | 1.0 | (1.12) | 5 | 2 | 4 | 5 | 5 | 3 | 2 | 4 | 5 | 5 |
| | 1.0 | (1.12) | 4 | 2 | 2 | 4 | 5 | 3 | 1 | 1 | 4 | 4 |
| | 0.5 | (0.56) | 3 | 1 | 2 | 4 | 5 | 2 | 2 | 2 | 4 | 5 |
| | 0.25 | (0.28) | 3 | 1 | 2 | 2 | 5 | 1 | 2 | 1 | 3 | 2 |
| 147 | 8.0 | (8.96) | 3 | 1 | 3 | 4 | 4 | 1 | 2 | 3 | 3 | 2 |
| | 4.0 | (4.48) | 1 | 1 | 1 | 2 | 3 | 1 | 1 | 1 | 2 | 1 |
| | 2.0 | (2.24) | 1 | 1 | 1 | 2 | 3 | 1 | 1 | 1 | 2 | 1 |
| | 1.0 | (1.12) | 1 | 1 | 1 | 1 | 2 | 1 | 1 | 1 | 1 | 1 |
| 148 | 8.0 | (8.96) | 2 | 1 | 4 | 4 | 4 | 3 | 3 | 3 | 2 | 4 |
| | 4.0 | (4.48) | 1 | 1 | 2 | 3 | 4 | 2 | 1 | 1 | 1 | 2 |
| | 2.0 | (2.24) | 1 | 1 | 2 | 2 | 4 | 2 | 1 | 1 | 1 | 1 |
| | 1.0 | (1.12) | 1 | 1 | 1 | 2 | 3 | 1 | 1 | 1 | 1 | 1 |
| 149 | 8.0 | (8.96) | 5 | 2 | 2 | 5 | 5 | 3 | 3 | 5 | 4 | 5 |
| | 4.0 | (4.48) | 5 | 4 | 3 | 5 | 5 | 5 | 4 | 5 | 5 | 5 |
| | 2.0 | (2.24) | 5 | 3 | 2 | 5 | 5 | 3 | 4 | 5 | 4 | 5 |
| | 1.0 | (1.12) | 5 | 1 | 2 | 3 | 4 | 3 | 3 | 5 | 4 | 3 |
| 150 | 8.0 | (8.96) | 5 | 4 | 3 | 5 | 5 | 4 | 5 | 5 | 5 | 5 |
| | 4.0 | (4.48) | 5 | 5 | 5 | 5 | 5 | 5 | 5 | 5 | 5 | 5 |
| | 2.0 | (2.24) | 5 | 4 | 5 | 5 | 5 | 5 | 5 | 5 | 5 | 5 |
| | 1.0 | (1.12) | 5 | 3 | 3 | 5 | 5 | 5 | 4 | 5 | 4 | 5 |
| 151 | 8.0 | (8.96) | 4 | 3 | 4 | 4 | 5 | 3 | 4 | 5 | 4 | 3 |
| | 4.0 | (4.48) | 3 | 2 | 3 | 4 | 5 | 2 | 3 | 3 | 4 | 3 |
| | 2.0 | (2.24) | 2 | 1 | 1 | 3 | 4 | 2 | 2 | 3 | 3 | 3 |
| | 1.0 | (1.12) | 1 | 1 | 1 | 1 | 4 | 2 | 2 | 1 | 2 | 2 |
| 154 | 8.0 | (8.96) | 1 | 1 | 1 | 3 | 3 | 2 | 3 | 1 | 1 | 1 |
| 156 | 8.0 | (8.96) | 4 | 1 | 1 | 4 | 4 | 2 | 1 | 4 | 3 | 3 |
| | 4.0 | (4.48) | 2 | 1 | 1 | 3 | 4 | 2 | 2 | 3 | 3 | 3 |
| | 2.0 | (2.24) | 2 | 1 | 1 | 2 | 2 | 2 | 1 | 1 | 2 | 2 |
| | 1.0 | (1.12) | 1 | 1 | 1 | 2 | 1 | 1 | 1 | 1 | 2 | 2 |
| 157 | 8.0 | (8.96) | 5 | 4 | 4 | 5 | 5 | 4 | 3 | 5 | 4 | 5 |
| | 4.0 | (4.48) | 5 | 2 | 4 | 5 | 5 | 4 | 3 | 4 | 3 | 4 |
| | 2.0 | (2.24) | 4 | 1 | 2 | 5 | 4 | 3 | 2 | 4 | 3 | 4 |
| | 1.0 | (1.12) | 3 | 1 | 1 | 4 | 4 | 2 | 1 | 3 | 3 | 3 |
| 157 | 1.0 | (1.12) | 2 | 1 | 3 | 3 | 3 | 2 | 2 | 3 | 2 | 3 |
| | 0.5 | (0.56) | 2 | 1 | 2 | 3 | 3 | 2 | 2 | 2 | 2 | 3 |
| | 0.25 | (0.28) | 2 | 1 | 2 | 3 | 2 | 1 | 1 | 2 | 2 | 3 |

Five compounds of the present invention were in various field studies in an effort to further evaluate the compound's herbicidal activity and crop tolerance. Compounds of example numbers 31, 47 and 55 were individually formulated as a 50% wettable powder which contained the following percentages and ingredients by weight:

| | |
|---|---|
| 51.5 | Active agent |
| 5.0 | Sellogen HR, a wetting agent from Diamond Shamrock Corp. |
| 5.0 | Zeolex 7, a hydrated silicate from J.M. Huber Corp. |
| 5.0 | Polyfon O, a dispersant from Westvaco Corp., Polychemicals Dept. |
| 33.5 | Barden, a hydrated aluminum silicate from J.M. Huber Corp. |
| 100.0 | |

Compounds of example numbers 1 and 3 were also formulated as a 50% wettable powder which contained the following percentages and ingredients by weight:.

| | |
|---|---|
| 51.5 | Active agent |
| 5.0 | Stepanol ME, Sodium lauryl sulfate from Stepanol Chemical Co. |
| 5.0 | Zeolex 7, a hydrated silicate from J.M. Huber Corp. |
| 5.0 | Polyfon O, a dispersant from Westvaco Corp., Polychemicals Dept. |
| 33.5 | Barden, a hydrated aluminum silicate from J M. Huber Corp. |
| 100.0 | |

EXPERIMENT 3

The compound identified as Example 55 of the present invention was tested in a field study according to the following procedure. The compound was formulated as a 50% wettable powder as described above and diluted with water to provide the desired concentration of the active agent. The compound was then surface applied preemergence to wheat and barley at various application rates. Observations were made at 21 and 37 days after planting (and treatment) and visually compared to control plots. The results of the field test are reported below in Table IV as precent inhibition.

TABLE IV

| | | Surface Applied | | | | |
|---|---|---|---|---|---|---|
| Appln. rate | Days After | Crops | | Weeds | | |
| lbs/acre (kg/ha) | Treatment | Barley | Wheat | Redroot Pigweed | Indian Mustard | Green Foxtail |
| 4.0 (4.48) | 21 | 21.7 | 10.0 | 100.0 | 96.7 | 100.0 |
| 2.0 (2.24) | | 16.7 | 6.7 | 96.7 | 88.3 | 89.3 |
| 1.0 (1.12) | | 0 | 0 | 72.7 | 56.7 | 36.7 |
| 0.5 (0.56) | | 0 | 0 | 0 | 0 | 0 |
| 4.0 (4.48) | 37 | 6.7 | 5.0 | 100.0 | 100.0 | 100.0 |
| 2.0 (2.24) | | 0 | 3.3 | 91.7 | 90.0 | 90.0 |
| 1.0 (1.12) | | 0 | 3.3 | 65.0 | 56.7 | 23.3 |

TABLE IV-continued

| | | Surface Applied | | | | |
|---|---|---|---|---|---|---|
| Appln. rate lbs/acre (kg/ha) | Days After Treatment | Crops | | Weeds | | |
| | | Barley | Wheat | Redroot Pigweed | Indian Mustard | Green Foxtail |
| 0.5 (0.56) | | 0 | 0 | 0 | 16.7 | 0 |

EXPERIMENT 4

Examples 1, 3, 31 and 47 of the present invention were also tested in a field study to evaluate the compounds' herbicidal activity and crop tolerance. Each compound was formulated as a 50% wettable powder as described above.

The formulated compounds diluted with water were both surface applied and pre-plant incorporated at various application rates to assorted crop and weed species. Crop injury ratings were made visually on a scale of 0–10, with 0 being no injury and 10 being plant death, and this number was multiplied by 10 to obtain a percent inhibition. Three replications were done at each rate and the average percent inhibition entered in the table. Observations were made at 3 and 6 weeks after planting (and treatment). The results of the field test were reported below in Table V (surface applied) and Table VI (pre-plant incorporated).

TABLE V

Surface Applied

| Example No. of Compound Tested | Appln. rate lbs/acre (kg/ha) | Weeks after planting | Crops | | | | | | Weeds | | | | | | |
|---|---|---|---|---|---|---|---|---|---|---|---|---|---|---|---|
| | | | Sorghum | Field Corn | Barley | Wheat | Soybean | Cotton | Redroot Pigweed | Morning glory | Wild Mustard | Wild Oat | Green Foxtail | Ragweed | Foxtail Millet |
| 1 | 4.0 (4.48) | 3 | 0 | 0 | 33.3 | 10.0 | 40.0 | 60.0 | 100.0 | 24.2 | 98.3 | 20.0 | 91.7 | | 71.1 |
| | | 6 | 0 | 0 | 26.7 | 6.7 | 56.7 | 55.0 | 100.0 | 10.9 | 100.0 | 6.7 | 81.7 | 93.9 | 78.3 |
| | 2.0 (2.24) | 3 | 0 | 0 | 21.7 | 6.7 | 16.7 | 35.0 | 100.0 | 16.7 | 80.0 | 21.7 | 61.7 | | 31.7 |
| | | 6 | 0 | 0 | 23.3 | 0 | 18.3 | 18.3 | 89.2 | 13.4 | 83.3 | 3.3 | 26.7 | 55.0 | 35.8 |
| | 1.0 (1.12) | 3 | 0 | 0 | 6.7 | 3.3 | 3.3 | 16.7 | 80.0 | 5.0 | 60.0 | 6.7 | 30.0 | | 10.8 |
| | | 6 | 0 | 0 | 0 | 0 | 0 | 0 | 64.7 | 6.7 | 53.3 | 0 | 6.7 | 10.0 | 16.7 |
| | 0.5 (0.56) | 3 | 0 | 0 | 6.7 | 3.3 | 8.3 | 20.0 | 23.3 | 10.0 | 40.0 | 13.3 | 6.7 | | 10.0 |
| | | 6 | 0 | 0 | 0 | 0 | 6.7 | 5.0 | 0 | 0 | 10.0 | 0 | 0 | 6.7 | 10.0 |
| 3 | 4.0 (4.48) | 3 | 0 | 1.3 | 50.0 | 20.0 | 58.3 | 56.7 | 100.0 | 35.9 | 100.0 | 36.7 | 93.3 | | 63.3 |
| | | 6 | 0 | 0 | 53.3 | 23.3 | 56.7 | 40.0 | 81.9 | 6.7 | 98.3 | 33.3 | 75.0 | 69.2 | 66.7 |
| | 2.0 (2.24) | 3 | 0 | 0 | 16.7 | 0 | 10.0 | 23.3 | 93.3 | 12.5 | 91.7 | 10.0 | 91.7 | | 36.7 |
| | | 6 | 0 | 0 | 15.0 | 3.3 | 0 | 6.7 | 68.4 | 7.5 | 83.3 | 0 | 70.0 | 35.0 | 36.7 |
| | 1.0 (1.12) | 3 | 0 | 0 | 0 | 0 | 23.3 | 26.7 | 46.7 | 15.0 | 60.0 | 3.3 | 6.7 | | 31.7 |
| | | 6 | 0 | 0 | 0 | 0 | 21.7 | 16.7 | 40.0 | 0 | 50.0 | 0 | 0 | 40.9 | 35.9 |
| | 0.5 (0.56) | 3 | 0 | 0 | 0 | 0 | 0 | 3.3 | 0 | 0 | 36.7 | 3.3 | 16.7 | | 5.0 |
| | | 6 | 0 | 0 | 0 | 0 | 0 | 0 | 0 | 0 | 0 | 0 | 0 | 15.0 | 9.2 |
| 31 | 4.0 (4.48) | 3 | 16.7 | 0 | 33.3 | 3.3 | 76.7 | 87.7 | 96.7 | 55.8 | 81.7 | 10.0 | 88.0 | | 82.0 |
| | | 6 | 0 | 0 | 23.3 | 3.3 | 94.3 | 99.3 | 92.9 | 39.2 | 90.0 | 3.3 | 70.0 | 95.9 | 85.9 |
| | 2.0 (2.24) | 3 | 0 | 0 | 43.3 | 6.7 | 23.3 | 46.7 | 96.7 | 38.4 | 91.7 | 23.3 | 85.0 | | 68.4 |
| | | 6 | 0 | 0 | 40.0 | 10.0 | 15.0 | 45.0 | 76.7 | 27.5 | 90.0 | 13.3 | 73.3 | 74.2 | 67.5 |
| | 1.0 (1.12) | 3 | 0 | 0 | 13.3 | 6.7 | 30.0 | 40.0 | 56.7 | 26.7 | 73.3 | 6.7 | 30.0 | | 27.5 |
| | | 6 | 0 | 0 | 3.3 | 6.7 | 25.0 | 23.3 | 35.9 | 28.3 | 70.0 | 3.3 | 3.3 | 53.4 | 15.9 |
| | 0.5 (0.56) | 3 | 0 | 0 | 6.7 | 0 | 3.3 | 6.7 | 26.7 | 0 | 50.0 | 20.0 | 33.3 | | 0 |
| | | 6 | 0 | 0 | 0 | 0 | 0 | 0 | 28.4 | 12.5 | 23.3 | 0 | 0 | 8.4 | 0 |
| 47 | 4.0 (4.48) | 3 | 6.7 | 0 | 88.3 | 45.0 | 63.3 | 80.0 | 100.0 | 27.5 | 100.0 | 75.0 | 98.3 | | 83.0 |
| | | 6 | 0 | 0 | 89.3 | 53.0 | 78.3 | 81.0 | 98.4 | 8.4 | 100.0 | 63.3 | 91.7 | 96.7 | 84.0 |
| | 2.0 (2.24) | 3 | 0 | 0 | 35.0 | 6.7 | 38.3 | 46.7 | 100.0 | 21.7 | 95.0 | 23.3 | 96.7 | | 49.2 |
| | | 6 | 0 | 0 | 31.7 | 0 | 41.7 | 31.7 | 100.0 | 6.7 | 93.3 | 10.0 | 83.3 | 86.7 | 57.5 |
| | 1.0 (1.12) | 3 | 0 | 0 | 0 | 0 | 16.7 | 16.7 | 86.7 | 13.4 | 76.1 | 13.3 | 50.0 | | 26.7 |
| | | 6 | 0 | 0 | 0 | 0 | 0 | 3.3 | 43.4 | 0 | 46.7 | 0 | 16.7 | 40.9 | 11.7 |
| | 0.5 (0.56) | 3 | 0 | 0 | 10.0 | 3.3 | 6.7 | 0 | 66.7 | 5.0 | 50.0 | 6.7 | 36.7 | | 6.7 |
| | | 6 | 0 | 0 | 0 | 0 | 0 | 0 | 28.4 | 0 | 26.7 | 0 | 20.0 | 12.5 | 0 |

TABLE VI

Pre-Plant Incorporated

| Example No. of Compound Tested | Appln. rate lbs/acre (kg/ha) | Weeks after planting | Crops | | | | | | Weeds | | | | | |
|---|---|---|---|---|---|---|---|---|---|---|---|---|---|---|
| | | | Sorghum | Field Corn | Barley | Wheat | Soybean | Cotton | Redroot Pigweed | Morning glory | Wild Mustard | Wild Oat | Green Foxtail | Foxtail Millet |
| 1 | 4.0 (4.48) | 3 | 30.0 | 6.7 | 76.7 | 71.7 | 65.0 | 56.7 | 100.0 | 44.4 | 100.0 | 53.3 | 71.7 | 56.7 |
| | | 6 | 0 | 0 | 81.7 | 75.0 | 66.7 | 50.0 | 45.6 | 68.3 | 100.0 | 53.3 | 53.3 | 54.2 |
| | 2.0 (2.24) | 3 | 13.3 | 0 | 33.3 | 35.0 | 13.3 | 18.3 | 81.7 | 23.4 | 86.7 | 28.3 | 46.7 | 33.3 |
| | | 6 | 0 | 0 | 18.3 | 11.7 | 25.0 | 25.0 | 84.5 | 71.7 | 93.3 | 13.3 | 6.7 | 28.4 |
| | 1.0 (1.12) | 3 | 0 | 0 | 0 | 0 | 0 | 0 | 35.0 | 0 | 50.0 | 0 | 13.3 | 0 |
| | | 6 | 0 | 0 | 0 | 0 | 3.3 | 6.7 | 62.2 | 45.0 | 50.0 | 0 | 0 | 3.4 |
| | 0.5 (0.56) | 3 | 0 | 0 | 3.3 | 3.3 | 0 | 0 | 43.3 | 0 | 26.7 | 10.0 | 10.0 | 0 |
| | | 6 | 0 | 0 | 0 | 0 | 0 | 3.3 | 10.0 | 0 | 16.7 | 0 | 0 | 0 |
| 3 | 4.0 (4.48) | 3 | 10.0 | 0 | 58.0 | 43.3 | 10.0 | 5.0 | 78.4 | 15.0 | 90.0 | 46.7 | 85.0 | 43.3 |
| | | 6 | 6.7 | 6.7 | 53.3 | 40.0 | 6.7 | 20.0 | 90.7 | 41.7 | 96.7 | 36.7 | 56.7 | 52.4 |
| | 2.0 (2.24) | 3 | 6.7 | 0 | 33.3 | 3.3 | 0 | 0 | 50.9 | 0 | 78.3 | 23.3 | 63.3 | 0 |
| | | 6 | 10.0 | 0 | 30.0 | 3.3 | 0 | 10.0 | 34.4 | 0 | 83.3 | 6.7 | 10.0 | 6.7 |
| | 1.0 (1.12) | 3 | 0 | 0 | 0 | 0 | 0 | 0 | 8.4 | 8.4 | 53.3 | 0 | 30.0 | 0 |
| | | 6 | 0 | 0 | 0 | 0 | 0 | 0 | 5.6 | 20.0 | 36.7 | 0 | 3.3 | 3.4 |

TABLE VI-continued

Pre-Plant Incorporated

| Example No. of Compound Tested | Appln. rate lbs/acre (kg/ha) | | Weeks after planting | Crops | | | | | | Weeds | | | | | |
|---|---|---|---|---|---|---|---|---|---|---|---|---|---|---|---|
| | | | | Sorghum | Field Corn | Barley | Wheat | Soybean | Cotton | Redroot Pigweed | Morning glory | Wild Mustard | Wild Oat | Green Foxtail | Foxtail Millet |
| | 0.50 | (0.56) | 3 | 0 | 0 | 0 | 0 | 0 | 0 | 10.0 | 0 | 10.0 | 0 | 13.3 | 0 |
| | | | 6 | 0 | 0 | 0 | 0 | 0 | 5.0 | 3.3 | 21.7 | 0 | 0 | 0 | 0 |
| 31 | 4.0 | (4.48) | 3 | 46.7 | 10.0 | 85.0 | 66.7 | 70.0 | 55.0 | 97.7 | 40.0 | 100.0 | 80.0 | 96.0 | 63.3 |
| | | | 6 | 25.0 | 5.0 | 86.7 | 70.0 | 68.3 | 55.0 | 91.6 | 61.7 | 96.7 | 78.3 | 83.3 | 50.0 |
| | 2.0 | (2.24) | 3 | 16.7 | 3.3 | 40.0 | 23.3 | 11.7 | 3.3 | 66.7 | 13.4 | 98.3 | 40.0 | 73.3 | 30.0 |
| | | | 6 | 3.3 | 0 | 23.3 | 6.7 | 30.0 | 23.3 | 84.2 | 38.4 | 91.7 | 30.0 | 46.7 | 37.5 |
| | 1.0 | (1.12) | 3 | 0 | 0 | 13.3 | 3.3 | 0 | 0 | 45.9 | 5.0 | 93.3 | 16.7 | 43.3 | 23.3 |
| | | | 6 | 0 | 0 | 6.7 | 0 | 0 | 0 | 43.3 | 16.7 | 73.7 | 10.0 | 0 | 3.4 |
| | 0.50 | (0.56) | 3 | 0 | 0 | 10.0 | 0 | 0 | 1.7 | 35.0 | 3.4 | 61.7 | 10.0 | 30.0 | 6.7 |
| | | | 6 | 0 | 0 | 0 | 0 | 0 | 0 | 20.0 | 8.3 | 30.0 | 0 | 0 | 0 |
| 47 | 4.0 | (4.48) | 3 | 26.7 | 16.7 | 70.0 | 66.7 | 65.0 | 33.3 | 99.7 | 23.4 | 100.0 | 70.0 | 99.3 | 53.3 |
| | | | 6 | 6.7 | 0 | 71.7 | 81.7 | 68.3 | 35.0 | 96.7 | 40.0 | 99.3 | 70.0 | 90.0 | 65.8 |
| | 2.0 | (2.24) | 3 | 36.7 | 0 | 53.3 | 40.0 | 18.3 | 21.7 | 96.7 | 18.4 | 100.0 | 56.7 | 56.7 | 10.0 |
| | | | 6 | 13.3 | 0 | 60.0 | 36.7 | 28.3 | 25.0 | 90.7 | 35.0 | 99.3 | 50.0 | 16.7 | 23.4 |
| | 1.0 | (1.12) | 3 | 10.0 | 0 | 16.7 | 13.3 | 0 | 0 | 48.4 | 11.7 | 86.7 | 13.3 | 33.0 | 23.3 |
| | | | 6 | 0 | 0 | 0 | 5.0 | 3.3 | 6.7 | 63.1 | 48.3 | 83.3 | 10.0 | 0 | 17.5 |
| | 0.50 | (0.56) | 3 | 0 | 0 | 0 | 0 | 0 | 0 | 43.4 | 0 | 63.3 | 6.7 | 16.7 | 0 |
| | | | 6 | 0 | 0 | 0 | 0 | 0 | 0 | 31.1 | 10.0 | 70.0 | 0 | 0 | 0 |

EXPERIMENT 5

A field study was also conducted in Great Britain to determine the efficacy and selectivity of certain compounds of the invention when applied preemergence to cereal grains and weeds contained therein. The compounds were formulated as aqueous suspensions by mixing the active agent with the sodium salt of dibutylnaphthalene sulphonate to otain a formulation containing the active agent at a concentration of 2 percent by weight upon dilution with water.

The formulated compounds were diluted with water and applied preemergence on the same day the crops were planted. Observations were made at various intervals thereafter to determine the compounds' effect against the crop species barley and wheat as compared to untreated control plots, as well as the compounds' ability to control certain weed species. Control ratings are given in percentage of control as compared to untreated control plots based upon visual inspection. These results appear below in Table VII as the average of four replicates.

TABLE VII

Preemergence

| Example No. of Compound Tested | Observation | Days After Treatment | Rate kg/ha | Percent |
|---|---|---|---|---|
| 1 | Barley Emergence | 18 | 1.0 | 153.3 |
| | | | 0.75 | 187.4 |
| | | | 0.50 | 145.4 |
| | | | 0.25 | 145.5 |
| | | | Untreated Control | 100.0 |
| | Barley Vigor | 25 | 1.0 | 98.9 |
| | | | 0.75 | 97.8 |
| | | | 0.50 | 100.0 |
| | | | 0.25 | 99.4 |
| | | | Untreated Control | 100.0 |
| | Wheat Emergence | 18 | 1.0 | 93.6 |
| | | | 0.75 | 72.1 |
| | | | 0.50 | 88.9 |
| | | | 0.25 | 92.6 |
| | | | Untreated Control | 100.0 |
| | Wheat Vigor | 25 | 1.0 | 99.4 |
| | | | 0.75 | 98.8 |

TABLE VII-continued

Preemergence

| Example No. of Compound Tested | Observation | Days After Treatment | Rate kg/ha | Percent |
|---|---|---|---|---|
| | | | 0.50 | 100.6 |
| | | | 0.25 | 101.2 |
| | | | Untreated Control | 100.0 |
| | Control of Wild Oat | 34 | 1.0 | 1.2 |
| | | | 0.75 | 1.8 |
| | | | 0.50 | 2.3 |
| | | | 0.25 | 0 |
| | | | Untreated Control | 0 |
| | Control of Catchweed Bedstraw | 34 | 1.0 | 0 |
| | | | 0.75 | 2.3 |
| | | | 0.50 | 0 |
| | | | 0.25 | 3.3 |
| | | | Untreated Control | 0 |
| | Control of Scentless Mayweed | 34 | 1.0 | 68.5 |
| | | | 0.75 | 62.5 |
| | | | 0.5 | 73.5 |
| | | | 0.25 | 37.5 |
| | | | Untreated Control | 0 |
| | Control of Annual Bluegrass | 34 | 1.0 | 15.8 |
| | | | 0.75 | 13.3 |
| | | | 0.5 | 3.3 |
| | | | 0.25 | 1.8 |
| | | | Untreated Control | 0 |
| | Control of Ladysthumb | 34 | 1.0 | 55.4 |
| | | | 0.75 | 1.8 |
| | | | 0.5 | 4.7 |
| | | | 0.25 | 0 |
| | | | Untreated Control | 0 |
| | Control of Chickweed | 34 | 1.0 | 31.5 |
| | | | 0.75 | 18.8 |
| | | | 0.5 | 13.3 |
| | | | 0.25 | 7.9 |
| | | | Untreated Control | 0 |
| | Control of Ivyleaf Speedwell | 34 | 1.0 | 0 |
| | | | 0.75 | 0 |
| | | | 0.5 | 3.9 |
| | | | 0.25 | 7.9 |
| | | | Untreated Control | 0 |
| | Control of | 34 | 1.0 | 1.8 |

TABLE VII-continued

Preemergence

| Example No. of Compound Tested | Observation | Days After Treatment | Rate kg/ha | Percent |
|---|---|---|---|---|
| | Wild Violet | | 0.75 | 0.6 |
| | | | 0.5 | 9.4 |
| | | | 0.25 | 3.3 |
| | | | Untreated Control | 0 |
| 3 | Barley Emergence | 18 | 2.0 | 152.1 |
| | | | 1.5 | 129.7 |
| | | | 1.0 | 129.9 |
| | | | 0.5 | 132.3 |
| | | | Untreated Control | 100.0 |
| | Barley Vigor | 25 | 2.0 | 100.6 |
| | | | 1.5 | 100.0 |
| | | | 1.0 | 98.9 |
| | | | 0.5 | 97.8 |
| | | | Untreated Control | 100.0 |
| | Wheat Emergence | 18 | 2.0 | 67.0 |
| | | | 1.5 | 58.4 |
| | | | 1.0 | 73.9 |
| | | | 0.5 | 85.2 |
| | | | Untreated Control | 100.0 |
| | Wheat Vigor | 25 | 2.0 | 98.8 |
| | | | 1.5 | 98.8 |
| | | | 1.0 | 100.0 |
| | | | 0.5 | 99.4 |
| | | | Untreated Control | 100.0 |
| | Control of Wild Oat | 34 | 2.0 | 11.1 |
| | | | 1.5 | 3.3 |
| | | | 1.0 | 2.3 |
| | | | 0.5 | 1.2 |
| | | | Untreated Control | 0 |
| | Control of Catchweed Bedstraw | 34 | 2.0 | 13.3 |
| | | | 1.5 | 0 |
| | | | 1.0 | 3.9 |
| | | | 0.5 | 0 |
| | | | Untreated Control | 0 |
| | Control of Scentless Mayweed | 34 | 2.0 | 96.7 |
| | | | 1.5 | 92.1 |
| | | | 1.0 | 86.7 |
| | | | 0.5 | 73.5 |
| | | | Untreated Control | 0 |
| | Control of Annual Bluegrass | 34 | 2.0 | 95.3 |
| | | | 1.5 | 90.6 |
| | | | 1.0 | 62.5 |
| | | | 0.5 | 3.9 |
| | | | Untreated Control | 0 |
| | Control of Ladysthumb | 34 | 2.0 | 84.2 |
| | | | 1.5 | 11.1 |
| | | | 1.0 | 77.7 |
| | | | 0.5 | 13.3 |
| | | | Untreated Control | 0 |
| | Control of Chickweed | 34 | 2.0 | 88.8 |
| | | | 1.5 | 31.5 |
| | | | 1.0 | 13.3 |
| | | | 0.5 | 2.8 |
| | | | Untreated Control | 0 |
| | Control of Ivyleaf Speedwell | 34 | 2.0 | 0 |
| | | | 1.5 | 0 |
| | | | 1.0 | 0 |
| | | | 0.5 | 0 |
| | | | Untreated Control | 0 |
| | Control of Wild Violet | 34 | 2.0 | 92.1 |
| | | | 1.5 | 44.6 |
| | | | 1.0 | 26.5 |
| | | | 0.5 | 3.3 |
| | | | Untreated | 0 |
| 47 | Barley Emergence | 18 | 2.0 | 93.3 |
| | | | 1.0 | 103.2 |
| | | | 0.5 | 70.1 |
| | | | 0.25 | 89.1 |
| | | | Untreated Control | 100.0 |
| | Barley Vigor | 25 | 2.0 | 97.0 |
| | | | 1.0 | 100.0 |
| | | | 0.5 | 100.0 |
| | | | 0.25 | 100.6 |
| | | | Untreated Control | 100.0 |
| | Wheat Emergence | 18 | 2.0 | 68.3 |
| | | | 1.0 | 96.0 |
| | | | 0.5 | 69.1 |
| | | | Untreated Control | 100.0 |
| | Wheat Vigor | 25 | 2.0 | 97.8 |
| | | | 1.0 | 98.8 |
| | | | 0.5 | 99.4 |
| | | | 0.25 | 98.4 |
| | | | Untreated Control | 100.0 |
| | Control of Wild Oat | 34 | 2.0 | 55.4 |
| | | | 1.0 | 3.3 |
| | | | 0.5 | 1.2 |
| | | | 0.25 | 13.3 |
| | | | Untreated Control | 0 |
| | Control of Catchweed Bedstraw | 34 | 2.0 | 13.3 |
| | | | 1.0 | 1.8 |
| | | | 0.5 | 3.3 |
| | | | 0.25 | 1.2 |
| | | | Untreated Control | 0 |
| | Control of Scentless Mayweed | 34 | 2.0 | 95.3 |
| | | | 1.0 | 94.4 |
| | | | 0.5 | 93.4 |
| | | | 0.25 | 86.7 |
| | | | Untreated Control | 0 |
| | Control of Annual Bluegrass | 34 | 2.0 | 98.2 |
| | | | 1.0 | 93.4 |
| | | | 0.5 | 50.0 |
| | | | 0.25 | 11.1 |
| | | | Untreated Control | 0 |
| | Control of Ladysthumb | 34 | 2.0 | 100.0 |
| | | | 1.0 | 98.8 |
| | | | 0.5 | 90.6 |
| | | | 0.25 | 5.6 |
| | | | Untreated Control | 0 |
| | Control of Chickweed | 34 | 2.0 | 98.8 |
| | | | 1.0 | 98.2 |
| | | | 0.5 | 95.3 |
| | | | 0.25 | 6.6 |
| | | | Untreated Control | 0 |
| | Control of Ivyleaf Speedwell | 34 | 2.0 | 5.6 |
| | | | 1.0 | 4.7 |
| | | | 0.5 | 0 |
| | | | 0.25 | 0 |
| | | | Untreated Control | 0 |
| | Control of Wild Violet | 34 | 2.0 | 88.8 |
| | | | 1.0 | 93.4 |
| | | | 0.5 | 31.5 |
| | | | 0.25 | 4.7 |
| | | | Untreated Control | 0 |
| 31 | Barley Emergence | 18 | 4.0 | 110.3 |
| | | | 2.0 | 82.5 |
| | | | 1.0 | 88.5 |
| | | | 0.5 | 102.1 |

TABLE VII-continued

| Example No. of Compound Tested | Observation | Preemergence Days After Treatment | Rate kg/ha | Percent |
|---|---|---|---|---|
| | | | Untreated Control | 100.0 |
| | Barley Vigor | 25 | 4.0 | 95.0 |
| | | | 2.0 | 96.1 |
| | | | 1.0 | 99.4 |
| | | | 0.5 | 99.4 |
| | | | Untreated Control | 100.0 |
| | Wheat Emergence | 18 | 4.0 | 72.2 |
| | | | 2.0 | 84.3 |
| | | | 1.0 | 102.0 |
| | | | 0.5 | 76.9 |
| | | | Untreated Control | 100.0 |
| | Wheat Vigor | 25 | 4.0 | 98.8 |
| | | | 2.0 | 99.4 |
| | | | 1.0 | 100.0 |
| | | | 0.5 | 99.4 |
| | | | Untreated Control | 100.0 |
| | Control of Wild Oat | 34 | 4.0 | 55.4 |
| | | | 2.0 | 5.6 |
| | | | 1.0 | 2.3 |
| | | | 0.5 | 1.8 |
| | | | Untreated Control | 0 |
| | Control of Catchweed Bedstraw | 34 | 4.0 | 62.5 |
| | | | 2.0 | 31.5 |
| | | | 1.0 | 9.4 |
| | | | 0.5 | 1.2 |
| | | | Untreated Control | 0 |
| | Control of Scentless Mayweed | 34 | 4.0 | 96.0 |
| | | | 2.0 | 96.7 |
| | | | 1.0 | 97.2 |
| | | | 0.5 | 93.4 |
| | | | Untreated Control | 0 |
| | Control of Annual Bluegrass | 34 | 4.0 | 99.4 |
| | | | 2.0 | 98.8 |
| | | | 1.0 | 96.7 |
| | | | 0.5 | 90.6 |
| | | | Untreated Control | 0 |
| | Control of Ladysthumb | 34 | 4.0 | 100.0 |
| | | | 2.0 | 100.0 |
| | | | 1.0 | 97.2 |
| | | | 0.5 | 26.5 |
| | | | Untreated Control | 0 |
| | Control of Chickweed | 34 | 4.0 | 99.4 |
| | | | 2.0 | 98.2 |
| | | | 1.0 | 62.5 |
| | | | 0.5 | 68.5 |
| | | | Untreated Control | 0 |
| | Control of Ivyleaf Speedwell | 34 | 4.0 | 88.8 |
| | | | 2.0 | 3.9 |
| | | | 1.0 | 2.8 |
| | | | 0.5 | 0 |
| | | | Untreated Control | 0 |
| | Control of Wild Violet | 34 | 4.0 | 97.2 |
| | | | 2.0 | 84.2 |
| | | | 1.0 | 11.1 |
| | | | 0.5 | 13.3 |
| | | | Untreated Control | 0 |

EXPERIMENT 6

A field study was also conducted in Great Britain to determine the efficacy and selectivity of Example 3 of the invention when applied postemergent to certain cereal grain crops and weed species. The compound was formulated as an aqueous suspension containing the active agent at a concentration of 1.8% by weight after dilution with water. The formulated compound was then applied approximately four weeks after planting to the emerged crop and weed species. Observations were made at various intervals thereafter to determine the compound's effect against the crop species barley and wheat by comparing crop injury and vigor to untreated control plots, as well as the compounds' ability to control certain weed species. Control ratings are given in percentage of control compared to untreated control plots based upon visual inspection. These results appear in Table VIII below as the average of four replicates.

TABLE VIII

| Observation | Postemergence Days After Treatment | Rate kg/ha | Percent |
|---|---|---|---|
| Barley Injury | 7 | 2.0 | 7.9 |
| | | 1.0 | 6.6 |
| | | 0.5 | 3.3 |
| | | 0.25 | 4.7 |
| | | 0.125 | 1.2 |
| | | Control | 0 |
| Barley Vigor | 16 | 2.0 | 96.0 |
| | | 1.0 | 100.0 |
| | | 0.5 | 100.4 |
| | | 0.25 | 100.0 |
| | | 0.125 | 100.4 |
| | | Control | 100.0 |
| Wheat Injury | 7 | 2.0 | 2.8 |
| | | 1.0 | 2.3 |
| | | 0.5 | 0 |
| | | 0.25 | 0 |
| | | 0.125 | 0 |
| | | Control | 0 |
| Wheat Vigor | 16 | 2.0 | 101.0 |
| | | 1.0 | 101.0 |
| | | 0.5 | 100.0 |
| | | 0.25 | 99.4 |
| | | 0.125 | 98.0 |
| | | Control | 100.0 |
| Control of Blackgrass | 19 | 2.0 | 1.2 |
| | | 1.0 | 1.2 |
| | | 0.5 | 1.2 |
| | | 0.25 | 1.2 |
| | | 0.125 | 0 |
| | | Control | 0 |
| | 35 | 2.0 | 15.8 |
| | | 1.0 | 18.8 |
| | | 0.5 | 4.7 |
| | | 0.25 | 3.9 |
| | | 0.125 | 1.8 |
| | | Control | 0 |
| Control of Wild Oat | 19 | 2.0 | 1.2 |
| | | 1.0 | 1.8 |
| | | 0.5 | 6.6 |
| | | 0.25 | 1.8 |
| | | 0.125 | 0 |
| | | Control | 0 |
| | 35 | 2.0 | 7.9 |
| | | 1.0 | 0 |
| | | 0.5 | 2.8 |
| | | 0.25 | 0 |
| | | 0.125 | 1.8 |
| | | Control | 0 |
| Control of Catchweed Bedstraw | 19 | 2.0 | 0 |
| | | 1.0 | 0 |
| | | 0.5 | 0 |
| | | 0.25 | 0 |
| | | 0.125 | 0 |
| | | Control | 0 |
| | 35 | 2.0 | 18.8 |
| | | 1.0 | 7.9 |
| | | 0.5 | 3.3 |
| | | 0.25 | 1.8 |
| | | 0.125 | 1.8 |
| | | Control | 0 |
| Control of | 19 | 2.0 | 5.6 |

TABLE VIII-continued

| Observation | Postemergence Days After Treatment | Rate kg/ha | Percent |
|---|---|---|---|
| Wild Chamomile | | 1.0 | 1.2 |
| | | 0.5 | 0 |
| | | 0.25 | 1.2 |
| | | 0.125 | 0 |
| | | Control | 0 |
| Control of Scentless Mayweed | 35 | 2.0 | 31.5 |
| | | 1.0 | 1.2 |
| | | 0.5 | 2.8 |
| | | 0.25 | 2.8 |
| | | 0.125 | 0 |
| | | Control | 0 |
| Control of Chickweed | 19 | 2.0 | 97.6 |
| | | 1.0 | 95.3 |
| | | 0.5 | 11.1 |
| | | 0.25 | 4.7 |
| | | 0.125 | 2.3 |
| | | Control | 0 |
| | 35 | 2.0 | 100.0 |
| | | 1.0 | 100.0 |
| | | 0.5 | 68.5 |
| | | 0.25 | 13.3 |
| | | 0.125 | 3.3 |
| | | Control | 0 |
| Control of Ivyleaf Speedwell | 19 | 2.0 | 3.9 |
| | | 1.0 | 5.6 |
| | | 0.5 | 0 |
| | | 0.25 | 0 |
| | | 0.125 | 0 |
| | | Control | 0 |
| | 35 | 2.0 | 50.0 |
| | | 1.0 | 62.5 |
| | | 0.5 | 22.3 |
| | | 0.25 | 15.8 |
| | | 0.125 | 4.7 |
| | | Control | 0 |
| Control of Wild Violet | 19 | 2.0 | 11.1 |
| | | 1.0 | 9.4 |
| | | 0.5 | 3.3 |
| | | 0.25 | 1.2 |
| | | 0.125 | 0 |
| | | Control | 0 |
| | 35 | 2.0 | 18.8 |
| | | 1.0 | 7.9 |
| | | 0.5 | 5.6 |
| | | 0.25 | 3.3 |
| | | 0.125 | 1.8 |
| | | Control | 0 |

Three of the compounds to be employed in accordance with the present invention were formulated as aqueous suspension. The three compounds were the following:

5-chloro-1-tert-butyl-N-methyl-1H-pyrazole-4-carboxamide
5-(trifluoromethyl)-1-(4-chlorophenyl)-N-methyl-1H-pyrazole-4-carboxamide
5-(trifluromethyl)-1-(2,4-dichlorophenyl)-N-methyl-1H-pyrazole-4-carboxamide The composition of each aqueous suspension was as follows:

| Ingredient | Concentration by Weight (percent) |
|---|---|
| active ingredient | 12.2 |
| Tergitol TMN-6 (trimethyl nonyl polyethylene glycol ether, Union Carbide) | 10.0 |
| Zeosyl-200 (hydrated silicone dioxide suspending agent, J.M. Huber Corp.) | 1.0 |
| 2% Xanthan gum thickening agent | 10.0 |
| Antifoam AF-100 (Dow Corning Corp.) | 0.2 |
| Polyfon H (anionic lignosulfonate wetting agent and dispersant, Westvaco Corp.) | 0.3 |
| Water | 66.3 |
| | 100.0 |

Each formulation was prepared by combining the active ingredient with the Tergitol TMN-6, Zeosyl-200, and water. The resulting mixture was ground for several hours until the median particle size of the active ingredient was about 2 to 3 microns. The xanthan gum and AF-100 antifoam were then added to provide a suitable aqueous suspension containing the respective active ingredient.

The present invention provides as yet another embodiment a herbicidal combination comprising one or more herbicidal 2,6-dinitroanilines together with a present 4-pyrazole carboxamide. Such combinations are preferred when a broader spectrum of weed control is desired than either herbicide can provide when used alone.

The term "herbicidal 2,6-dinitroaniline" designates any herbicide comprising the 2,6-dinitroaniline structure; typically, such herbicides include substitution on the aniline nitrogen and additional substituents on the phenyl ring. Examples of such herbicidal 2,6-dinitroanilines include trifluralin, benefin, butralin, chlornidine, dinitramine, ethalfluralin, fluchloralin, isopropalin, nitralin, oryzalin, pendimethalin, prodiamine, profluralin, prosulfalin, and the like, with trifluralin being preferred.

Also provided by this invention is a method for controlling undesired plants which comprises applying to the plants a growth inhibiting amount of a combination of a present compound together with one or more herbicidal 2,6-dinitroanilines. The application rate desired for each of the individual herbicides in the combination is dependent on a number of factors, including the type of weeds and grasses to be controlled, the herbicides that will be used in the combination, climate and soil conditions, the weed population and related factors. Generally, the present compounds will be employed in combination with the dinitroaniline in a ratio of about one to about ten parts by weight of a present active agent and about ten to about one part by weight of the dinitroaniline. More preferable ratios of active ingredients will be from about one to about five parts by weight of a present compound and about five to about one part by weight of the herbicidal 2,6-dinitroaniline. A particularly preferred combination will contain the component herbicides in a weight ratio of about one to one. The combinations will be applied at rates which are effective to control the undesired plants to the desired degree.

The combinations provided herein are formulated in the identical manner which was described for the present novel compounds and intermediates alone, and at similar concentrations. The active components of the combination may be combined as technical materials and later formulated as a whole, or formulated individually and applied either as a combination or individually to the locus of the undesired plants.

The following is an example of a typical herbicidal composition containing a combination of the invention.

| Tank-Mix Composition | |
|---|---|
| Ingredient | Concentration by Weight (Percent) |
| 5-Chloro-1-(3-chlorophenyl)-N—methyl-1H-pyrazole-4-carboxamide formulated as a 50% wettable powder | 60.0 |
| Trifluralin formulated as a 4EC | 40.0 |
| | 100.0 |

The wettable powder formulation containing 50% by weight of the active ingredient is added to water and the mixture agitated while adding the emulsifiable concentrate containing the trifluralin at the rate of 4 lbs/gal (0.48 kg/l.). The mixture is sprayed on the soil surface and then typically incorporated at a depth of about 3 to 4 inches prior to planting.

The herbicidal activity of a representative combination of the present invention is illustrated by the following field study.

EXPERIMENT 7

A combination of Example 1 of present invention and trifluralin was tested in a field study conducted in Manitoba, Canada on wheat against several weed species. Trifluralin, formulated as an emulsifiable concentrate at a test compound concentration of 4 lbs/gallon (0.48 kg/l), and Example 1, formulated as a 50% wettable powder as described above, were tank-mix formulated and incorporated into the soil after the crop was planted. The results of this test appear below in Table IX as the average of three replicates.

TABLE IX

| | Tank-Mix Combination | | |
|---|---|---|---|
| Observation | Days After Treatment | Treatment | Rate kg/ha | Percent |
| Wheat Injury | 52 | Example 1 + Trifluralin | 4.0 + 0.7 | 1.7 |
| | | | 3.0 + 0.7 | 1.7 |
| | | | 2.0 + 0.7 | 8.3 |
| | | | 1.5 + 0.7 | 5.0 |
| | | Control | | 0 |
| | 77 | Example 1 + Trifluralin | 4.0 + 0.7 | 0 |
| | | | 3.0 + 0.7 | 1.7 |
| | | | 2.0 + 0.7 | 5.0 |
| | | | 1.5 + 0.7 | 5.0 |
| | | Control | | 0 |
| Wheat Root Injury | 52 | Example 1 + Trifluralin | 4.0 + 0.7 | 3.3 |
| | | | 3.0 + 0.7 | 10.0 |
| | | | 2.0 + 0.7 | 0 |
| | | | 1.5 + 0.7 | 3.3 |
| | | Control | | 0 |
| Control of Redroot Pigweed | 52 | Example 1 + Trifluralin | 4.0 + 0.7 | 96.3 |
| | | | 3.0 + 0.7 | 93.0 |
| | | | 2.0 + 0.7 | 99.7 |
| | | | 1.5 + 0.7 | 100.0 |
| | | Control | | 0 |
| | 77 | Example 1 + Trifluralin | 4.0 + 0.7 | 98.0 |
| | | | 3.0 + 0.7 | 98.0 |
| | | | 2.0 + 0.7 | 100.0 |
| | | | 1.5 + 0.7 | 100.0 |
| | | Control | | 0 |
| Control of Common Lambsquarters | 52 | Example 1 + Trifluralin | 4.0 + 0.7 | 98.3 |
| | | | 3.0 + 0.7 | 100.0 |
| | | | 2.0 + 0.7 | 99.3 |
| | | | 1.5 + 0.7 | 100.0 |
| | | Control | | 0 |
| | 77 | Example 1 + Trifluralin | 4.0 + 0.7 | 100.0 |
| | | | 3.0 + 0.7 | 100.0 |
| | | | 2.0 + 0.7 | 100.0 |
| | | | 1.5 + 0.7 | 100.0 |
| | | Control | | 0 |

TABLE IX-continued

| | Tank-Mix Combination | | |
|---|---|---|---|
| Observation | Days After Treatment | Treatment | Rate kg/ha | Percent |
| Control of Green Smartweed | 52 | Example 1 + Trifluralin | 4.0 + 0.7 | 100.0 |
| | | | 3.0 + 0.7 | 98.3 |
| | | | 2.0 + 0.7 | 99.7 |
| | | | 1.5 + 0.7 | 98.0 |
| | | Control | | 0 |
| | 77 | Example 1 + Trifluralin | 4.0 + 0.7 | 100.0 |
| | | | 3.0 + 0.7 | 99.7 |
| | | | 2.0 + 0.7 | 99.7 |
| | | | 1.5 + 0.7 | 100.0 |
| | | Control | | 0 |
| Control of Green Foxtail | 52 | Example 1 + Trifluralin | 4.0 + 0.7 | 100.0 |
| | | | 3.0 + 0.7 | 100.0 |
| | | | 2.0 + 0.7 | 100.0 |
| | | | 1.5 + 0.7 | 100.0 |
| | | Control | | 0 |

The present compounds have also been found to display useful activity as aquatic algicides. It is therefore provided as another embodiment of the invention a method for controlling the growth of aquatic algae which comprises applying to the water containing said algae a growth inhibiting amount of a 4-pyrazole carboxamide of the invention. These active agents are generally applied at rates effective to inhibit the growth of algae without causing significant toxicity to other aquatic life. The compounds are applied at rates in the range of from about 20.0 ppm to about 0.1 ppm, more preferably at 10 ppm to 0.5 ppm.

EXPERIMENT 8

The initial screening procedure used to detect aquatic algicidal activity was conducted at a test compound concentration of 10 ppm against the algae *Chlorella vulgaris* (A), *Scenedesmus quadricanda* (B), *Anacystis nidulans* (C) and *Anabaena flos-aquae* (D). Certain test compounds were also evaluated against additional species of algae at lower concentration rates. These species are as follows:

E. *Stichococcus bascillaris*
F. *Chlamydomonas moewussi*
G. *Anabaena* spp.
H. *Anabaena spiroides*

These species of algae were grown on agar slants containing artificial Hughes media. Each species of algae was suspended in 5 ml of an aqueous, sterile Hughes media by washing the agar slants. This solution was then pipetted into a volume of 400 ml of the sterile media. Two ml of the inoculated media was transferred via syringe to a sterilized 12 ml vial, to which 10 µl of the formulated compound was added to obtain a concentration of 10 ppm of the compound. The compounds were formulated by adding 10 mg compound to 0.5 ml acetone and 4.5 ml sterile 0.1 percent Tween 80. Lower concentrations were obtained by further serial dilution. After addition the vial was stoppered.

Observations were made 7 days after treatment and the activity of the test compounds against algae growth is recorded in Table X according to the following scale:
1 = no effect
2 = slight effect
3 = moderate effect
4 = heavy control
5 = 100% control

TABLE X

Aquatic Algicide

| Example No. of Compound Tested | Concentration ppm | Aquatic Algae | | | | | | | |
|---|---|---|---|---|---|---|---|---|---|
| | | A | B | C | D | E | F | G | H |
| 1 | 10.0 | 5 | 5 | 5 | 5 | | | | |
| | 1.0 | 1 | 1 | 1 | 1 | 2 | 1 | 1 | 3 |
| | 0.5 | 1 | 1 | 1 | 1 | 1 | 1 | 1 | 1 |
| 2 | 10.0 | 1 | 5 | 5 | 5 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 3 | 10.0 | 5 | 5 | 5 | 5 | 5 | | | |
| | 1.0 | 1 | 1 | 1 | 1 | 2 | 1 | 2 | 5 |
| | 0.5 | 1 | 1 | 1 | 1 | 1 | 1 | 1 | 1 |
| 4 | 10.0 | 1 | 5 | 2 | 1 | | | | |
| 5 | 10.0 | 3 | 3 | 2 | 1 | | | | |
| 6 | 10.0 | 4 | 5 | 5 | 4 | | | | |
| | 1.0 | 1 | 1 | 1 | 1 | 1 | 1 | 2 | 2 |
| | 0.5 | 1 | 1 | 1 | 1 | 1 | 1 | 1 | 1 |
| 7 | 10.0 | 2 | 5 | 5 | 3 | | | | |
| 8 | 10.0 | 5 | 5 | 5 | 5 | | | | |
| | 1.0 | 1 | 1 | 1 | 1 | 1 | 1 | 1 | 2 |
| | 0.5 | 1 | 1 | 1 | 1 | 1 | 1 | 1 | 2 |
| 9 | 10.0 | 1 | 3 | 2 | 1 | | | | |
| 10 | 10.0 | 3 | 5 | 5 | 4 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 11 | 10.0 | 1 | 1 | 1 | 1 | | | | |
| 12 | 10.0 | 4 | 4 | 4 | 3 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 13 | 10.0 | 3 | 5 | 4 | 1 | | | | |
| 14 | 10.0 | 2 | 5 | 3 | 1 | | | | |
| 15 | 10.0 | 2 | 4 | 2 | 2 | | | | |
| 16 | 10.0 | 5 | 5 | 5 | 2 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 17 | 10.0 | 2 | 5 | 3 | 1 | | | | |
| 18 | 10.0 | 5 | 5 | 5 | 4 | | | | |
| | 10.0 | 5 | 4 | 5 | 5 | | | | |
| | 1.0 | 1 | 1 | 1 | 1 | 1 | 1 | 1 | 4 |
| | 1.0 | 1 | 1 | 1 | 1 | 1 | 1 | 1 | 1 |
| | 0.5 | 1 | 1 | 1 | 1 | 1 | 1 | 1 | 1 |
| | 0.5 | 1 | 1 | 1 | 1 | 1 | 1 | 1 | 1 |
| 19 | 10.0 | 5 | 5 | 5 | 4 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 20 | 10.0 | 5 | 5 | 5 | 5 | 5 | | | |
| | 1.0 | 1 | 1 | 1 | 1 | 1 | 1 | 1 | 1 |
| | 0.5 | 1 | 1 | 1 | 1 | 1 | 1 | 1 | 1 |
| 21 | 10.0 | 2 | 1 | 1 | 1 | | | | |
| 23 | 10.0 | 5 | 5 | 5 | 3 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 24 | 10.0 | 2 | 5 | 5 | 2 | | | | |
| 25 | 10.0 | 3 | 5 | 4 | 1 | | | | |
| 26 | 10.0 | 2 | 1 | 1 | 2 | | | | |
| 27 | 10.0 | 1 | 1 | 1 | 1 | | | | |
| 28 | 10.0 | 4 | 5 | 5 | 5 | | | | |
| | 1.0 | 1 | 2 | 2 | 1 | 1 | 2 | 1 | 1 |
| | 0.5 | 1 | 1 | 2 | 1 | 1 | 2 | 1 | 1 |
| 29 | 10.0 | 4 | 5 | 5 | 5 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 30 | 10.0 | 5 | 5 | 5 | 5 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 31 | 10.0 | 5 | 5 | 5 | 5 | | | | |
| | 1.0 | 1 | 1 | 1 | 1 | 3 | 1 | 1 | 5 |
| | 0.5 | 1 | 1 | 1 | 1 | 1 | 1 | 1 | 1 |
| 32 | 10.0 | 1 | 1 | 1 | 1 | | | | |
| 33 | 10.0 | 2 | 5 | 4 | 4 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 34 | 10.0 | 3 | 5 | 3 | 1 | | | | |
| 35 | 10.0 | 5 | 5 | 1 | 1 | | | | |
| 36 | 10.0 | 5 | 5 | 5 | 5 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 37 | 10.0 | 4 | 5 | 5 | 5 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 38 | 10.0 | 3 | 5 | 5 | 5 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 39 | 10.0 | 5 | 5 | 5 | 5 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 40 | 10.0 | 5 | 5 | 5 | 5 | | | | |
| | 1.0 | 3 | 4 | 1 | 1 | 4 | 1 | 3 | 5 |
| | 0.5 | 1 | 3 | 1 | 1 | 2 | 1 | 2 | 5 |
| 41 | 10.0 | 1 | 4 | 1 | 1 | | | | |
| 42 | 10.0 | 5 | 5 | 5 | 5 | | | | |
| | 1.0 | 2 | 1 | 1 | 1 | 1 | 1 | 1 | 1 |
| | 0.5 | 1 | 1 | 1 | 1 | 1 | 1 | 1 | 1 |
| 44 | 10.0 | 4 | 4 | 4 | 3 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 45 | 10.0 | 2 | 3 | 3 | | | | | |
| 47 | 10.0 | 5 | 5 | 5 | 5 | | | | |
| | 1.0 | 3 | 1 | 1 | 1 | 3 | 2 | 3 | 5 |
| | 0.5 | 1 | 1 | 1 | 1 | 1 | 1 | 1 | 4 |
| 49 | 10.0 | 4 | 3 | 2 | 1 | | | | |
| 50 | 10.0 | 5 | 5 | 5 | 4 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 51 | 10.0 | 1 | 5 | 5 | 1 | | | | |
| 52 | 10.0 | 4 | 4 | 5 | 4 | | | | |
| 53 | 10.0 | 1 | 5 | 5 | 4 | | | | |
| | 1.0 | 1 | 5 | 2 | 2 | 2 | 2 | 1 | 5 |
| | 0.5 | 1 | 2 | 1 | 1 | 1 | 2 | 1 | 3 |
| 54 | 10.0 | 3 | 5 | 5 | 4 | | | | |
| | 1.0 | 1 | 1 | 1 | 1 | 1 | 1 | 2 | 1 |
| | 0.5 | 1 | 1 | 1 | 1 | 1 | 1 | 2 | 1 |
| 55 | 10.0 | 5 | 5 | 5 | 5 | | | | |
| | 1.0 | 2 | 4 | 2 | 2 | 3 | 2 | 3 | 5 |
| | 0.5 | 1 | 3 | 1 | 1 | 2 | 2 | 2 | 5 |
| 56 | 10.0 | 2 | 4 | 1 | 1 | | | | |
| 57 | 10.0 | 3 | 5 | 5 | 5 | | | | |
| | 1.0 | 1 | 5 | 1 | 1 | 1 | 1 | 1 | 5 |
| | 0.5 | 1 | 2 | 1 | 1 | 1 | 1 | 1 | 2 |
| 58 | 10.0 | 5 | 5 | 5 | 5 | | | | |
| | 1.0 | 1 | 4 | 4 | 1 | 1 | 4 | 3 | 1 |
| | 0.5 | | | | | 1 | 4 | 1 | 1 |
| 59 | 10.0 | 5 | 5 | 5 | 5 | | | | |
| | 1.0 | 1 | 1 | 1 | 1 | 1 | 1 | 3 | 3 |
| | 0.5 | 1 | 1 | 1 | 1 | 1 | 1 | 2 | 3 |
| 61 | 10.0 | 4 | 4 | 4 | 2 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 62 | 10.0 | 5 | 5 | 5 | 5 | | | | |
| | 1.0 | 4 | 5 | 4 | 4 | 4 | 4 | 4 | 5 |
| | 0.5 | 1 | 4 | 1 | 1 | 3 | 2 | 3 | 5 |
| 63 | 10.0 | 1 | 4 | 4 | 2 | | | | |
| 64 | 10.0 | 3 | 1 | 5 | 4 | | | | |
| | 1.0 | 1 | 1 | 2 | 1 | 1 | 4 | 1 | 1 |
| | 0.5 | 1 | 2 | 1 | 1 | 1 | 2 | 1 | 1 |
| 65 | 10.0 | 3 | 5 | 4 | 3 | | | | |
| 66 | 10.0 | 5 | 5 | 5 | 5 | | | | |
| | 1.0 | 1 | 4 | 2 | 1 | 4 | 4 | 1 | 5 |
| | 0.5 | 1 | 2 | 1 | 1 | 2 | 1 | 1 | 5 |
| 67 | 10.0 | 4 | 5 | 5 | 4 | | | | |
| | 1.0 | 1 | 1 | 1 | 1 | 1 | 1 | 1 | 1 |
| | 0.5 | 1 | 1 | 1 | 1 | 1 | 1 | 1 | 1 |
| 68 | 10.0 | 3 | 5 | 5 | 4 | | | | |
| | 1.0 | 1 | 1 | 3 | 1 | 1 | 3 | 1 | 1 |
| | 0.5 | 3 | 1 | 3 | 1 | 1 | 1 | 1 | 1 |
| 70 | 10.0 | 5 | 1 | 5 | 4 | | | | |
| | 1.0 | 3 | 3 | 2 | 3 | 1 | 1 | 4 | 5 |
| | 0.5 | 2 | 1 | 1 | 1 | 1 | 1 | 3 | 5 |
| 71 | 10.0 | 5 | 5 | 5 | 5 | | | | |
| | 1.0 | 4 | 4 | 3 | 3 | 1 | 2 | 4 | 5 |
| | 0.5 | 1 | 1 | 1 | 1 | 1 | 1 | 3 | 5 |
| 72 | 10.0 | 5 | 5 | 5 | 4 | | | | |
| | 1.0 | 1 | 1 | 1 | 1 | 1 | 1 | 3 | 5 |
| | 0.5 | 1 | 1 | 1 | 1 | 1 | 1 | 3 | 3 |
| 73 | 10.0 | 5 | 5 | 5 | 5 | | | | |

TABLE X-continued

| Example No. of Compound Tested | Concentration ppm | Aquatic Algicide |||||||| 
| | | Aquatic Algae ||||||||
| | | A | B | C | D | E | F | G | H |
| | 1.0 | 3 | 3 | 1 | 1 | 1 | 1 | 1 | 5 |
| | 0.5 | 1 | 1 | 1 | 1 | 1 | 1 | 1 | 1 |
| 74 | 10.0 | 3 | 5 | 4 | 3 | | | | |
| 75 | 10.0 | 1 | 5 | 1 | | | | | |
| 76 | 10.0 | 4 | 5 | 4 | 4 | | | | |
| | 1.0 | 2 | 4 | 4 | 1 | 1 | 4 | 4 | 1 |
| | 0.5 | 1 | 4 | 4 | 1 | 1 | 4 | 4 | 3 |
| 78 | 10.0 | 1 | 4 | 5 | | | | | |
| | 1.0 | | 1 | 1 | 1 | 1 | 1 | 1 | 5 |
| | 0.5 | | 1 | 1 | 1 | 1 | 1 | 1 | 5 |
| 80 | 10.0 | 1 | 4 | 4 | 3 | | | | |
| 81 | 10.0 | 1 | 5 | 3 | 2 | | | | |

Many of the compounds of the present invention have also exhibited useful activity against the fungal disease Septoria leaf blotch. When employed in the treatment of this plant fungal disease, the compounds are applied to the plants in a disease inhibiting and non-herbicidal amount. The term "disease inhibiting and non-herbicidal amount", as used herein, refers to an amount of a compound of the invention which kills or stunts the plant disease for which control is desired, but is not significantly toxic to the plant. This amount will generally be from about 1 to 1000 ppm, with 10 to 500 ppm being preferred. The exact concentration of compound required varies with the type of formulation employed, the method of application, the particular plant species, climate conditions and the like. The compounds are preferably formulated prior to application for the control of Septoria. These formulations are similar to those outlined above for herbicidal use.

We claim:

1. A compound of the formula

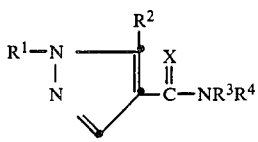

wherein $R^1$ is tert-butyl, $C_5$–$C_6$ cycloalkyl,

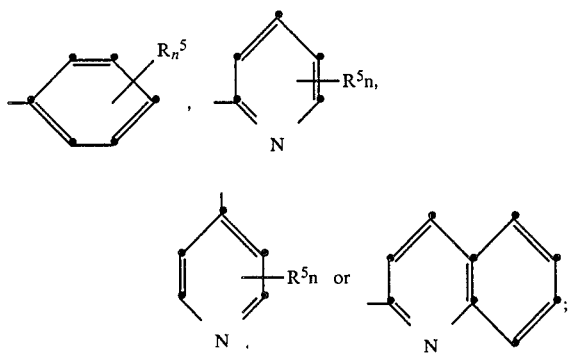

$R^2$ is halogen, $C_1$–$C_4$ alkyl, trifluoromethyl, $C_1$–$C_4$ alkylthio or $C_1$–$C_4$ alkylsulfonyl;
$R^3$ is hydrogen, $C_1$–$C_4$ alkyl or $C_1$–$C_4$ alkoxy;
$R^4$ is cyclopropyl, $C_1$–$C_4$ alkyl or $C_1$–$C_4$ alkoxy;
$R^5$ is halogen, $C_1$–$C_4$ alkyl, $C_1$–$C_4$ alkoxy, $C_1$–$C_4$ haloalkyl, $C_1$–$C_4$ haloalkoxy or nitro;
X is O or S; and
n is 0–3;
with the following provisos: the combined total of carbon atoms for $R^3$ and $R^4$ does not exceed 5; when $R^1$ is phenyl, $R^5$ is $C_1$–$C_4$ alkyl, and $R^2$ is halogen, alkoxy, alkylthio, or alkylsulfonyl, the $R^5$ substituent exists at other than the 2 or 6 position of the phenyl ring; when $R^3$ is $C_1$–$C_4$ alkoxy, $R^4$ is other than $C_1$–$C_4$ alkoxy; and when $R^1$ is phenyl, $R^5$ is $C_1$–$C_4$ alkoxy and $R^2$ is other than bromine, the $R^5$ substituent exists at other than the 3 or 5 position of the phenyl ring.

2. A compound of claim 1 wherein $R^2$ is chlorine or bromine.

3. The compound of claim 2 which is 5-bromo-1-(3-fluorophenyl)-N-methyl-1H-pyrazole-4-carboxamide.

4. A compound of claim 2 which is 5-chloro-1-(4-fluorophenyl)-N-methyl-1H-pyrazole-4-carboxamide.

5. The compound of claim 2 which is 5-chloro-1-(3-chlorophenyl)-N-methyl-1H-pyrazole-4-carboxamide.

6. The compound of claim 2 which is 5-chloro-1-(4-bromophenyl)-N-methyl-1H-pyrazole-4-carboxamide.

7. The compound of claim 2 which is 5-bromo-1-phenyl-N-methyl-1H-pyrazole-4-carboxamide.

8. The compound of claim 2 which is 5-chloro-1-tert-butyl-N-methyl-1H-pyrazole-4-carboxamide.

9. A compound of claim 1 wherein $R^2$ is trifluoromethyl.

10. The compound of claim 9 which is 5-(trifluoromethyl)-1-tert-butyl-N-methyl-1H-pyrazole-4-carboxamide.

11. The method of claim 9 which is 5-(trifluoromethyl)-1-phenyl-N-methyl-1H-pyrazole-4-carboxamide.

12. The compound of claim 9 which is 5-trifluoromethyl)-1-(4-chlorophenyl)-N-methyl-1H-pyrazole-4-carboxamide.

13. The compound of claim 9 which is 5-(trifluoromethyl)-1-(2,4-dichlorophenyl)-N-methyl-1H-pyrazole-4-carboxamide.

14. A method for controlling undesired plants which comprises applying to the plants a growth inhibiting amount of a compound of claim 1.

15. A method of claim 14 wherein $R^2$ is chlorine or bromine.

16. The method of claim 15 in which the compound is 5-bromo-1-(3-fluorophenyl)-N-methyl-1H-pyrazole-4-carboxamide.

17. The method of claim 15 in which the compound is 5-chloro-1-(4-fluorophenyl)-N-methyl-1H-pyrazole-4-carboxamide.

18. The method of claim 15 in which the compound is 5-chloro-1-(3-chlorophenyl)-N-methyl-1H-pyrazole-4-carboxamide.

19. The method of claim 15 in which the compound is 5-chloro-1-(4-bromophenyl)-N-methyl-1H-pyrazole-4-carboxamide.

20. The method of claim 15 in which the compound is 5-bromo-1-phenyl-N-methyl-1H-pyrazole-4-carboxamide.

21. The method of claim 15 in which the compound is 5-chloro-1-tert-butyl-N-methyl-1H-pyrazole-4-carboxamide.

22. A method of claim 14 wherein $R^2$ is trifluoromethyl.

23. The method of claim 22 in which the compound is 5-(trifluoromethyl)-1-tert-butyl-N-methyl-1H-pyrazole-4-carboxamide.

24. The method of claim 22 in which the compound is 5-(trifluoromethyl)-1-phenyl-N-methyl-1H-pyrazole-4-carboxamide.

25. The method of claim 22 in which the compound is 5-(trifluoromethyl)-1-(4-chlorophenyl)-N-methyl-1H-pyrazole-4-carboxamide.

26. The method of claim 22 in which the compound is 5-(trifluoromethyl)-1-(2,4-dichlorophenyl)-N-methyl-1H-pyrazole-4-carboxamide.

27. A method for controlling the growth of aquatic algae which comprises applying to the water containing said algae a growth inhibiting amount of a compound of claim 1.

28. A composition which comprises a plant growth inhibiting amount of a compound of claim 1 and an agriculturally-acceptable carrier.

29. A composition of claim 28 wherein $R^2$ is chlorine or bromine.

30. The composition of claim 29 in which the compound is 5-bromo-1-(3-fluorophenyl)-N-methyl-1H-pyrazole-4-carboxamide.

31. The composition of claim 29 in which the compound is 5-chloro-1-(4-fluorophenyl)-N-methyl-1H-pyrazole-4-carboxamide.

32. The composition of claim 29 in which the compound is 5-chloro-1-(3-chlorophenyl)-N-methyl-1H-pyrazole-4-carboxamide.

33. The composition of claim 29 in which the compound is 5-chloro-1-(4-bromophenyl)-N-methyl-1H-pyrazole-4-carboxamide.

34. The composition of claim 29 in which the compound is 5-bromo-1-phenyl-N-methyl-1H-pyrazole-4-carboxamide.

35. The composition of claim 29 in which the compound is 5-chloro-1-tert-butyl-N-methyl-1H-pyrazole-4-carboxamide.

36. The composition of claim 28 wherein $R^2$ is trifluoromethyl.

37. The composition of claim 36 in which the compound is 5-(trifluoromethyl)-1-phenyl-N-methyl-1H-pyrazole-4-carboxamide.

38. The composition of claim 36 in which the compound is 5-(trifluoromethyl)-1-tert-butyl-N-methyl-1H-pyrazole-4-carboxamide.

39. The composition of claim 36 in which the compound is 5-(trifluoromethyl)-1-(4-chlorophenyl)-N-methyl-1H-pyrazole-4-carboxamide.

40. The composition of claim 36 in which the compound is 5-(trifluoromethyl)-1-(2,4-dichlorophenyl)-N-methyl-1H-pyrazole-4-carboxamide.

41. A herbicidal combination comprising one or more herbicidal 2,6-dinitroanilines together with a compound of claim 1.

42. A combination of claim 41 wherein the dinitroaniline is trifluralin.

43. A method for controlling undesired plants which comprises applying to the plants a growth inhibiting amount of a combination of claim 41.

44. A method of controlling weeds in a wheat or corn crop which comprises applying preemergently an effective amount of an active agent which is a compound of claim 1.

45. The method of claim 44 wherein the active agent is 5-chloro-1-tert-butyl-N-methyl-1H-pyrazole-4-carboxamide.

46. The method of claim 44 wherein the active agent is 5-(trifluoromethyl)-1-phenyl-N-methyl-1H-pyrazole-4-carboxamide.

47. The method of claim 44 wherein the active agent is 5-(trifluoromethyl)-1-(4-chlorophenyl)-N-methyl-1H-pyrazole-4-carboxamide.

48. The method of claim 44 wherein the active agent is 5-(trifluoromethyl)-1-(2,4-dichlorophenyl)-N-methyl-1H-pyrazole-4-carboxamide.

* * * * *